US008868436B2

(12) United States Patent
Gotthardt

(10) Patent No.: US 8,868,436 B2
(45) Date of Patent: Oct. 21, 2014

(54) DATA STRUCTURE, METHOD, AND SYSTEM FOR PREDICTING MEDICAL CONDITIONS

(75) Inventor: Frank Gotthardt, Eitelborn (DE)

(73) Assignee: Compugroup Medical AG, Koblenz (DE)

( * ) Notice: Subject to any disclaimer, the term of this patent is extended or adjusted under 35 U.S.C. 154(b) by 365 days.

(21) Appl. No.: 13/007,855

(22) Filed: Jan. 17, 2011

(65) Prior Publication Data

US 2011/0225114 A1 Sep. 15, 2011

(30) Foreign Application Priority Data

| Mar. 11, 2010 | (EP) | ................................ EP10156171 |
| Jun. 29, 2010 | (EP) | ................................ EP10167641 |
| Aug. 18, 2010 | (EP) | ................................ EP10173163 |
| Aug. 18, 2010 | (EP) | ................................ EP10173175 |
| Aug. 18, 2010 | (EP) | ................................ EP10173198 |
| Dec. 13, 2010 | (EP) | ................................ EP10194677 |
| Dec. 13, 2010 | (EP) | ................................ EP10194681 |
| Dec. 23, 2010 | (EP) | ................................ EP10196745 |

(51) Int. Cl.
*G06Q 10/00* (2012.01)
*G06F 19/00* (2011.01)
*G06F 21/62* (2013.01)
*H04L 9/08* (2006.01)

(52) U.S. Cl.
CPC .......... *G06F 19/345* (2013.01); *G06F 19/3443* (2013.01); *G06F 19/3418* (2013.01); *G06F 21/6245* (2013.01); *H04L 9/0816* (2013.01); *G06F 19/322* (2013.01); *G06F 19/326* (2013.01); *G06F 19/363* (2013.01)
USPC ................................ 705/2; 705/3

(58) Field of Classification Search
USPC ........................................................... 705/2
See application file for complete search history.

(56) References Cited

U.S. PATENT DOCUMENTS

| 4,864,616 | A | 9/1989 | Pond et al. |
| 4,879,747 | A | 11/1989 | Leighton et al. |
| 5,210,795 | A | 5/1993 | Lipner et al. |
| 5,721,781 | A | 2/1998 | Deo et al. |
| 5,754,675 | A | 5/1998 | Valadier |
| 5,832,091 | A | 11/1998 | Tomko et al. |
| 6,031,910 | A | 2/2000 | Deindl et al. |
| 6,167,521 | A | 12/2000 | Smith et al. |
| 6,212,519 | B1 | 4/2001 | Segal |
| 6,230,269 | B1 | 5/2001 | Spies et al. |
| 6,299,062 | B1 | 10/2001 | Hwang |

(Continued)

FOREIGN PATENT DOCUMENTS

| DE | 10134489 A1 | 1/2003 |
| DE | 10258769 | 6/2004 |

(Continued)

OTHER PUBLICATIONS

Briscoe, R., "Chapter 18: The Implications of Pervasive Computing on Network Design," Intelligent Spaces: The Application of Pervasive ICT, 2006, pp. 287-322.

Chinaei, Amir, "Access Control Administration with Adjustable Decentralization," Thesis—University of Waterloo, Waterloo, Ontario, Canada; 2007; 139 pages.

Ray, I. et al., "A Cryptographic Solution to Implement Access Control in a Hierarchy and More," SACMAT '02, ACM; Jun. 2-3, 2002, pp. 65-73.

(Continued)

*Primary Examiner* — Hiep V Nguyen

(57) ABSTRACT

The invention relates to a data structure comprising a plurality of biomedical parameters for providing a plurality of biomedical parameter values as input to a medical decision support system.

16 Claims, 13 Drawing Sheets

(56) References Cited

U.S. PATENT DOCUMENTS

| | | |
|---|---|---|
| 6,523,116 B1 | 2/2003 | Berman |
| 6,529,886 B1 | 3/2003 | Campana |
| 6,532,472 B1 | 3/2003 | Arrouye et al. |
| 6,687,375 B1 | 2/2004 | Matyas et al. |
| 6,754,655 B1 | 6/2004 | Segal |
| 6,904,150 B1 | 6/2005 | Dent |
| 6,950,523 B1 | 9/2005 | Brickell et al. |
| 6,959,381 B2 | 10/2005 | Wheeler et al. |
| 6,963,859 B2 | 11/2005 | Stefik et al. |
| 6,988,088 B1 * | 1/2006 | Miikkulainen et al. ......... 706/14 |
| 7,050,584 B1 | 5/2006 | Hoffmann et al. |
| 7,181,017 B1 | 2/2007 | Nagel et al. |
| 7,254,709 B1 | 8/2007 | Richard |
| 7,266,699 B2 | 9/2007 | Newman et al. |
| 7,393,532 B1 | 7/2008 | de Sauvage et al. |
| 7,502,469 B2 | 3/2009 | Antoine |
| 7,548,621 B1 | 6/2009 | Smith et al. |
| 7,590,236 B1 | 9/2009 | Boneh et al. |
| 7,634,091 B2 | 12/2009 | Zhou et al. |
| 7,634,817 B2 | 12/2009 | Klug et al. |
| 7,643,817 B2 | 1/2010 | Klug et al. |
| 7,742,932 B2 | 6/2010 | Segal |
| 7,752,443 B2 | 7/2010 | Genty et al. |
| 7,844,717 B2 | 11/2010 | Herz et al. |
| 7,894,448 B1 | 2/2011 | Lillibridge et al. |
| 7,895,666 B1 | 2/2011 | Eshghi et al. |
| 7,952,443 B2 | 5/2011 | Chang et al. |
| 7,958,362 B2 | 6/2011 | Hwang |
| 7,962,761 B1 | 6/2011 | Spalka et al. |
| 8,024,581 B2 | 9/2011 | Spalka et al. |
| 8,137,922 B2 * | 3/2012 | Dieplinger et al. ............ 435/7.1 |
| 8,145,718 B1 | 3/2012 | Kacker et al. |
| 8,224,979 B2 | 7/2012 | Herz et al. |
| 8,266,435 B2 | 9/2012 | Spalka et al. |
| 8,516,267 B2 | 8/2013 | Spalka et al. |
| 8,522,011 B2 | 8/2013 | Spalka et al. |
| 2001/0039503 A1 * | 11/2001 | Chan et al. ........................ 705/2 |
| 2002/0002061 A1 | 1/2002 | Felsher |
| 2002/0004899 A1 | 1/2002 | Azuma |
| 2002/0010679 A1 | 1/2002 | Felsher |
| 2002/0021810 A1 | 2/2002 | Solinas |
| 2002/0025045 A1 | 2/2002 | Raike |
| 2002/0091687 A1 | 7/2002 | Eglington |
| 2002/0103765 A1 | 8/2002 | Ohmori |
| 2002/0133707 A1 | 9/2002 | Newcombe |
| 2002/0184224 A1 | 12/2002 | Haff et al. |
| 2003/0046560 A1 | 3/2003 | Kohshiro |
| 2003/0065776 A1 | 4/2003 | Malik et al. |
| 2003/0115457 A1 | 6/2003 | Wildish et al. |
| 2003/0118200 A1 | 6/2003 | Beaucoup et al. |
| 2003/0149854 A1 | 8/2003 | Yoshino et al. |
| 2003/0160815 A1 | 8/2003 | Muschetto |
| 2003/0190046 A1 | 10/2003 | Kamerman et al. |
| 2004/0025036 A1 | 2/2004 | Balard et al. |
| 2004/0059925 A1 | 3/2004 | Benhammou et al. |
| 2004/0083182 A1 | 4/2004 | Moribatake et al. |
| 2004/0109567 A1 | 6/2004 | Yang et al. |
| 2004/0181679 A1 | 9/2004 | Dettinger et al. |
| 2004/0199764 A1 | 10/2004 | Koechling et al. |
| 2005/0091341 A1 | 4/2005 | Knight et al. |
| 2005/0138353 A1 | 6/2005 | Spies et al. |
| 2005/0157880 A1 | 7/2005 | Kurn et al. |
| 2005/0163320 A1 | 7/2005 | Brown et al. |
| 2005/0163549 A1 | 7/2005 | Shima et al. |
| 2005/0238175 A1 | 10/2005 | Plotkin et al. |
| 2005/0273604 A1 | 12/2005 | Lai |
| 2005/0283608 A1 | 12/2005 | Halcrow et al. |
| 2006/0031301 A1 | 2/2006 | Herz et al. |
| 2006/0034456 A1 | 2/2006 | McGough |
| 2006/0095771 A1 | 5/2006 | Appenzeller et al. |
| 2006/0106805 A1 | 5/2006 | Aaron |
| 2006/0153364 A1 | 7/2006 | Beeson |
| 2006/0153368 A1 | 7/2006 | Beeson |
| 2006/0153370 A1 | 7/2006 | Beeson |
| 2006/0277413 A1 | 12/2006 | Drews |
| 2007/0028108 A1 | 2/2007 | Cowburn et al. |
| 2007/0089168 A1 | 4/2007 | Wang et al. |
| 2007/0112782 A1 | 5/2007 | Lobach et al. |
| 2007/0118891 A1 | 5/2007 | Buer |
| 2007/0165864 A1 | 7/2007 | Nagase et al. |
| 2007/0198848 A1 | 8/2007 | Bjorn |
| 2007/0206789 A1 | 9/2007 | Sotoodeh |
| 2007/0208800 A1 * | 9/2007 | Frohlich et al. ................ 709/203 |
| 2007/0273518 A1 | 11/2007 | Lupoli et al. |
| 2007/0294533 A1 | 12/2007 | Toh et al. |
| 2008/0005086 A1 | 1/2008 | Moore |
| 2008/0022361 A1 | 1/2008 | Bharadwaj et al. |
| 2008/0040603 A1 | 2/2008 | Stedron |
| 2008/0126794 A1 | 5/2008 | Wang et al. |
| 2008/0148047 A1 | 6/2008 | Appenzeller et al. |
| 2008/0152146 A1 | 6/2008 | Conrado et al. |
| 2008/0154782 A1 | 6/2008 | Kang et al. |
| 2008/0183656 A1 | 7/2008 | Perng et al. |
| 2008/0247540 A1 | 10/2008 | Ahn et al. |
| 2008/0250253 A1 | 10/2008 | Beckwith et al. |
| 2008/0263050 A1 | 10/2008 | Randazzo et al. |
| 2008/0267394 A1 | 10/2008 | Nan et al. |
| 2008/0270579 A1 | 10/2008 | Herz et al. |
| 2008/0301459 A1 | 12/2008 | Ebeid |
| 2009/0006860 A1 | 1/2009 | Ross |
| 2009/0041249 A1 | 2/2009 | Tanaka et al. |
| 2009/0129600 A1 | 5/2009 | Brickell et al. |
| 2009/0138727 A1 | 5/2009 | Campello de Souza |
| 2009/0158035 A1 | 6/2009 | Stultz |
| 2009/0187419 A1 | 7/2009 | Renganathan et al. |
| 2009/0187757 A1 | 7/2009 | Kerschbaum |
| 2009/0193250 A1 | 7/2009 | Yokota et al. |
| 2009/0205026 A1 | 8/2009 | Haff et al. |
| 2009/0210724 A1 | 8/2009 | Hori |
| 2009/0240941 A1 | 9/2009 | Lee et al. |
| 2009/0245515 A1 | 10/2009 | Bond et al. |
| 2009/0287837 A1 | 11/2009 | Felsher |
| 2009/0293116 A1 | 11/2009 | DeMello et al. |
| 2010/0011410 A1 | 1/2010 | Liu |
| 2010/0017593 A1 | 1/2010 | Putz |
| 2010/0031025 A1 | 2/2010 | Zhang et al. |
| 2010/0088320 A1 | 4/2010 | Fortier et al. |
| 2010/0098256 A1 | 4/2010 | Kirshenbaum |
| 2010/0131296 A1 | 5/2010 | Knutson |
| 2010/0138655 A1 | 6/2010 | Matsui et al. |
| 2010/0191975 A1 | 7/2010 | Chase et al. |
| 2010/0208895 A1 | 8/2010 | Boneh et al. |
| 2010/0250937 A1 | 9/2010 | Blomquist et al. |
| 2010/0280333 A1 * | 11/2010 | Parshuram et al. ............ 600/301 |
| 2011/0004513 A1 | 1/2011 | Hoffberg |
| 2011/0072142 A1 | 3/2011 | Herz et al. |
| 2011/0123027 A1 | 5/2011 | Gotthardt |
| 2011/0150212 A1 | 6/2011 | Spalka et al. |
| 2011/0154044 A1 | 6/2011 | Spalka et al. |
| 2011/0173455 A1 | 7/2011 | Spalka et al. |
| 2011/0179286 A1 | 7/2011 | Spalka et al. |
| 2011/0185178 A1 | 7/2011 | Gotthardt |
| 2011/0185188 A1 | 7/2011 | Spalka et al. |
| 2011/0191590 A1 | 8/2011 | Darbellay et al. |
| 2011/0225114 A1 | 9/2011 | Gotthardt |
| 2011/0268269 A1 | 11/2011 | Spalka et al. |
| 2011/0307961 A1 | 12/2011 | de Perthuis |
| 2012/0063592 A1 | 3/2012 | Spalka et al. |
| 2012/0063594 A1 | 3/2012 | Spalka et al. |
| 2012/0087494 A1 | 4/2012 | Spalka et al. |
| 2013/0179176 A1 | 7/2013 | Gotthardt |

FOREIGN PATENT DOCUMENTS

| | | |
|---|---|---|
| DE | 102004044892 A1 | 3/2006 |
| DE | 102004051296 B3 | 5/2006 |
| DE | 102004063962 A1 | 6/2006 |
| DE | 102006057201 A1 | 6/2008 |
| EP | 0334616 A2 | 9/1989 |
| EP | 1411514 A2 | 4/2004 |
| EP | 1657847 A1 | 5/2006 |
| EP | 1890270 A1 | 2/2008 |
| WO | WO 99/14652 A1 | 3/1999 |
| WO | WO 99/33222 A1 | 7/1999 |

(56) References Cited

FOREIGN PATENT DOCUMENTS

| WO | WO 00/41613 A2 | 7/2000 |
| --- | --- | --- |
| WO | WO 00/54125 A1 | 9/2000 |
| WO | WO 00/72504 A1 | 11/2000 |
| WO | WO 01/69513 A2 | 9/2001 |
| WO | WO 02/05061 A2 | 1/2002 |
| WO | WO 02/09580 A1 | 2/2002 |
| WO | WO 2007/031955 A2 | 3/2007 |
| WO | WO 2007/091002 A1 | 8/2007 |
| WO | WO 2008/059475 A1 | 5/2008 |
| WO | WO 2008/085881 A1 | 7/2008 |
| WO | WO 2009/121657 A1 | 10/2009 |

OTHER PUBLICATIONS

"Elliptic Curve Cryptography", Technical Guideline TR-01111; Apr. 17, 2009, XP55011255, version 1.11; retrieved from the Internet Nov. 4, 2011: <<https://www.bsi.bund.de/SharedDocs/Downloads/DE/BSI/Publikationen/TechnischeRich tlinien/TR03111/BSI-TR-03111_pdf.pdf?_blo b=publicationFile>>, 33 pages.

Arokiaraj, A. Rex Macedo et al., "ACS: An Efficient Address Based Cryptography Scheme for Mobile Ad Hoc Networks Security", IEEE International Conference on Computer and Communication Engineering, 2008, Piscataway, NJ, USA, May 13, 2008, pp. 52-56, XP031292749, ISBN: 978-1-4244-1691-2.

Atallah, Mikhail J., et al., "Dynamic and Efficient Key Management for Access Hierarchies," Proceedings of the 12th ACM Conference on Computer and Communications Security, Alexandria, VA, Nov. 7-11, 2005; 12 pages.

Benjumea et al., "Anonymous Attribute Certificates Based on Traceable Signatures," Internet Research, vol. 16, No. 2, Jan. 2006, pp. 120-139.

Bresson, Emmanuel et al., "Dynamic Group Diffie-Hellman Key Exchange under Standard Assumptions," IACR 2002, 16 pages.

Camenisch, J. et al., "How to Win the Clone Wars: Efficient Periodic n-Times Anonymous Authentication," CCS '06, Oct. 30-Nov. 3, 2006, Alexandria, VA; Copyright 2006 ACM; 1-59593-518-5/06/0010; pp. 201-210.

Chao, Gao, "Study on Privacy Protection and Anonymous Communication in Peer-to-Peer Networks", IEEE 2009 International Conference on Multimedia Information Networking and Security, Piscataway, NJ, USA, Nov. 18, 2009, pp. 522-525, XP031592182, ISBN: 978-0-7695-3843-3.

Chothia, Tom et al., "Securing Pseudo Identities in an Anonymous Peer-to-Peer File-Sharing Network," IEEE Third International Conference on Security and Privacy in Communications Networks and the Workshops, 2007, Piscataway, NJ, USA, Sep. 17, 2007, pp. 279-282, XP031276557, ISBN: 978-1-4244-0974-7.

Chung, Y.F., et al. "Access Control in User Hierarchy Based on Elliptic Curve Cryptosystem," Science Direct Information Sciences, Amsterdam, NL LNKD- DOI:10.1016/L.INS.2007.08.001, Bd. 178, Nr. 1; Oct. 9, 2007, pp. 230-243, XP022289858 ISSN: 0020-0255.

Gudes, Ehud "The Design of a Cryptography Based Secure File System," IEEE Transactions on Software Engineering, vol. 6, No. 5, Sep. 1980, pp. 411-420, XP007912572.

Guinee, R. et al., "A Novel True Random Binary Sequence Generator Based on A Chaotic Double Scroll Oscillator Combination with a Pseudo Random Generator for Cryptographic Applications", 2009, IEEE Internet Technology and Secured Transactions, Nov. 9-12, 2009; ISBN: 978-1-4244-5647-5; 6 pages.

Hengartner, U. et al., "Exploiting Hierarchical Identity-Based Encryption for Access Control to Pervasive Computing Information," IEEE Proceedings of the First International Conference on Security and Privacy for Emerging Areas in Communications Networks, ISBN 0-7695-2369-2/05, 2005, 10 pages.

Hoffstein, et al., "An Introduction to Mathematical Cryptography," 2008 Spring Scient Busniess Media, LLC; ISBN 978-0-387-77993-5, pp. 60-61.

Jeng, Fuh-Gwo et al: "A practical and dynamic key management scheme for a user hierarchy", Journal of Zhejiang University Science A; An International Applied Physics & Engineering Journal, Springer, Berlin, DE, vol. 7, No. 3, Mar. 1, 2006, pp. 296-301, XP019360969, ISSN: 1862-1775, DOI: 10.1631/JZUS.2006.A0296.

Kuo, F.H. et al., "Cryptographic key assignment scheme for dynamic access control in a user hierarchy," IEEE Proceedings—Computers and Digital Techniques, vol. 146, No. 5, Sep. 1999, pp. 235-240, XP006013180 ISSN: 1350-2387.

Lin, Y. et al. "Digital Signature Systems Based on Smartcard and Fingerprint Feature," Journal of Systems Engineering and Electronics, vol. 18, No. 4, 2007, received Aug. 10, 2006, pp. 825-834.

Menezes, A. et al., "Chapter 12: Key Establishment Protocols ED", Handbook of Applied Cryptography; [CRC Press Series on Discrete Mathematices and Its Applications], CRC Press, Boca Raton, FL, US, pp. 489-541, Oct. 1, 1996, XP001525012, ISBN: 978-0-8493-8523-0 Retrieved from the Internet: URL:http://www.cacr.math.uwaterloo.ca/hac/.

Menezes, A. et al., "Chapter 13: Key Management Techniques ED", Handbook of Applied Cryptography; [CRC Press Series on Discrete Mathematices and Its Applications], CRC Press, Boca Raton, FL, US, pp. 543-590, Oct. 1, 1996, XP001525013, ISBN: 978-0-8493-8523-0 Retrieved from the Internet: URL:http://www.cacr.math.uwaterloo.ca/hac/.

Menezes, A. et al., "Chapter 8: Public-Key Encryption ED", Handbook of Applied Cryptography; [CRC Press Series on Discrete Mathematices and Its Applications], CRC Press, Boca Raton, FL, US, pp. 283-319, Oct. 1, 1996, XP001525008, ISBN: 978-0-8493-8523-0 Retrieved from the Internet: URL:http://www.cacr.math.uwaterloo.ca/hac/.

Montenegro, G. et al., "Statistically Unique and Cryptographically Verifiable Identifiers and Addresses", 5. JCT-VC Meeting; 96. MPEG Meeting; Mar. 16-Mar. 23, 2011; Geneva;(Joint Collaborative Team on Video Coding of ISO/IEC JTC1/SC29/WG11AND ITU-T SG.16); URL: Http://WFTP3.ItU.INT/AV-ARCH/JC TVC-SITE/—Mar. 17, 2011, Internet Engineering Task Force, IETF, Apr. 1, 2001, XP015032660, ISSN: 0000-0004, 13 pages.

Musen, M.A. et al., "Clinical Decision-Support Systems," from "Biomedical Informatics: Computer Applications in Health Care and Biomedicine," May 25, 2006, New York, NY, pp. 698-736.

Nadehara, K. et al. "Extended Instructions for the AES Cryptography and their Efficient Implementation", 2004, IEEE Workshop on Signal Processing Systems, Oct. 13-15, 2004; pp. 152-157.

Rankl, W. et al., "Smart Card Handbook, Third Edition" 1999, John Wiley & Sons, Ltd., ISBN: 0-470-85668-8, pp. 51,187-203, 222-244, 397-433, 441-442, 457-465.

Rare Diseases Act, Nov. 6, 2002, Public Law 107-280, 107th Congress, 5 pages.

Sandhu, R. S., "On Some Cryptographic Solutions for Access Control in a Tree Hierarchy," Proceedings 1987 Fall Joint Computer Conference on Exploring Technology: Today and Tomorrow; (CAT. NO.87CH2468-7) IEEE Computer Socienty, 1987, pp. 405-410, XP007912584 ISBN: 0-8186-0811-0.

Schneider, F.B. et al., "Implementing Trustworthy Services Using Replicated State Machines", IEEE Computer Society, IEEE Security & Privacy; vol. 3, issue 5; ISSN: 1540-7993/05; Sep.-Oct. 2005, pp. 34-43.

Shamir, A: "Identity-Based Cryptosystems and Signature Schemes," Lecture Notes in Computer Science/MICCAI 2000, Springer, DE; Jan. 1, 1985, pp. 47-53, XP000675444, DOI: 10.1007/3-540-39568-7_5 ISBN: 978-3-540-24128-7.

Waters, B R et al., "Receiver Anonymity via Incomparable Public Keys," Proceedings of the 10th ACM Conference on Computer and Communications Security; Washington D.C., USA, vol. CONF. 10, Oct. 27, 2003, XP002361168, DOI: 10.1145/948109.948127 ISBN: 978-1-58113-738-5; 10 pages.

Zhang, Yang, "An Efficient Anonymous Authentication Protocol with Pseudonym Revocability", 2009 Fifth International Joint Conference on INC, IMS and IDC; IEEE Computer Society; Aug. 25, 2009, pp. 1929-1934, XP031564722, ISBN: 978-0-7695-3769-6.

* cited by examiner

```
<data>
    <personal_data>
        <name> ... </name>
        <street> ... </street>
        <zip_code> ... </zip_code>
    </personal_data>
    <medical_data>
        <biometric>
            <age> ... </age>
            <gender> ... </gender>
            <bmi>
                <entry>
                    <value> ... </value>
                    <timestamp> ... </timestamp>
                </entry>
                <entry>
                    <value> ... </value>
                    <timestamp> ... </timestamp>     ─── 951
                </entry>
            </bmi>
            <gender> ... </gender>
            <...> ... </...>
        </biometric>
        <laboratory_values>
            <glucose>
                <entry>
                    <value> ... </value>
                    <timestamp> ... </timestamp>
                </entry>
                <entry>
                    <value> ... </value>
                    <timestamp> ... </timestamp>
                </entry>
            </glucose>
            <ldl>
                <entry>
                    <value> ... </value>
                    <timestamp> ... </timestamp>
                </entry>
            </ldl>
            <...> ... </...>
        </laboratory_values>
    </medical_data>
</data>
```
⎫
⎬ 950
⎭

Figure 9

DATA STRUCTURE, METHOD, AND SYSTEM FOR PREDICTING MEDICAL CONDITIONS

FIELD OF THE INVENTION

The present invention relates to the field of data processing, and more particularly to a data-structure, computer implemented method and computer system for predicting medical conditions and for methods for specifying and instantiating said data structure.

BACKGROUND AND RELATED ART

Decision support systems (DSS) are computer-based information systems for supporting decision making activities. They are widely used in various medical contexts, e.g. in biomedical research and diagnostics and in particular in the health care sector where DSSs are used for automatically determining the current health status of a patient given a set of input parameter values and/or for predicting medical conditions.

Various decision support systems exist which differ regarding the input parameters and/or the algorithmic approach used for calculating a decision, regarding the software architecture and regarding the output returned by a DSS. A DSS may assist a medical practitioner, e.g. a physician in a hospital or in a medical practice, in taking a decision by providing probability values for one or more possible diagnoses and/or or may return a comprehensive diagnosis including suggestions for surgical treatment and medication.

US 2008/0263050 describes a computer-implemented method for managing data for a clinical decision support system. The decision support system includes a plurality of rules.

The medical information decision support system disclosed in US 2002/0091687 A1 is also based on the usage of rules. According to said system, a decision generator determines options for providing medical service to patients based on information received from an information/directives repository, an adaptive chart and input from a user. Said information/directives repository comprises e.g. clinical practice guidelines, formulary statements, algorithms, protocols, care-maps and differential diagnosis trees.

Rule-based DSS, but also DSS based on other algorithms such as decision trees, Bayesian networks, clustering and other machine learning techniques commonly face the problem that they are highly specialized on a small set of possible diagnoses. They are expert systems for a highly specialized field, used by a small group of specialists and are not suited for usage e.g. in a family doctor's practice or a hospital where a multitude of different diseases are treated.

Medical DSSs with a more general scope are hampered by the fact that they require a multitude of patient related data in order to perform a prediction. Often, it is not possible to obtain this data: in an emergency case, there may not be enough time for obtaining the totality of data required by a DSS. A family doctor's practice may not comprise all devices necessary to obtain the multitude of data values required as input for medical DSS with a general predictive scope.

A further problem associated with the large number of biomedical parameters current DSSs require as input is, that the computational costs of predicting a medical condition by a DSS often grow at a non-linear, e.g. exponential, pace with a growing number of input parameters. Accordingly, DSSs with a general scope requiring a multitude of input parameters to ensure an acceptable accuracy level and coverage of the prediction tend to be slow and computationally expensive. Accordingly, working with such DSSs tends to be slow and can be highly uncomfortable, especially if the DSS is installed on hardware with limited computational power, e.g. old computers, netbooks, mobile phones and other mobile devices.

The objective of embodiments of the present invention is to provide for an improved decision support system, in particular an improved remote decision support system.

SUMMARY OF THE INVENTION

The invention provides for a data structure, a method for specifying said data structure, a method for instantiating said data structure, a computer system and a computer-readable storage medium as specified in the independent claims. Embodiments are given in the dependent claims.

Embodiments of the invention provide for a data structure being particularly suited to be used as input of a decision support system, in particular a remote decision support system. Further embodiments provide for methods for specifying and instantiating said data structure and for corresponding computer systems and computer-readable storage devices.

According to one beneficial aspect, embodiments of the invention provide for a data structure which minimizes computational costs associated with predicting a medical decision, whereby said data structure at the same time allows for a predictive coverage of the prediction algorithm used by a DSS.

According to a further beneficial aspect, embodiments of the invention provide for a data structure which minimizes the computational costs and data storage space required to provide a DSS system with biomedical parameter values of a patient. As a result, a remote medical decision system is provided covering the majority of medical conditions currently diagnosed and treated in a general doctor's practice or hospital in modern industrialized countries.

According to a further beneficial aspect, embodiments of the invention provide for a solution to the problem that decision support systems hosted on a server can often not be used by a client application dynamically. A dynamic usage of a software implies that the results of an operation of said software are received almost immediately, thereby allowing the usage of said software by a user without interruptions and distracting time delays. A dynamic use of a remote DSS by a client software being interoperable with said remote DSS is often made impossible by slow network connections and time consuming processing steps executed by the remote DSS. Data structures according to embodiments of the invention solve said problem by providing a data structure of minimum size, comprising biomedical parameters providing maximum coverage of the most common diseases of a population, thereby reducing network traffic and computational costs at the same time.

According to a further beneficial aspect, embodiments of the invention allow the flexible mapping of medical parameter values of a patient having been stored according to an outdated and/or non-standardized system of units and/or non-standardized catalog into biomedical parameters of a desired standard, e.g. the LOINC standard, whereby said mapping can be executed also by users who are not familiar with writing a parser program.

According to a further beneficial aspect, embodiments of the invention provide for a method which allows providing data obtained from a multitude of different data sources to a multitude of different DSS systems or DSS system modules.

According to a further beneficial aspect, embodiments of the invention provide for a DSS which is operable to cover the majority of medical conditions currently diagnosed and treated in a general doctor's practice or hospital e.g. in modern industrialized countries, whereby said DSS is operable to accurately calculate medical decisions based on a data structure of minimal size, said DSS therefore being particularly suited to be used as remote DSS on a server providing medical decisions to multiple clients.

According to a further beneficial aspect, embodiments of the invention provide for a modular DSS which can easily be maintained by dynamically adding, removing or exchanging any of its modules.

The term 'predictive accuracy' or 'accuracy' as used herein denotes a measure for the quality and reliability of a prediction of a medical condition calculated by a medical DSS. The accuracy can be, depending on the used algorithm, calculated e.g. as the ratio of true positive and negative predictions and the sum of all positive and negative data values contained in a data set: (TP+TN)/(TP+TN+FP+FN), wherein 'TP' is a 'true positive result', 'FP' is a 'false positive result', 'TN' is a 'true negative result', and 'FN' is a 'false negative result'.

The expression 'biomechanical disease' encompasses any disease whose present or future occurrence in a patient cannot be encoded or described by means of a set of metric, ordinal or nominal parameters. The size of said set is typically small. According to embodiments, parameter sets comprising 20 or fewer parameters are considered as small. A typical example for a biomechanical disease is a bone fracture which is preferentially diagnosed and described by means of x-ray images and/or natural language text. A bone fracture is typically not described or diagnosed by means of laboratory parameters such as parameters obtained from a blood analysis. Natural language text is hard to evaluate and process automatically due to the tremendous diversity of syntactically correct expressions which can be used (and are used in practice) to describe a particular semantic concept, e.g. a symptom). Diseases or medically relevant conditions which can be characterized by means of a limited set of nominal or ordinal data values such as 'smoker', 'non-smoker', 'small', 'medium' or 'high' are not considered as 'biomechanical diseases'. The term biomechanical disease as used herein also comprises causes of doctoral visits which are obvious and for which no diagnostic predictions or decisions are required. For example, if a patient explicitly requests for an immunization in preparation of a travel to a risk region, said request for vaccination causing a doctoral visit is also referred to as 'biomechanical disease'.

Data can be represented in various forms. Not every form may be, however, be appropriate for automated data processing and for transfer over a network of limited bandwidth. The size of an image is typically much larger than a set of metric, ordinal or nominal data values. Accordingly, image data, large sections of natural language text, audio data and the like have been found to be less appropriate for a distributed online decision support system than a limited set of nominal, ordinal or metric data values.

A nominal scale classifies or categorizes object attributes. An example of this would be the classification in 'male' and 'female'. A nominal scale doesn't allow for comparison to be made or mathematical operations to be performed. An ordinal scale is similar to the nominal scale. It differs from nominal scale in that categories can be ordered and comparisons can be made. A metric scale is used to express numerical data values, for example measurement values derived from a laboratory analysis. A metric data value can be ordered, can be compared to other metric data values and can be subject to mathematical calculations.

The term 'timestamp' encompasses information on the date and, according to embodiments, also on the time when a parameter value was specified, created, measured or the like. For example, if a measurement value is received from a lab device, said measurement value can be stored in association with a timestamp value, said timestamp value being indicative of the time and date of measuring the measurement value, of receiving the measurement value from the lab device or of storing said measurement value to a storage medium.

The term 'decision support system' (DSS), also referred to herein as 'analytic system', will in the following refer to any monolithic or distributed software- or hardware module taking one or more data values as input for providing one or more medical decisions as output. A medical decision can be, for example, the steering of a therapy, the provision of a user with a diagnosis for one or more diseases, the calculation of the risk to develop one or more diseases in the future, the suggestion of the appropriate medication and the like.

The term 'rule' as used herein is a computer-interpretable statement with two parts: an if-clause and a then-clause, whereby the then-clause is only executed in case the if-clause returns the Boolean value 'true'.

The term 'user-selected secret' is understood herein as any secret data that is selected by or related to a user, such as a user-selected secret password or a secret key, such as a symmetric cryptographic key. Further, the term 'user-selected secret' does also encompass a combination of biometric data obtained from the user and a user-selected password or secret key, such as a biometric hash value of the password or secret key.

The term 'embedding function' or 'embedding component' as used herein encompasses any injective function that maps the elements of an n-dimensional space onto elements of an m-dimensional space, where n>m. For the purpose of this invention, we focus on embedding functions where m=1. In accordance with embodiments of this invention n is equal to 2 and m is equal to 1 for combining two elements onto a single element. In one embodiment, a user-selected secret and a public parameter are mapped by the embedding function to the 1-dimensional space to provide a combination of the user selected secret and the public parameter, e.g. a single number that embeds the user selected secret and the public parameter. This single number constitutes the embedded secret. In another embodiment, a first hash value of the user selected secret and a random number are mapped by the embedding function to the 1-dimensional space to provide the embedded secret.

A 'randomizing function' or 'randomizing component' as understood herein encompasses any injective function that provides an output of data values that are located within a predefined interval and wherein the distribution of the data values within the predefined interval is a substantially uniform distribution.

The term 'embedding and randomizing function' as used herein encompasses any function that implements both an embedding function and a randomizing function.

The term 'computer readable storage medium' as used herein encompasses any storage medium which may store instructions which are executable by a processor of a computing device. In some embodiments, a computer readable storage medium may also be able to store data which is able to be accessed by the processor of the computing device. An example of a computer readable storage medium include, but are not limited to: a floppy disk, a magnetic hard disk drive, a solid state hard disk, flash memory, a USB thumb drive, Random Access Memory (RAM) memory, Read Only Memory (ROM) memory, an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example data may be retrieved over a modem, over the internet, or over a local area network.

The term 'computer memory' or 'memory' as used herein encompasses a computer readable storage medium or a plurality of computer readable storage media which is/are directly accessible to a processor. Examples of computer memory include, but are not limited to: RAM memory, registers, and register files of a processor.

The term 'computing device' as used herein encompasses any device comprising a processor. The term 'processor' as used herein encompasses any electronic component which is able to execute a program or machine executable instructions. References to the computing device comprising "a processor" should be interpreted as possibly containing more than one processor. The term 'computing device' should also be interpreted to possibly refer to a collection or network of computing devices each comprising a processor. Many programs have their instructions performed by multiple processors that may be within the same computing device or which may be even distributed across multiple computing device. The term 'computer system' may be interpreted herein as being a 'computing device.'

The term 'server' as used herein is a computing device providing one or more services to another computing device, the client, over a network.

The term 'database' as used herein is a collection of logically-related data or files containing data that provide data for at least one use or function. Databases are essentially organized data that may be provided or used by an application. Examples of a database include, but are not limited to: a relational database, a file containing data, a folder containing individual data files, and a collection of computer files containing data.

The term 'access key' as used herein is data or a character string which is used to provide read and/or write access to a database. In some embodiments the access key may be a reference used for identifying or locating data in the database. For example, in some embodiments an access key may be a pseudonym. The pseudonym allows identification of the ownership of various records. In other embodiments an access key may be a password or user identification. In other embodiments the access key may identify a record or records within the database. Records may be individual data files or they may be a collection of data files. An access key may be a primary key for a relation in a database. An access key may also be a unique key for a relation in a relational database.

The term 'parameter' as used herein is a formal placeholder for a data value of a particular type. A parameter has, in the context of its usage, e.g. in a computer program or program part or as part of a data structure stored to a storage medium, a unique 'name' or 'identifier'. For example, a parameter given the name 'glucose concentration' is a biomedical parameter which may have assigned a particular parameter value, e.g. the glucose concentration having been measured for a particular patient. Depending on the parameter, a parameter may have assigned additional pieces of information such as units of measurements, e.g. g/ml or mmol/l, data on the source of the parameter value, e.g. 'blood' or 'urine' or the like. A parameter as used herein may also have assigned multiple parameter values at the same time. The parameter 'allergies', for example, may have assigned the parameter value 'pollen allergy' and 'strawberry allergy'. According to embodiments of the invention, a parameter value can have assigned a timestamp value.

The term 'catalog' refers to structured data stored in a data storage. A catalog comprises data objects representing various semantic concepts. A catalog comprises a specification of the semantic relations between the elements of a catalog. A catalog can be, for example, a biomedical thesaurus or ontology. In particular, the elements of a catalog can be ordered hierarchically based, e.g. on 'belongs-to' relations. For example, a biomedical catalog may comprise a hierarchical organization of diseases, drugs, allergies or the like.

In one aspect, the present invention provides for a data structure comprising a plurality of biomedical parameters which is operable to provide a plurality of biomedical parameter values as input to a medical decision support system. Said plurality of biomedical parameter values comprises a first set of parameter values, each parameter value of the first set of parameter values being a laboratory value having been derived by analyzing a body fluid or tissue of a person, the first set of parameter values consisting of:
  the glucose concentration,
  the LDL concentration,
  the HDL concentration,
  the triglyceride concentration,
  the creatinine concentration,
  the cholesterol concentration,
  the Hba1c concentration, and
  the CRP concentration,
  whereby the plurality of parameter values comprises a second set of parameter values, the second set of data values consisting of:
  the age,
  the gender,
  the body mass index BMI,
  the waist/hip ratio,
  the blood pressure, and
  the smoking history.

Said data structure is also referred to as 'data structure I' or 'data structure variant I' and comprises parameter set I.

Depending on the embodiment of the invention, the body fluid or tissue can be, for example, blood or urine.

According to further embodiments, the first set of parameter values further comprises the following biomedical parameters:
  the International Normalized Ratio INR,
  the potassium concentration, and
  the TSH concentration.

Said data structure is also referred to as 'data structure II' or 'data structure variant II' and comprises parameter set II. Parameter set I is a subset of parameter set II.

According to further embodiments, the above mentioned first set of parameter values further comprises:
  the gamma-glutamyltransferase concentration,
  the alanine transaminase concentration, and
  the hemoglobin concentration.

Said data structure is also referred to as 'data structure III' or 'data structure variant III' and comprises parameter set III.

According to further embodiments, the above mentioned first set of parameter values further comprises the
  Leukocyte concentration,
  Albumin concentration, and
  Hämohapto value Stool,
  and the second set of parameter values further comprises:
  body height,
  body weight, body temperature,
hip circumference,
waist circumference,
the systolic blood pressure,
the mean blood pressure,
the diastolic blood pressure,
the pulse rate,
allergies and intolerances, and
the medication history of the person.

Said data structure is also referred to as 'data structure III' or 'data structure variant IV' and comprises parameter set IV.

According to further embodiments, the above mentioned second set of parameter values of parameter set I further comprises the ethnicity of the person. Said embodiments are particularly advantageous in ethnically mixed populations such as the US population.

According to further embodiments, the above mentioned second set of parameter values further comprises pregnancies and lactation times of a person.

According to further embodiments, at least one parameter value of the plurality of parameter values has assigned at least one timestamp value, the at least one timestamp value being indicative of the time and date of having received, specified or measured the data value. For example, a biomedical parameter 'glucose level' may have assigned 10 biomedical parameter values having been derived by 10 blood analyses of the patient. Each of said measurement values may have assigned a timestamp value comprising at least the date and, according to embodiments, also a time information being indicative of the moment of measurement, of entering said measurement value in a computer, or the like.

In a further aspect, the invention provides for a computer-implemented method for generating a specification of a data structure of one of the above embodiments. Said data structure comprises a plurality of biomedical parameters and can be used as input for a medical decision support system. The method for specifying said data structure comprises:

determining, for a particular population of persons, a first set of diseases, each disease being represented by a data object, whereby each disease belonging to the determined set of diseases has assigned an absolute or relative frequency within said population; according to preferred embodiments, the first set of diseases comprises the most frequently occurring diseases of said population, whereby a 'disease' may also be a group of related diseases, storing each data object representing a disease of the first set of diseases in association with the determined frequency value of the represented disease, sorting the diseases of the first set of disease according to their assigned frequency values, determining a second set of diseases, whereby the second set of diseases is a sub-set of the first set of diseases, the sub-set being created by leaving out all diseases of the first set of diseases which are biomechanical diseases, determining a third set of diseases, the third set of diseases being built by executing the sub-steps:
A) determining, for each disease of the second set of diseases, the number of predictive parameters,
B) assigning a score value to each disease, the score value positively correlating with the frequency value of a disease and negatively correlating with the number of parameters correlating with or characterizing said disease, and sorting the diseases of the second set of diseases according to their assigned score values,
C) adding a disease of the second set of diseases which has assigned the highest score value and which in addition has not yet been added to the third set of diseases to the third set of diseases,
D) calculating a first sum, the first sum being calculated by summing up all frequency values of the diseases having yet being added to the third set of diseases,
E) if the first sum is below a coverage threshold value, repeating steps C and D, and if the first sum equals or exceeds said coverage threshold value, continuing with step F and using the third set of diseases and the first sum as result, and
F) compiling a plurality of biomedical parameters by determining, for each of the diseases in the third set of diseases, at least one biomedical parameter being indicative of the presence of said disease, whereby the compilation of the biomedical parameters constitutes the specification of the data structure.

According to embodiments of the invention, the predictive parameters determined in step A for a particular disease are metric, ordinal or nominal parameters which are known to correlate with a particular disease, being indicative of a disease, cause a disease, or being the result of a disease.

According to further embodiments, said method further comprises the steps of instantiating the specified data structure by assigning each biomedical parameter of the data structure at least one biomedical data value of a person.

According to further embodiments, said method further comprises the steps of adding, to each biomedical parameter being a biometric parameter a timestamp value, the timestamp value being indicative of the date or time and date the data value was received, measured, stored or created.

In a further aspect, the invention relates to a method for instantiating a data structure according to any of the above embodiments, wherein each biomedical parameter of the data structure is assigned one or more parameter values.

According to some embodiments of the invention, said functionality is provided by a data structure instantiation module (DSI module). The DSI module can be installed on any processing device, in particular a client device such as a computer of a physician. According to some embodiments, the DSI module is interoperable with a doctor information system DIS and/or a decision support system DSS. A DSI module being interoperable with the DIS system facilitates, together with functions provided by the DIS system, to enter patient-related data values and to instantiate a data structure based on said data values. The instantiated data structure can be submitted to the DSS for calculating a medical decision.

A doctor information system is a computer-based information storage, retrieval, and analysis system for managing patient-related data. Doctor information systems typically provide a physician or medical secretaries with means to enter or edit patient-related data, e.g. the patient's address and/or the medical history of the patient.

According to further embodiments, the DIS module is interoperable with a communication module. The communication module is interoperable with a doctor information system and with the DSS system. The communication module is operable to receive an instantiated data structure from the DSI module or from the DIS system and is operable to send the instantiated data structure to a DSS. Upon receipt of a medical decision calculated by the DSS, the communication module is operable to trigger and specify the display of messages to a user via a GUI. Said messages are displayed, according to preferred embodiments of the invention, as popup message.

According to some embodiments, the DIS module further comprises computer-implemented instructions encoding a method for instantiating a data structure wherein at least one biomedical parameter of the data structure is assigned a parameter value by executing the steps: at first, one or more hierarchical, biomedical catalogs are received, e.g. by reading a file comprising said catalog from a storage medium, by accessing a database or by receiving said catalogs via a network connection. Each element of the catalog is represented as node of a tree. In the next step, on a graphical user interface the nodes of the tree are presented to a user, e.g. a physician. Accordingly, each tree node of the tree is a graphical representation of the catalog element of the received biomedical catalog. The GUI allows the user to navigate downwards or upwards in the tree structure. Upon selection of a tree node by the user, information being indicative of the catalog element represented by the selected tree node is displayed. The name or identifier of the indicated catalog element is assigned to a parameter value to a biomedical parameter. For example, the catalog received can be an ontology of allergies. Upon selection of the node 'strawberry allergy', said identifier is assigned as parameter value to the biomedical parameter 'allergies'.

According to embodiments, the DSI module or another software module provides a user not skilled in a programming language to map laboratory values received from a variety of different laboratories which may completely or partially be encoded in a non-standard format to a desired standard, e.g. LOINC. Some laboratories use identifiers for laboratory values which may deviate from the standards used outside the lab. For example, a laboratory analyzing biological samples or a physician specifying a patient record manually may use the acronym 'Krea' for Kreatinine while other laboratories may use 'Crea' or 'C' as parameter name for Kreatinine. The diversity of parameter identifiers used in many labs is often disadvantageous, as the doctor information system and/or DSS used by a physician may only be able to interpret laboratory values encoded according to a particular standard, e.g. LOINC, correctly. As a consequence, the physician is tied to one particular analysis service provider and may be unable to use analysis results provided by other laboratories. The DSI module provides a user not skilled in a programming language to map a broad range of parameters to a particular standard by means of a GUI, provided the laboratory values are provided in the form of a standard data format such as XML, CSV or the like. Said functionality is, according to embodiments, integral part of the DSI module or any other software module involved in the instantiation of a data structure for a particular patient. According to said embodiments of the invention, for instantiating a data structure and for assigning to at least one biomedical parameter of said data structure a biomedical parameter value, the following method steps are executed:

At first, a plurality of biomedical parameters, e.g. laboratory parameters, is received. On a graphical user interface, a first list of selectable GUI elements is displayed, whereby each selectable GUI element represents a laboratory parameter belonging to the plurality of received parameter values. Upon selection of a laboratory parameter of the first list by a user, a list of second parameter names is presented to a user for selection in a second list of selectable GUI elements. Each second parameter name of a selected GUI element representing a biomedical parameter of the first list is determined automatically, e.g. via a comparison of the first characters of the selected parameter and identifiers belonging to the desired standard or 'output standard'. For example, any parameter name in the first list starting with 'Kr' may be a candidate for suggesting 'Kreatinine' in the second list. In addition, or alternatively, a mapping may be used which maps a set of commonly used biomedical parameter names to names or identifiers of the desired standard. For example, the parameter name 'Crea' may be mapped to the parameter name 'Kreatinine' and 'Kreatinine' may be displayed in the second list upon selection of the 'Crea' element in the first list. Each second parameter name is automatically determined and represented as a selectable GUI element in the second list.

Depending on the desired standard to which the received parameter values are to be transformed, the GUI may provide additional GUI elements for specifying additional dimensions of said desired standard. According to one embodiment, the LOINC code schema is used as desired output standard. A LOINC code comprises 6 dimensions and the specification of each dimension contributes to a final LOINC code. According to embodiments according to which the multidimensional LOINC codes are the desired standard, the GUI further comprises first selectable GUI elements for selecting a LOINC method, second selectable GUI elements for selecting a system of units, third selectable GUI elements for selecting the tissue the selected laboratory parameter was derived from. The GUI further comprises a display element which dynamically displays a current LOINC code as derivative of the LOINC dimension already specified by a user (e.g. LOINC method, LOINC tissue, LOINC system of units).

Depending on the embodiment, the DSI and the DIS module may be hosted on the same computer system, e.g. a desktop computer system of a physician. Patient-related data is typically stored also in said computer system or on a central, remote data storage which is accessible by the DIS e.g. via a communication layer.

According to other embodiments, the DSI is operable to directly submit data structure instances to a remote decision support system and/or to a remote data repository for storing patient related data. The biomedical parameter values may be read from a patient's card or may be received from one or more laboratory devices by the DSI module and use said values for instantiating the data structure. The remote DSS may receive the instantiated data structure, calculate a decision and store said decision in association with the data structure to a data storage.

According to further embodiments, the DIS or at least some parts of it may also be hosted remotely on a server while the client computer system merely comprises program modules for receiving information for displaying a GUI and submitting interactions of the user with said GUI to said server. Said program modules may be a browser such as Firefox or Internet Explorer but may also be a piece of software having been developed to specifically interact with a remote DIS module. According to said embodiments, the remote DIS module may receive information required for instantiating a data structure and for submitting said data structure instance to another server hosting a decision support system.

Preferred Data Structures

In the following, four preferred data structures and the biomedical context of the parameters contained therein will be described.

Biomedical Parameters of Data Structures I-III

In the following, the biomedical parameters used for data structures I-III and corresponding to parameter sets I-III will be explained with reference to their respective biological and medical function.

Data structures I-III respectively comprise minimum biomedical parameter sets which can be used by a DSS to calculate a medical decision, whereby said parameter sets cover about 60%, 70% and 80% of the diseases diagnosed in doctor practices in Germany respectively. In the following tables, synonyms of a parameter name will be given in round brackets O and the preferred body fluid or tissue used for determining a biomedical parameter is given in square brackets [ ].

Data Structure I

| Biomedical Parameter | Explanation; Medical or Biological Function; |
|---|---|
| Age | Age of the patient |
| Gender | Gender of the patient |
| BMI (Body mass index) | The body mass index (BMI) is a statistical measure of body weight based on a person's weight and height. Though it does not actually measure the percentage of body fat, it is used to estimate a healthy body weight based on a person's height. |
| Waist/Hip ratio | Waist-hip ratio or Waist-to-hip ratio (WHR) is the ratio of the circumference of the waist to that of the hips. It is calculated by measuring the smallest circumference of the natural waist, usually just above the belly button, and dividing by the hip circumference at its widest part of the buttocks or hip. The ratio is applied both to women and men. |
| Blood pressure | |
| Smoking history | |
| CRP (C Reactive Peptide); [venous blood] | CRP is a member of the class of acute-phase reactants, as its levels rise dramatically during inflammatory processes occurring in the body. This increment is due to a rise in the plasma concentration of IL-6, which is produced predominantly by macrophages as well as adipocytes. Normal concentration in healthy human serum is usually lower than 10 mg/L, slightly increasing with ageing. Higher levels are found in late pregnant women, mild inflammation and viral infections (10-40 mg/L), active inflammation, bacterial infection (40-200 mg/L), severe bacterial infections and burns (>200 mg/L). Cardiology diagnostic test: Arterial damage results from white blood cell invasion and inflammation within the wall. CRP is a general marker for inflammation and infection, so it can be used as a very rough proxy for heart disease risk. Since many things can cause elevated CRP, this is not a very specific prognostic indicator. Nevertheless, a level above 2.4 mg/l has been associated with a doubled risk of a coronary event compared to levels below 1 mg/l (C-reactive protein: a critical update Mark B. Pepys, Gideon M. Hirschfield J. Clin. Invest. 2003; 111(12):1805); however, the study group in this case consisted of patients who had been diagnosed angina pectoris; whether elevated CRP has any predictive value of with unstableacute coronary events in the general population of all age ranges remains unclear. |
| Cholesterol (Chol) [venous blood] | Cholesterol is a waxy steroid metabolite found in the cell membranes and transported in the blood plasma of all animals. It is an essential structural component of mammalian cell membranes, where it is required to establish proper membrane permeability and fluidity. According to the lipid hypothesis, abnormal cholesterol levels (hypercholesterolemia)-that is, higher concentrations of LDL and lower concentrations of functional HDL-are strongly associated with cardiovascular disease because these promote atheroma development in arteries (atherosclerosis). This disease process leads to myocardial infarction (heart attack), stroke, and peripheral vascular disease. Since higher blood LDL, especially higher LDL particle concentrations and smaller LDL particle size, contribute to this process more than the cholesterol content of the LDL particles, LDL particles are often termed 'bad cholesterol' because they have been linked to atheroma formation. On the other hand, high concentrations of functional HDL, which can remove cholesterol from cells and atheroma, offer protection and are sometimes referred to as 'good cholesterol'. These balances are mostly genetically determined but can be changed by body build, medications, food choices, and other factors. |
| HDL (HDSc; TCHHDL; HDL-C; High density Lipoprotein cholesterol) [venous blood] | See above |
| LDL (LDLc; LDL-C; Low density lipoprotein cholesterol) [venous blood] | See above |
| Glucose (Glu; Gluc; Glucoseur; Glucose random; Glucose lab) [venous blood; capillary blood] | The blood sugar concentration or blood glucose level is the amount of glucose (sugar) present in the blood of a human or animal. Normally in mammals, the body maintains the blood glucose level at a reference range between about 3.6 and 5.8 mM (mmol/L, i.e., milli-moles/liter) (64.8 and 104.4 mg/dL). Blood glucose levels are tightly regulated as a part of metabolic homeostasis. Glucose is the primary source of energy for the body's cells, and blood lipids (in the form of fats and oils) are primarily a compact energy store. Glucose is transported from the intestines or liver to body cells via the bloodstream, and is made available for cell absorption via the hormone insulin, produced by the body primarily in the pancreas. The mean normal blood glucose level in humans is about 4 mM (4 mmol/L or 72 mg/dL, i.e. milligrams/deciliter); however, this level fluctuates throughout the day. Glucose levels are usually lowest in the morning, before the first meal of the day (termed 'the fasting level'), and rise after meals for an hour or two by a few grams. Blood sugar levels outside the normal range may be an indicator of a medical condition. A persistently high level is referred to as hyper-glycemia; low levels are referred to as hypoglycemia. Diabetes mellitus is characterized by persistent hyperglycemia from any of several causes, and is the most prominent disease related to failure of blood sugar regulation. A temporarily elevated blood sugar level may also result from severe stress, such as trauma, stroke, myocardial infarction, surgery, or illness. Intake of alcohol causes an initial surge in blood sugar, and later tends to cause levels to fall. Also, certain drugs can increase or decrease glucose levels. |
| Hba1c (glycosylated hemoglobin, hemoglobin A1c, HbA1c, A1C, or Hb1c; sometimes also HbA1c) [venous blood] | Glycated hemoglobin is a form of hemoglobin used primarily to identify the average plasma glucose concentration over prolonged periods of time. It is formed in a non-enzymatic pathway by hemoglobin's normal exposure to high plasma levels of glucose. Glycation of hemoglobin has been associated with cardiovascular disease, nephropathy, and retinopathy in diabetes mellitus. Monitoring the HbA1c in type-1 diabetic patients may improve treatment. The approximate mapping between HbA1c values and eAG (estimated average glucose) measurements is given by the following equation: eAG(mg/dl) = 28.7 × A1C − 46.7 eAG(mmol/l) = 1.59 × A1C − 2.59 |
| Creatinine (Crea; Creat; CR;) [urine; venous blood] | Creatinine (from the Greek κρέας, flesh) is a breakdown product of creatine phosphate in muscle, and is usually produced at a fairly constant rate by the body (depending on muscle mass). In chemical terms, creatinine is a spontaneously formed cyclic derivative of creatine. Creatinine is chiefly filtered out of the blood by the kidneys (glomerular filtration and proximal tubular secretion). There is little-to-no tubular reabsorption of creatinine. If the filtering of the kidney is deficient, blood levels rise. Therefore, creatinine levels in blood and urine may be used to calculate the creatinine clearance (CrCl), which reflects the glomerular filtration rate (GFR). The GFR |

| Biomedical Parameter | Explanation; Medical or Biological Function; |
|---|---|
| | is clinically important because it is a measurement of renal function. Measuring serum creatinine is a simple test and it is the most commonly used indicator of renal function. |
| Triglycerides (triacylglycerol, TAG; triacyl-glyceride; Trigl; TG; Trigly; Tri-glycerides; Trig; Triglycerides;) [venous blood] | Triglyceride is an ester derived from glycerol and three fatty acids. It is the main constituent of vegetable oil and animal fats. In the human body, high levels of triglycerides in the bloodstream have been linked to atherosclerosis, and, by extension, the risk of heart disease and stroke. However, the relative negative impact of raised levels of triglycerides compared to that of LDL/HDL ratios is as yet unknown. The risk can be partly accounted for by a strong inverse relationship between triglyceride level and HDL-cholesterol level.<br>Diets high in carbohydrates, with carbohydrates accounting for more than 60% of the total caloric intake, can increase triglyceride levels. Of note is how the correlation is stronger for those with higher BMI (28+) and insulin resistance (more common among overweight and obese) is a primary suspect cause of this phenomenon of carbohydrate-induced hypertriglyceridemia.<br>There is evidence that carbohydrate consumption causing a high glycemic index can cause insulin overproduction and increase tri-glyceride levels in women. |

According to some embodiments, the data structure variant I also comprises a parameter being indicative of the race or ethnicity of a patient. Said parameter is important in mixed populations like the USA, where race or ethnicity becomes important for choosing the right therapy or making a correct risk assessment.

Data Structure II

Data structure variant II comprises three biomedical parameters in addition to the parameters of data structure I.

| | |
|---|---|
| INR (International normalized ratio; PT INR; Prothrombin time INR; Protime INR; Pro time; International normal ratio; Internat norm ratio; International normalization ratio) [venous blood; capillary blood] | The prothrombin time (PT) and its derived measure international normalized ratio (INR) are measures of the extrinsic pathway of coagulation. They are used to determine the clotting tendency of blood, in the measure of warfarin dosage, liver damage, and vitamin K status.<br>The result (in seconds) for a prothrombin time performed on a normal individual will vary depending on what type of analytical system it is performed. This is due to the differences between different batches of manufacturer's tissue factor used in the reagent to perform the test. The INR was devised to standardize the results. |
| Potassium (K; K+; Potass; Kalium) [venous blood] | A severe shortage of potassium in body fluids may cause a potentially fatal condition known as hypokalemia. Hypokalemia typically results from loss of potassium through diarrhea, diuresis, or vomiting. Symptoms are related to alterations in membrane potential and cellular metabolism. Symptoms include muscle weakness and cramps, paralytic ileus, ECG abnormalities, intestinal paralysis, decreased reflex response and (in severe cases) respiratory paralysis, alkalosis and arrhythmia.<br>Extreme hyperkalemia is a medical emergency due to the risk of potentially fatal abnormal heart rhythms (arrhythmia). Symptoms are fairly nonspecific and generally include malaise, palpitations and muscle weakness; mild hyperventilation may indicate a compensatory response to metabolic acidosis, which is one of the possible causes of hyperkalemia. Often, however, the problem is detected during screening blood tests for a medical disorder, or it only comes to medical attention after complications have developed, such as cardiac arrhythmia or sudden death. INR and potassium are typical values for monitoring drug therapy. |
| TSH (Thyroid-stimulating hormone; Thyrotropic hormone; Thyroid stimulating hormone; TSE1) [venous blood] | TSH is a peptide hormone synthesized and secreted by thyrotrope cells in the anterior pituitary gland, which regulates the endocrine function of the thyroid gland. TSH levels are tested in the blood of patients suspected of suffering from excess (hyperthyroidism), or deficiency (hypothyroidism) of thyroid hormone.<br>About three percent of the general population is hypothyroid. Factors such as iodine deficiency or exposure to Iodine-131 can increase that risk. There are a number of causes for hypo-thyroidism. Iodine deficiency is the most common cause of hypothyroidism worldwide. In iodine-replete individuals hypothyroidism is generally caused by Hashimoto's thyroiditis, or otherwise as a result of either an absent thyroid gland or a deficiency in stimulating hormones from the hypothalamus or pituitary. Hyperthyroidism usually begins slowly. At first, the symptoms may be mistaken for simple nervousness due to stress. If one has been trying to lose weight by dieting, one may be pleased with weight loss success until the hyperthyroidism, which has quickened the weight loss, causes other problems. |

Data Structure III

Data structure variant III comprises further biomedical parameters in addition to the parameters of data structure II. The added parameters cover two parameters that can help in monitoring liver function. Hemoglobin gives information on the capability to transport oxygen and on homeostasis.

| | |
|---|---|
| Gamma glutamyl trans-peptidase (GGT; Gamma-GTP; GGTP; γGT, GGT, gamma-GT) [venous blood] | GGT has several uses as a diagnostic marker in medicine. Blood test results for GGT suggest that the upper limit of normal is around 40 to 78 U/L. Elevated serum GGT activity can be found in diseases of the liver, biliary system, and pancreas. In this respect, it is similar to alkaline phosphatase (ALP) in detecting disease of the biliary tract. Indeed, the two markers correlate well, though there is conflicting data about whether GGT has better sensitivity. In general, ALP is still the first test for biliary disease. The main value of GGT over ALP is in verifying that ALP elevations are, in fact, due to biliary disease; ALP can also be increased in certain bone diseases, but GGT is not. GGT is elevated by large quantities of alcohol ingestion. Isolated elevation or disproportionate elevation compared to other liver enzymes (such as ALP or ALT) may indicate alcohol abuse or alcoholic liver disease. It may indicate excess alcohol consumption up to 3 or 4 weeks prior to the test. The mechanism for this elevation is unclear. Alcohol may increase GGT production by inducing hepatic microsomal production, or it may cause the leakage of GGT from hepatocytes. |
| Alanine transaminase (ALT, GPT; SGPT; Glutamic-pyruvic transferase; Alanine transaminase; Ala; L-alanine; Alpha alanine) [venous blood] | It is commonly measured clinically as a part of a diagnostic liver function test, to determine liver health.<br>Significantly elevated levels of ALT often suggest the existence of other medical problems such as viral hepatitis, congestive heart failure, liver damage, bile duct problems, infectious mononucleosis, or myopathy. For this reason, ALT is commonly used as a way of screening for liver problems. |

| | -continued |
|---|---|
| | However, elevated levels of ALT do not automatically mean that medical problems exist. Fluctuation of ALT levels is normal over the course of the day, and ALT levels can also increase in response to strenuous physical exercise. |
| Hemoglobin (Hb; Hgb) [venous blood] | Hemoglobin (also spelled haemoglobin and abbreviated Hb or Hgb) is the iron-containing oxygen-transport metalloprotein in the red blood cells of vertebrates and the tissues of some invertebrates. Hemoglobin in the blood is what transports oxygen from the lungs or gills to the rest of the body (i.e. the tissues) where it releases the oxygen for cell use. High hemoglobin levels may be caused by exposure to high altitudes, smoking, dehydration, or tumors. Elevated levels of hemoglobin are associated with increased numbers or sizes of red blood cells, called polycythemia. This elevation may be caused by congenital heart disease, cor pulmonale, pulmonary fibrosis, too much erythropoietin, or polycythemia vera. Decrease of hemoglobin, with or without an absolute decrease of red blood cells, leads to symptoms of anemia. Anemia has many different causes, although iron deficiency and its resultant iron deficiency anemia are the most common causes in the Western world. As absence of iron decreases heme synthesis, red blood cells in iron deficiency anemia are hypochromic (lacking the red hemoglobin pigment) and microcytic (smaller than normal). Other anemias are rarer. |

According to some further embodiments, the Leukocyte concentration and the albumin concentration of a patient is determined based on the venous blood of said patient. The 'Hämohapto value Stool' is the concentration of a Hemoglobin-Haptoglobin-complex measured in the stool of a patient.

According to embodiments of the invention, the DSS comprises one or more decision support modules which, in operation, calculate a medical decision based on a received data structure by executing one or more of the following functions:

Monitoring of diseases

Steering the therapy

Risk assessment, and

Diagnose diseases

Monitoring of Diseases

According to embodiments, the DSS can analyze the course of the input data values over the time. According to some embodiments, the monitoring function also comprises issuing a warning message, e.g. to a physician, in case medically significant changes happened in the past or are predicted to happen in the future. According to preferred embodiments of the invention allowing the monitoring of diseases, the data values used as input for the DSS have assigned one or more timestamps.

The parameter values provided by data structures I-IV are advantageous as they each provide a minimum parameter set allowing the monitoring of a wide range of the most common diseases. Embodiments of the DSS system comprise program logic, e.g. rules, for analyzing the course of the parameter values of a patient provided by an instance of data structure variant I over the time and can e.g. warn the physician in case of significant changes of a parameter value over time. According to embodiments, said program logic comprises instructions for executing a statistical analysis for predicting disease which may affect a patient in the future.

| | Disease monitored |
|---|---|
| Additional Biomed. Param. of DS variant I | |
| Age | Generally important as certain diseases occur usually in specific age groups |
| Gender | Generally important as certain diseases have a higher prevalence depending on gender of the patient |
| Race or ethnicity | Generally important as certain diseases have a higher prevalence in specific ethnic groups |
| BMI (Body mass index) | Diabetes Mellitus (DM), obesity, cardiovascular disease, heart failure, cushing disease, eating disorders (e.g. Bulimia nervosa, Anorexia nervosa) |
| Waist/Hip ratio | DM, obesity, cardiovascular disease |
| Blood pressure | DM, obesity, cardiovascular disease, Stroke, kidney disease |
| Smoking history | Lung disease, cardiovascular disease, Stroke |
| CRP | Inflammatory disease, rheumatoid disorders, chronic disease, infection |
| Cholesterol | DM, obesity, cardiovascular disease, Stroke prevention |
| HDL | DM, obesity, cardiovascular disease, Stroke prevention |
| LDL | DM, obesity, cardiovascular disease, Stroke prevention |
| Glucose | DM, obesity |
| Hba1c | DM, obesity |
| Creatinine | Kidney disease |
| Triglycerides | DM, obesity, cardiovascular disease, Stroke prevention |
| Additional Biomed. Param. of DS variant II | |
| INR | Monitoring of blood anticoagulation therapy |
| Potassium (K) | Kidney disease, alimentary disorder |
| TSH | Thyroid disease |
| Additional Biomed. Param. of DS variant III | |
| GGT | Liver disease, liver damage, alcoholism |
| ALT, GPT | Liver disease, liver damage, alcoholism |
| Hemoglobin | Anemia, tiredness, eating disorder, blood loss |

Steering the Therapy

According to embodiments of the invention, the DSS is operable to determine which therapy schema is appropriate for treating a particular disease given a set of input parameters. The DSS may in addition be operable to determine, whether the input data parameters suggest to adapt the current therapy to a new situation. The optimum therapy of several diseases can be calculated by modules of the DSS based on the parameter values of the data structure variants I-III. If some parameter values change over time, the DSS provides a suggestion on how to adapt the related therapy to the new situation. This may happen even if the therapy is not directed at changing any of the parameter values of the data structure directly.

The below table illustrates a set of diseases which can be steered, according to embodiments of the invention, by evaluating biomedical parameter values of a patient contained in data structure variants I-III respectively.

| | Therapy of disease steered |
|---|---|
| Additional Biomed. Param. of DS variant I | |
| Age | Therapy is often depending on the age of a patient: e.g. lower doses for the elderly |
| Gender | Some drugs are in different use depending on the gender |
| [Race or ethnicity] | Metabolic processes may differ depending on the ethnicity or race. |

-continued

| Therapy of disease steered | |
|---|---|
| BMI (Body mass index) | Dosing may depend on BMI or body weight. DM, obesity |
| Waist/Hip ratio | DM, obesity, cardiovascular disease |
| Blood pressure | DM, obesity, cardiovascular disease, Stroke, kidney disease |
| Smoking history | Lung disease, cardiovascular disease, Stroke |
| CRP | Inflammatory disease, rheumatoid disorders, chronic disease, infection |
| Cholesterol | DM, obesity, cardiovascular disease, Stroke prevention |
| HDL | DM, obesity, cardiovascular disease, Stroke prevention |
| LDL | DM, obesity, cardiovascular disease, Stroke prevention |
| Glucose | DM, obesity |
| Hba1c | DM, obesity |
| Creatinine | Kidney disease |
| Triglycerides | DM, obesity, cardiovascular disease, Stroke prevention |
| Additional Biomed. Param. of DS variant II | |
| INR | Monitoring of blood anticoagulation therapy |
| Potassium (K) | Kidney disease, alimentary disorder |
| TSH | Thyroid disease |
| Additional Biomed. Param. of DS variant III | |
| GGT | Liver disease, liver damage, alcoholism |
| ALT (GPT) | Liver disease, liver damage, alcoholism |
| Hemoglobin | Anemia, tiredness, eating disorder, blood loss |

Risk Assessment

The set of input parameters is used by the DSS to estimate the risk of developing a disease in the future. The DSS may prompt a physician to change the patient's treatment or to initiate a new therapy to diminish the patient's risk. Some of the biomedical parameters of data structures I-III are suitable for calculating the risk of developing a disease in the future. One or more modules of the DSS calculate the risk and give notice to the physician to change the patient's treatment or to initiate a new therapy to diminish the patient's risk. The below table illustrates a set of diseases whose risk can be calculated, according to embodiments of the invention, by evaluating biomedical parameter values of a patient contained in data structure variants I-III respectively.

| Risk determined for Disease | |
|---|---|
| Additional Biomed. Param. of DS variant I | |
| Age | Generally important as certain diseases occur usually in specific age groups |
| Gender | Generally important as certain diseases have a higher prevalence depending on gender of the patient |
| Race or ethnicity | Generally important as certain diseases have a higher prevalence in specific ethnic groups |
| BMI (Body mass index) | DM, obesity, cardiovascular disease, heart failure, cushing disease, eating disorders (e.g. Bulimia nervosa, Anorexia nervosa) |
| Waist/Hip ratio | DM, obesity, cardiovascular disease |
| Blood pressure | DM, obesity, cardiovascular disease, Stroke, kidney disease |
| Smoking history | Lung disease, cardiovascular disease, Stroke |
| CRP | Inflammatory disease, rheumatoid disorders, cardiovascular disease |
| Cholesterol | DM, obesity, cardiovascular disease, Stroke prevention |
| HDL | DM, obesity, cardiovascular disease, Stroke prevention |
| LDL | DM, obesity, cardiovascular disease, Stroke prevention |

-continued

| Risk determined for Disease | |
|---|---|
| Glucose | DM, obesity |
| Hba1c | DM, obesity |
| Creatinine | Kidney disease |
| Triglycerides | DM, obesity, cardiovascular disease, Stroke |
| Additional Biomed. Param. of DS variant II | |
| INR | For differential diagnoses of coagulopathies (Vitamin K-, Factor V-, Factor X-deficiency) |
| Potassium (K) | Kidney disease, alimentary disorder |
| TSH | Thyroid disease |
| Additional Biomed. Param. of DS variant III | |
| GGT | Liver disease, liver damage, alcoholism |
| ALT (GPT) | Liver disease, liver damage, alcoholism |
| Hemoglobin | Anemia, tiredness, eating disorder, blood loss |

Diagnosing Diseases

According to DSS modules allowing the diagnosis of diseases, the set of input parameters is used to automatically calculate a diagnosis or a risk for a particular diagnosis. The DSS may also be operable to integrate timestamp values in the calculation: if an input parameter value was indicative of a healthy condition of the patient in the past and has changed as to indicate a pathologic state of the patient, said information may be used to increase the accuracy of the calculation. Some of the biomedical parameters of data structures I-III are suitable for calculating a new and current diagnosis for a patient by one or more modules of the DSS. If a value has been within a healthy value range in the past and changes to a pathologic state or if the first retrieved value of that kind is pathologic, the DSS suggests a new diagnosis.

The below table illustrates a set of current diseases which can be calculated, according to embodiments of the invention, by evaluating biomedical parameter values of a patient contained in data structure variants I-III respectively.

| Disease diagnosed | |
|---|---|
| Additional Biomed. Param. of DS variant I | |
| Age | Generally important as certain diseases occur usually in ethnicity specific age groups |
| Gender | Generally important as certain diseases have a higher prevalence depending on gender of the patient |
| Race or ethnicity | Generally important as certain diseases have a higher prevalence in specific ethnic groups |
| BMI (Body mass index) | Obesity, eating disorders (e.g. Bulimia nervosa, Anorexia nervosa) |
| Waist/Hip ratio | obesity, |
| Blood pressure | Cardiovascular disease, Stroke, kidney disease |
| Smoking history | Lung disease |
| CRP | Inflammatory disease, rheumatoid disorders |
| Cholesterol | Hyperlipidemia |
| HDL | Hyperlipidemia |
| LDL | Hyperlipidemia |
| Glucose | DM, obesity |
| Hba1c | DM, obesity |
| Creatinine | Kidney disease |
| Triglycerides | DM, obesity, |
| Additional Biomed. | |

-continued

| Disease diagnosed | |
|---|---|
| Param. of DS variant II | |
| INR | Coagulopathies (Vitamin K-, Factor V-, Factor X-deficiency) |
| Potassium (K) | Kidney disease, alimentary disorder |
| TSH | Thyroid disease |
| Additional Biomed. Param. of DS variant III | |
| GGT | Liver disease, liver damage, alcoholism |
| ALT (GPT) | Liver disease, liver damage, alcoholism |
| Hemoglobin | Anemia, eating disorder, blood loss |

According to further embodiments, the instantiated data structure is assigned a pseudonym of the person. The assignment allows to store the data structure comprising sensitive medical data of a person in a public database without disclosing the identify of a user. A 'public' database as used herein is a database which is accessible by persons such as physicians or other persons working in the healthcare sector. Depending on the embodiment, said database may also be accessible to a plurality of patients. According to some embodiments, at least some of the data structures comprising biomedical parameter values of a patient are stored in association with a medical decision calculated by a DSS by using said data structure as input. Assigning a pseudonym of the person to a data structure instance comprising medical and/or personal data of a person may comprise storing said pseudonym in association with said data structure or adding said pseudonym to the data structure. According to embodiments, the pseudonym of a person is used as a key in a relational database and allows assigning one or more data structures stored in said database to a person whose real name does not have to be stored in the database. The user's pseudonym can be used as a database access key, e.g. a primary key or candidate key value that uniquely identifies one or more data structures in a relational database, for read and write access.

Various computer implemented schemes for providing a pseudonym for a user are as such known. A pseudonym is typically used for protecting the informational privacy of a user such as in a social network. Such computer implemented schemes for providing a pseudonym typically enable the disclosure of identities of anonymous users if an authority requests it, if certain conditions are fulfilled. For example, Benjumea et al, Internet Research, Volume 16, No. 2, 2006 pages 120-139 devise a cryptographic protocol for anonymously accessing services offered on the web whereby such anonymous accesses can be disclosed or traced under certain conditions.

According to embodiments of the invention, the generation of a pseudonym, e.g. for a particular patient, comprises the steps:
  entering a user-selected secret,
  storing the user-selected secret in memory,
  computing a private key by applying an embedding and randomizing function onto the secret,
  storing the private key in the memory,
  computing a public key using the private key, the public key and the private key forming an asymmetric cryptographic key,
  erasing the secret and the private key from the memory, and
  outputting the public key for providing the pseudonym.

According to embodiments of the invention, said pseudonym is assigned to the data structure. For example, the pseudonym can be stored as part of the data structure or stored in association to said data structure on another storage medium. The data structure and its assigned pseudonym can be transmitted via a network and/or stored to a data storage afterwards.

The data structure may be a serialized data object, a plain text data object specified e.g. in XML format, an entry of a relational database table or the like. According to embodiments, the data structure is instantiated on a client device based on patient related data. The data structure can be specified by the DSI module and be submitted to a communication module, the DSI and the communication module being installed on a client computer, e.g. the computer of a physician.

After the data structure has been instantiated, the communication module, also referred to as 'communication layer', submits the data structure to a security module, also referred to as 'security interface', of the client device. The security interface is operable to generate a pseudonym for the data structure and/or to encrypt the data structure. The security interface may prompt a user to enter a user-specified secret. The pseudonymized (and possibly encrypted) data structure is sent via a network connection, e.g. the internet, from the security interface to a remote computer center and can there be stored to a central database comprising medial data of a multitude of patients. Depending on the embodiment, the data structure may be sent in addition or alternatively to a remote DSS.

According to embodiments wherein the data structure sent to the DSS in an encrypted form, the data structure can be decrypted by a 'server security interface' receiving the data structure before it is used as input for the DSS. The data structure may be stored to the database in an encrypted or decrypted form.

The remote DSS calculates a medical decision based on the received data structure and returns a message being indicative of the calculated decision to the client.

According to embodiments of the invention, the data structure sent to a remote DSS via an unsecure network connection comprises person-related, medical data. Embodiments of the present invention prevent the identification of a particular patient whose biomedical parameter values are stored in the data structure by applying a pseudonymization step on the patient's name or identifier.

In a further aspect, the invention relates to a computer readable storage medium having stored therein instructions, which when executed by a computing device cause the computing device to perform a method of generating an access key. Said method comprises the steps of:
  accessing an input value;
  calculating an asymmetric cryptographic key pair by applying a cryptographic one-way function to the input value, wherein the cryptographic key pair comprises a public key and a private key, wherein the cryptographic one-way function is an injective function;
  outputting the public key for providing the access key, and
  storing a data structure, e.g. of data structure variant I-IV, into a database using the provided access key.

Said secret can be, for example, a user-selected password, a secret key, or biometric data. According to embodiments of said method for generating an access key, at least one public parameter for applying the embedding and randomization function is used. According to embodiments, said public parameter is selected from the group consisting of a username, a user email address, and a user identifier, and the embedding and randomizing function is applied on the public parameter and the secret to provide a combination. Said Access key may be a primary key or candidate key value that uniquely identifies one or more data structures of a patient in a relational database for read and write access.

According to further embodiments, the embedding and randomization function comprises a binary Cantor pairing function for embedding the secret. According to still some further embodiments, the embedding and randomizing function comprises the step of encrypting at least the embedded secret using a symmetric cryptographic algorithm by means of a symmetric key for randomizing the embedded secret. According to still further embodiments, the embedding and randomizing function comprises the step of encrypting at least the secret using AES by means of a user-specific symmetric key for embedding and randomizing the secret. According to some embodiments, the computation of the public key is performed by ECC cryptography.

According to embodiments, the embedding and randomizing function comprises the steps of applying a first one-way function on the secret to provide a first value, providing a random number, embedding the random number and the first value by combining them to provide a combination, and applying a second one-way function on the combination to provide a second value, wherein the second value constitutes the private key. According to embodiments, said first one-way function is a first hash function, and the second one-way function is a second hash function.

According to embodiments, the method for generating an access key further comprises the step of storing the random number in a database using a public parameter assigned to the user as a database access key.

According to embodiments, the method for generating an access key further comprises the steps of providing a set of domain parameters comprising a first base point for the ECC cryptography, computing a first public key for providing a first pseudonym by the ECC cryptography using the domain parameters and the first base point, replacing the first base point by a second base point in the domain parameters, and computing a second public key by ECC cryptography using the second base point to provide a second pseudonym.

According to some embodiments, the data structure according to embodiments of the invention is deposited together with the medical decision into a database, whereby the provided access key is used as key to access said decision. According to embodiments, a medical decision being calculated based on the data structure is stored together with said data structure in the database.

According to further embodiments, the method stored on said computer-readable storage medium further comprises the steps of depositing the data structure specified and/or instantiated according to any of the above embodiments into a database using the provided access key.

According to further embodiments, the method stored on said computer-readable storage medium further comprises the step of generating a digital signature for the data structure using the private key, wherein the digital signature is deposited into the database with the data structure.

In a further aspect, the invention relates to a computer system comprising a servercomputer-system, whereby the server-computer system comprises:
an interface for receiving a data structure according to any of the above embodiments via a network connection from a client computer system,
a processor,
a first computer-readable storage medium comprising instructions which, when executed by the processor, provide for a decision support system, the decision support system in operation receiving the data structure from the first interface and calculating a medical decision based on the received data structure, the decision support system being interoperable with a software application of the client computer system,
wherein the set of biomedical parameters contained in the received data structure allows an interactive usage of the decision support system by the software application over the network connection with minimal response times, e.g. within milliseconds or seconds.

According to further embodiments, said computer system further comprises a client computer system. Said client-computer system comprises a second computer-readable storage medium, the second computer-readable storage medium comprising instructions which, when executed by a processor of the client-computer system, cause said processor to perform a method of generating an access key. Said method comprises the steps of:
accessing an input value;
calculating an asymmetric cryptographic key pair by applying a cryptographic one-way function to the input value, wherein the cryptographic key pair comprises a public key and a private key, wherein the cryptographic one-way function is an injective function; and
outputting the public key for providing the access key,
storing the data structure together with the medical decision into a database using the provided access key. According to embodiments, said database may be operatively coupled to the server-computer system.

According to further embodiments of the above computer system, the decision support system is a modular decision support system comprising one or more modules, each module calculating a different medical decision.

Embodiments of the present invention are particularly advantageous as an extremely high degree of protection of the informational privacy of users is provided. This is due to the fact that an assignment of the user's identity to the user's pseudonym does not need to be stored and that no third party is required for establishing a binding between the pseudonym and the user's identity. In contrast, embodiments of the present invention enable to generate a user's pseudonym in response to the user's entry of a user-selected secret whereby the pseudonym is derived from the user-selected secret. As the user-selected secret is only known by the user and not stored on any computer system there is no way that a third party could break the informational privacy of the user, even if the computer system would be confiscated such as by a government authority. By pseudonymizing a data structure comprising medical data of a user before said data structure is submitted to a remote DSS via a potentially unsecure network, it is guaranteed that even in case an illegitimate person should get access to the communicated or remotely stored data structure, he cannot decipher the identity of the patient.

This enables to store sensitive user data, such as medical data, in an unencrypted form in a publicly accessible database. The user's pseudonym can be used as a database access key, e.g. a primary key or candidate key value that uniquely identifies tuples in a database relation, for read and write access to data objects stored in the database. According to some embodiments, pseudonymized data structure may be encrypted by a security interface in addition to increase security.

For example, the database with pseudonymous data can be used for a decision support system, e.g. in the medical field for evaluating a user's individual medical data and processing the data by rules. The result of the evaluation and processing by rules may be hints and recommendations to the physician regarding the user's health condition and further treatment. As a pseudonymized but unencrypted data structure does not need to be decrypted before it is used as input for the DSS, an encryption step on the client side and a decryption step on the server side is made unnecessary, thereby minimizing waiting times for the user and improving the usability of a remote DSS system.

In accordance with an embodiment of the invention, at least one public parameter is used for applying the embedding and randomization function. A public parameter may be the name of the user, an email address of the user or another identifier of the user that is publicly known or accessible. A combination of the user-selected secret and the public parameter is generated by the embedding component of the embedding and randomization function that is applied on the user-selected secret and the public parameter.

The combination can be generated such as by concatenating the user-selected secret and the public parameter or by performing a bitwise XOR operation on the user-selected secret and the public parameter. This is particularly advantageous as two users may by chance select the same secret and still obtain different pseudonyms as the combinations of the user-selected secrets with the user-specific public parameters differ.

In accordance with an embodiment of the invention, the embedding component of the embedding and randomizing function comprises a binary cantor pairing function. The user-selected secret and the public parameter are embedded by applying the binary cantor pairing function on them.

In accordance with an embodiment of the invention, the randomizing component of the embedding and randomizing function uses a symmetric cryptographic algorithm like the Advanced Encryption Standard (AES) or the Data Encryption Standard (DES) by means of a symmetric key. This can be performed by encrypting the output of the embedding component of the embedding and randomizing function, e.g. the binary cantor pairing function, using AES or DES.

In accordance with an embodiment of the invention, the symmetric key that is used for randomization by means of a symmetric cryptographic algorithm is user-specific. If the symmetric key is user-specific, the use of a public parameter can be skipped, as well as embedding the user-selected secret and the public parameter; the randomizing function can be applied then solely on the user-selected secret. By applying a symmetric cryptographic algorithm onto the user-selected secret using a user-specific symmetric key, both embedding and randomization of the user-selected secret are accomplished. If the symmetric key is not user-specific, the use of the public parameter and embedding the user-selected secret and the public parameter are necessary.

In accordance with an embodiment of the invention, the embedding and randomizing function is implemented by performing the steps of applying a first one-way function on the user-selected secret to provide a first value, providing a random number, embedding the random number and the first value to provide a combination, and applying a second one-way function on the combination to provide a second value, wherein the second value constitutes the private key. This embodiment is particularly advantageous as it provides a computationally efficient method of implementing an embedding and randomization function.

In accordance with an embodiment of the invention, the computation of the public key is performed by elliptic curve cryptography (ECC). The private key that is output by the embedding and randomizing function is multiplied with a first base point given by the domain parameters of the elliptic curve to provide another point on the elliptic curve, which is the pseudonym.

In accordance with an embodiment of the invention, the embedding and randomizing function is implemented by computer-readable instructions of the client side security module. According to some embodiments, the decryption of a data structure is realized by a server side security module.

In accordance with an embodiment of the invention, it is determined whether the output of the embedding and randomizing function fulfils a given criterion. For example, it is checked whether the output of the embedding and randomization function is within the interval between 2 and n−1, where n is the order of the elliptic curve. If the output of the embedding and randomizing function does not fulfill this criterion another random number is generated and the embedding and randomization function is applied again to provide another output which is again checked against this criterion. This process is performed repeatedly until the embedding and randomizing function provides an output that fulfils the criterion. This output is then regarded as the private key that is used to calculate the public key, i.e. the pseudonym, by multiplying the private key with the first base point.

In accordance with a further embodiment of the invention the base point is varied leaving the other domain parameters unchanged for computation of multiple pseudonyms for a given user. This provides a computationally efficient way to compute multiple pseudonyms for a given user in a secure way.

In another aspect the present invention relates to a computer readable storage medium having stored therein instructions, which when executed by a computer system, cause the computer system to generate a pseudonym for a user upon a user's entry of a user-selected secret by performing the steps of storing the user-selected secret in memory, computing a private key by applying an embedding and randomizing function onto the secret and possibly additional public parameters, storing the private key in memory, computing a public key using the private key, the public key and the private key forming an asymmetric cryptographic key pair, erasing the secret and the private key from memory, outputting the public key for providing the pseudonym. According to embodiments, the PKI server 844 allows to prove the ownership of a public key by a particular person.

In another aspect the present invention relates to a computer system comprising means for entering a user-selected secret, memory means for storing the user-selected secret and possibly additional public parameters and a private key, processor means being operable to compute the private key by applying an embedding and randomizing function onto the secret, compute a public key using the private key, the public key and the private key forming an asymmetric cryptographic key pair, erase the secret and the private key as well as any intermediate computational results from memory, and output the public key for providing the pseudonym.

In another aspect, the invention provides for a computer implemented method of generating a pseudonym. The method comprises the step of accessing an input value. The method further comprises the step of calculating a pseudonym by applying a cryptographic one-way function to the input value. The cryptographic one-way function is an injective function. This embodiment is advantageous because the input value is used to calculate a pseudonym using a cryptographic one-way function. The pseudonym can be used by a user as a pseudonym for many different situations for instance for an online forum or in order to keep medical records private. The advantage of using an input value to generate a pseudonym using a cryptographic one-way function is that it is not necessary to store a table with users and their pseudonyms. This increases the security of the pseudonym because the input value can be kept private and not shared or stored within a system. Because the pseudonym is calculated using a cryptographic one-way function the input value will be impossible to calculate from the pseudonym.

In another aspect the invention provides for a computing device comprising a processor and a memory. The memory contains instructions for performing a method of generating a pseudonym. The method comprises the step of accessing an input value. The method further comprises the step of calculating a pseudonym by applying a cryptographic one-way function to the input value. A cryptographic one-way function is an injective function. The advantages of this embodiment have been previously discussed.

In another embodiment the computing device is any one of a cellular telephone, a smart card 843, a security token, a personal digital system, an RFID tag, an RFID card, a computer, and a computer system. In the case of security token the computing device may also comprise components or a computer external to the security token. For instance if the security token simply has storage for the input value, then the computing device may be a computer or other computing device which accesses the memory of the security token. The computing device may be a client computer system 831.

In another embodiment the input value is a private key which can be used for calculating at least one public key to form at least one asymmetric cryptographic key pair. The advantages of this embodiment have been previously discussed.

In another embodiment the computing device comprises memory wherein the input value is stored. In this embodiment the input value is stored within the memory and is accessible by reading the memory from the computing device. In this case the input value may be secured by securing the computing device. For instance in the case of a smart card or an RFID card the input value may be stored in secure memory which may not be accessed without proper access instructions and which is physically protected from tampering.

In another embodiment a user-selected secret is received from a user interface. The input value is derived from the user-selected secret. In this embodiment security for the input value is provided by not storing it in the computing device. The input value is generated from a user-selected secret.

In another embodiment the computing device comprises a user interface for entering a user-selected secret. The computing device further comprises a memory for storing the user-selected secret and a private key. The computing device further comprises a processor operable for executing instructions stored in the memory. The memory contains instructions for performing the step of receiving a user-selected secret. The memory further comprises instructions for performing the step of storing the user-selected secret in memory. The memory further contains instructions for performing the step of computing a private key by applying an embedding and randomizing function onto the secret and possibly additional public parameters. The memory further contains instructions for performing the step of storing the private key in the memory. According to embodiments, the private key is the input value. The memory further contains instructions for performing the step of computing a public key using the private key using a cryptographic one-way function. The public key and the private key form an asymmetric cryptographic key pair. The memory further contains instructions for performing the step of outputting the public key for providing the pseudonym. The memory further contains instructions for performing the step of erasing the secret and the private key from the memory.

Creating a Database Access Key

In a further aspect, embodiments of the invention provide for a computer readable storage medium having stored therein instructions. When the instructions are executed by a computing device the instructions cause the computing device to perform a method of generating an access key. The method comprises the step of accessing an input value. The method further comprises the step of calculating an asymmetric cryptographic key pair by applying a cryptographic one-way function to the input value. The cryptographic key pair comprises a public key and a private key. The cryptographic one-way function is an injective function. The method further comprises the step of outputting the public key for providing the access key. Essentially the public key is the access key. This embodiment is advantageous because the input value may be used to generate the access key. A user operating the computing device therefore does not need to know the access key. The user can obtain the access key by executing the instructions on the computing device.

In another embodiment the method further comprises the step of depositing data into a database using the access key. This embodiment is advantageous because the access key may be used to control access or control data that is able to be written into the database. Alternatively the access key could be used as a pseudonym for which data deposited into the database is referenced against. This provides anonymity for a user.

In another embodiment the method further comprises the step of generating a digital signature for the data using the private key. The digital signature is deposited into the database, associated with the data. This embodiment is particularly advantageous because the digital signature for the data allows authentication of the data. In this way the authorship of the data can be verified.

In another embodiment the method comprises the step of verifying the authenticity of the data using the access key. This embodiment is advantageous because the authenticity or authorship of the data can be verified using the access key.

In another embodiment the access key is used as a pseudonym by the database. In this embodiment the data which was deposited into the database is referenced as being deposited by a specific person or entity using a pseudonym. An advantage of this embodiment of the method is that data can be stored or referenced in a database using the pseudonym without revealing the identity of who placed the data into the database.

In another embodiment the input value is the private key. This is advantageous because the input or private key may be stored within the computer readable storage medium or another computer storage medium and kept securely. The private key can then be used to generate a unique access key for the database.

In another embodiment the method further comprises the step of calculating a first public key using the input value and a first base point. The public key is calculated using asymmetric cryptography which is implemented using elliptical curve cryptography. The method further comprises the step of outputting the first public key as a pseudonym. This embodiment is advantageous because a private key has been used to generate a pseudonym calculated from a public key using elliptic curve cryptography. A pseudonym has been generated for which the input value or private key cannot be inferred.

In another embodiment the method further comprises the step of calculating a second public key using the input value and a second base point. The second base point is different from the first base point and cannot be inferred from it. The method further comprises the step of outputting the second public key as a public key for the encryption of data. This embodiment is advantageous because a single input value or private key has been used to generate both a pseudonym and a public key for the encryption of data. This is particularly advantageous because both values cannot be inferred from each other, yet only a single input value is needed for both. In other words, knowldge of one of the base points does not allow an attacker to determine the other base point. The two base points are therefore not correlatable. However, both of the base points are determined by a single input value or private key.

In another embodiment the cryptographic one-way function comprises an embedding and/or randomizing function. This is advantageous because the input value may be clear text or an easily guessed value. By using an embedding and/or randomizing function a pseudonym which is more difficult to decrypt may be constructed.

In another aspect the invention provides for a computer implemented method of generating an access key. The method comprises the step of accessing an input value. The method further comprises the step of calculating an asymmetric cryptographic key pair by applying a cryptographic one-way function to the input value and further steps. The cryptographic key pair comprises a public key and a private key. The cryptographic one-way function is an injective function. The method further comprises the step of outputting the public key for providing the access key. This embodiment is advantageous because the input value is used to calculate a pseudonym using a cryptographic one-way function. In some embodiments, the access key can be used by a user as a pseudonym for many different situations for instance for an online forum or in order to keep medical records private. The advantage of using an input value to generate a pseudonym e.g. by using a cryptographic one-way function is that it is not necessary to store a table with users and their pseudonyms. This increases the security of the pseudonym because the input value can be kept private and not shared or stored within a system. Because the pseudonym is calculated using a cryptographic one-way function the input value will be impossible to calculate from the pseudonym.

In another aspect the invention provides for a computing device comprising a processor and a memory. The memory contains instructions for performing a method of generating an access key. The method comprises the step of accessing an input value. The method further comprises the step of calculating an asymmetric cryptographic key pair by applying a cryptographic one-way function to the input value and further steps. The cryptographic key pair comprises a public key and a private key. The cryptographic one-way function is an injective function. The method further comprises the step of outputting the public key for providing the access key. The advantages of the method performed by executing the instructions has been previously discussed.

In another embodiment the computing device is any one of a cellular telephone, a smart card, a security token, a personal digital system, an RFID tag, an RFID card, a computer, and a computer system. In the case of security token the computing device may also comprise components or a computer external to the security token. For instance if the security token simply has storage for the input value, then the computing device may be a computer or other computing device which accesses the memory of the security token. The computing device may be a computer system.

In another embodiment the input value is a private key which can be used for calculating at least one public key to form at least one asymmetric cryptographic key pair. The advantages of this embodiment have been previously discussed.

In another embodiment the computing device comprises memory wherein the input value is stored. In this embodiment the input value is stored within the memory and is accessible by reading the memory from the computing device. In this case the input value may be secured by securing the computing device. For instance in the case of a smart card or an RFID card the input value may be stored in secure memory which may not be accessed without proper access instructions and which is physically protected from tampering.

In another embodiment a user-selected secret is received from a user interface. The input value is derived from the user-selected secret. In this embodiment security for the input value is provided by not storing it in the computing device. The input value is generated from a user-selected secret.

In another embodiment the computing device comprises a user interface for entering a user-selected secret. The computing device further comprises a memory for storing the user-selected secret and a private key. The computing device further comprises a processor operable for executing instructions stored in the memory. The memory contains instructions for performing the step of receiving a user-selected secret. The memory further comprises instructions for performing the step of storing the user-selected secret in memory. The memory further contains instructions for performing the step of computing a private key by applying an embedding and randomizing function onto the secret and possibly additional public parameters. The memory further contains instructions for performing the step of storing the private key in the memory. The private key is the input value. The memory further contains instructions for performing the step of computing a public key using the private key using a cryptographic one-way function. The public key and the private key form an asymmetric cryptographic key pair. The memory further contains instructions for performing the step of outputting the public key for providing the pseudonym. The memory further contains instructions for performing the step of erasing the secret and the private key from the memory.

BRIEF DESCRIPTION OF THE DRAWINGS

In the following, embodiments of the invention are described by way of example, only making reference to the drawings in which:

FIG. 9 illustrates a data structure in XML format.

DETAILED DESCRIPTION

Figure 1:
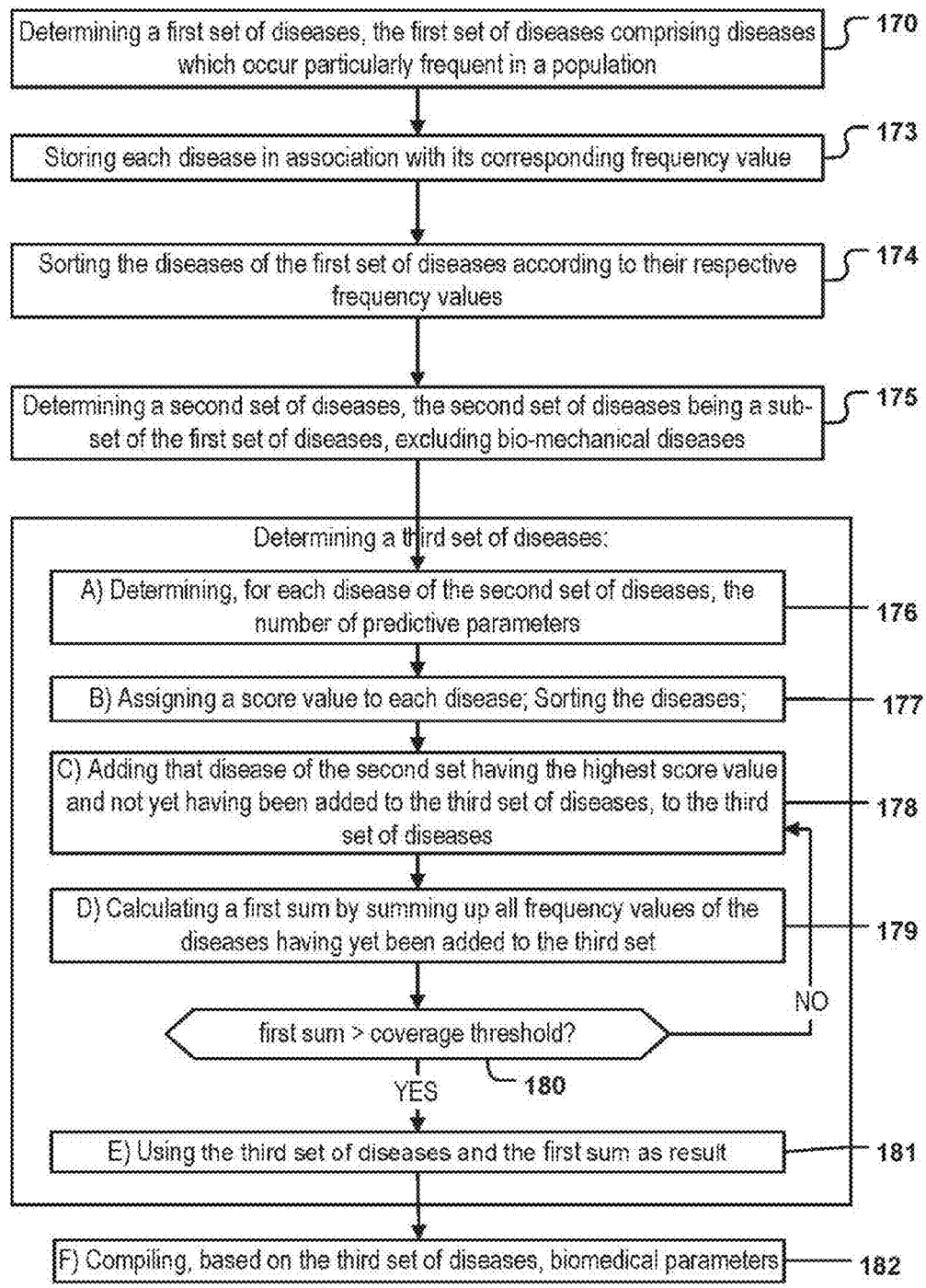
FIG. 1 is a flowchart for specifying a data structure comprising multiple biomedical parameters.

FIG. 1 depicts a flowchart of a method for specifying a data structure. In step 170 a first set of diseases is determined. The first set of diseases comprises diseases whose frequencies exceed a first threshold value. The first set of diseases is determined for a particular population of persons. The population of persons can be, for example, the population of a country, of a continent, of a set of countries such as industrialized nations or the like. The frequency of the disease can be determined in absolute numbers or in relative frequencies. For example, the number of doctor visits per year in said population of persons which are caused by a particular disease can be used as an 'absolute' frequency value.

According to some embodiments said absolute frequency value has to be transformed into a relative frequency value for each disease. In case it is determined that an absolute frequency value was provided, this can be achieved by dividing the absolute frequency value of a particular disease in the population by the total occurrence value of said disease. For example, if the absolute disease frequency is measured in terms of doctor visits, the number of doctor visits per year in said population caused by a particular disease can be divided by the total number of doctor visits per year in the population. In other embodiments of the invention, the calculation is based not on the number of doctor visits caused by disease but rather on the total amount of costs for medical equipment and medication which are caused by a particular disease per year in said population.

Step 170 can be executed by a computer by reading a manually compiled list comprising disease names and/or disease identifiers in association with a corresponding frequency value. According to some embodiments, the threshold for including the disease in the first set of diseases this the absolute number of people being affected by that's disease, e.g. 1000 individuals in a population of about 100 million people. According to other embodiments, said threshold is a relative value, e.g. 4% of the doctor visits in a population per year. According to other embodiment, a predefined number of the diseases with the highest percentage values is used to specify the first set of diseases. For example, the 30 most frequent diseases in a population can be used to constitute the first set of diseases.

After having determined the first set of diseases, step 173 is executed, wherein each data object representing a disease, in the following referred to as 'disease data object', is stored in association with its corresponding absolute or relative frequency value. The disease data object and its associated frequency value are stored to a computer readable storage medium. The computer readable storage medium can be, for example, a magneto-optic storage disk or a flash drive of a processing device. The deceased data object can also be stored in the working memory for further processing steps.

In step 174, the first list of diseases is sorted according to the frequency values of each disease in descending order.

In step 175, a second set of diseases is compiled as a subset of the first set of diseases. The second subset comprises all diseases of the first subset except biomechanical diseases. For example, a bone fracture is typically considered as biomechanical disease as a bone fracture is not detected by measuring a set of laboratory values but by x-ray photographs. Such x-ray photographs or other medical images are difficult to process by medical decision support systems. Usually, the processing of medical images requires complex programs being specially adapted to interpret and process information contained in images.

In step 176, the number of nominal, ordinal or metric parameters is determined which can be used, according to current medical knowledge, to diagnose or predict the risk for each disease of the second set of diseases is determined. Medical parameters known to correlate with a disease are also considered as predictive parameters. According to embodiments, a file is read by a computer program, the file comprising mapping information which maps each disease to one or more parameters required for its prediction.

In step 177, a scoring function is executed which assigns to each diagnosis a score value, the score value being dependent from the frequency value of a disease and from the number of parameters mapped to said disease. The higher the frequency of a disease in the population, the higher the score assigned to the disease by the scoring function, and the larger the number of predictive parameters required for the characterization or prediction of the disease, the lower the score assigned to the disease by the scoring function. Depending on the embodiment, the impact of the predictive parameter number and the impact of the disease frequency value on the final score value may vary, resulting in a score which primarily indicates the disease frequency or the number of predictive parameters having been mapped to said disease or which indicates both aspects to the same extent. The diseases contained in the second set of diseases are sorted based on their respective score values in descending order.

In a further step, a loop process is initiated:

In step 178, that disease belonging to the second set of diseases having assigned the highest score value and not yet having been added to the third set of diseases is determined and added to the third set of diseases.

In step 179, a first sum is calculated by summing up all frequency values of all diseases having yet been added to the third set of diseases.

In step 180 it is determined whether the first sum is larger than a specified coverage threshold value. Such a coverage threshold value is usually specified by the user before the method for determining the first set of diseases is started. Typically, a coverage threshold of approximately 60%, 70%, and 80% is used. After steps 178 and 179 have been executed the first time, the coverage threshold will typically not have been reached. In case said coverage threshold is not exceeded by the second sum, steps 178 and 179 are repeated and a disease of the second set of diseases having the highest score value which has not yet been added to the third set of diseases is added to the third set of diseases. Again, in step 179, the first sum is calculated. Steps B—178 and C—179 are executed until the total frequency value of all diseases having been added to the third set of diseases exceeds the coverage threshold value. When the first sum exceeds the coverage threshold value, the third set of diseases and the second first are used in step 181 as a result.

According to embodiments of the invention, the first sum is normalized during the execution of step 179 to obtain a total sum of frequency values of 100%. The normalization step is advantageous, because many people, in particular elder people, are affected by a multitude of diseases (multi-morbid persons). Accordingly, one doctor visit may be caused by a multitude of diseases. For example, chronic diabetes may result in circulatory disorders and impaired vision. Accordingly, the doctor may have to diagnose or treat the basic disease and several additional diseases during a doctor's visit. Simply summing up all diseases causing a doctor visit without normalization will therefore usually result in the calculation of a first sum exceeding 100%.

Finally, in step 182, a set of biomedical parameters is compiled to be used as input of a DSS for predicting the risk of diseases, said set of biomedical parameters comprising all biomedical parameters having mapped to each disease having been added to the third set of diseases. According to embodiments of the invention, said compilation is executed automatically by a computer program reading a mapping file, wherein said mapping file comprises, for each known disease in the population, or at least for each disease in the third set of diseases, one or more biomedical parameters which are known to correlate with or cause said disease. According to some embodiments, said mapping file may be based on the same mapping information used to determine the number of predictive parameters for a particular disease in step 176. Accordingly, the predictive biomedical parameters of the diseases of the third set of diseases are used to compile the set of biomedical parameters. The compiled parameter set is considered as minimum required set of parameters covering at least the diseases of the population according to the coverage threshold value. According to preferred embodiments, all biomedical parameters having been mapped to a particular disease of the third set of diseases are used for compiling the set of biomedical parameters.

It is possible that the parameters compiled in step 182 can be used to calculate the risk for additional diseases which have not been added to the third set of diseases. For example, a rare disease may have not been considered as member of the first set of diseases although the risk of obtaining said rare disease may be predictable based on parameters which can also be used for predicting a more frequently occurring disease. In a final, optional step (not shown) which is executed according to some embodiments of the invention, all diseases which can be predicted based on the compiled parameter set are determined. In case a determined disease is not yet part of the third set of diseases, said disease is added to the third set of diseases and a second sum is calculated by summing up all frequency values of the diseases having yet been added to the third set. The second sum is usually larger than the first sum as additional diseases may have been included into the third set.

According to embodiments, the compiled set of input parameters is used to specify a data structure which can be provided as input for a DSS. A data structure comprising input parameter values specified by executing the steps 170-182 is particularly advantageous because of its small size: a comparatively small set of metric, nominal and/or ordinal data values covers the majority of diseases in the population and can be quickly distributed to a remote medical DSS also via a network of low bandwidth. Depending on the embodiment, a new instance of said data structure is created on the occasion of receiving one or more laboratory values of a patient, of entering patient data in a computer system by a physician, of reading a patient record from a storage medium, e.g. an electronic patient card or the like.

The following table shows a ranking of the most frequent diseases in Germany in percentages exceeding a frequency threshold of 3.8%. The disease groups contained in table 1 are herein also considered as 'disease'. The diseases listed in table 1 represent a first set of diseases according to one embodiment of the invention. Relative frequencies associated to each groups are listed in the 3rd column of table 1. The percentage values may differ in other populations, e.g. in other countries. Pure biomechanical diseases are indicated with double asterisks. All diseases whose frequency values have not been indicated with double asterisks are members of the second set of diseases.

Three coverage threshold values I-III have been specified. For each specified threshold value, a set of diseases I-III is determined and a corresponding set of biomedical parameters is compiled as described. For each parameter set, a corresponding data structure I-III is specified which can be instantiated by assigning each parameter of a parameter set a data value derived from a particular patient.

TABLE 1

Most common diagnoses in percent in the year 2008
(source: Gesundheitsberichterstattung des Bundes website).

| Diagnoses by ICD10 | Contained in Parameter Set/Data Structure | Percentage of cases % | Rank based on calculated Score |
|---|---|---|---|
| I10 Essential (primary) hypertension | I | 31.6 | 1 |
| E78 Disorders of lipoprotein metabolism and other lipidaemias | I | 23.4 | 2 |
| M54 Dorsalgia | | 14.6 | |
| I25 Chronic ischaemic heart disease | I | 10.1 | 3 |
| E04 Other nontoxic goitre | II | 9.9 | 11 |
| E11 Non-insulin-dependent diabetes mellitus | I | 9.4 | 4 |
| E66 Obesity | I | 8.1 | 5 |
| M53 Other dorsopathies, not elsewhere classified | | 7.3 | |
| K29 Gastritis and duodenitis | IV | 7.0 | 17 |
| I83 Varicose veins of lower extremities | | 6.9 | |
| K76 Other diseases of liver | III | 6.9 | 15 |
| M47 Spondylosis | | 6.7 | |
| E79 Disorders of purine and pyrimidine metabolism | IV | 6.4 | 18 |
| M17 Gonarthrosis [arthrosis of knee] | | 6.1 | |
| K21 Gastro-oesophageal reflux disease | IV | 6.0 | 19 |
| J44 Other chronic obstructive pulmonary disease | I | 5.9 | 6 |
| J06 Acute upper respiratory infections of multiple and unspecified sites | I | 5.6 | 7 |
| J45 Asthma | I | 5.6 | 8 |
| F32 Depressive episode | II | 5.6 | 12 |
| M51 Other intervertebral disc disorders | | 5.4 | |
| J30 Vasomotor and allergic rhinitis | IV | 5.1 | 20 |
| J20 Acute Bronchitis | I | 4.9 | 9 |
| M81 Osteoporosis without pathological fracture | IV | 4.4 | 21 |
| I50 Heart failure | I | 4.3 | 10 |
| I49 Other cardiac arrhythmias | II | 4.3 | 13 |
| Z25 Need for immunization against other single viral diseases | IV | 4.3 | 22 |
| K80 Cholelithiasis | III | 4.1 | 16 |
| G47 Sleep disorders | IV | 3.9 | 23 |
| F45 Somatoform disorders | IV | 3.9 | 24 |
| T78 Adverse effects, not elsewhere classified | II | 3.8 | 14 |

Upon having executed the method for specifying the data structure four times with four different threshold values each, four variants I-IV of third sets of diseases have been determined, whereby the third set of diseases II comprises all diseases of the third set of diseases I and additional diseases. The third set of diseases III comprises all diseases of the third set of diseases II and additional diseases, and so forth.

The determination of the third set of diseases I results in a compilation of parameter set I. The determination of the third set of diseases II results in a compilation of parameter set II, and so forth. Correspondingly, parameter set I is a sub-set of parameter set II and parameter set II is a sub-set of parameter set III. After having canceled out pure biomechanical diseases, the frequency values of the remaining diseases sum up to 184.5%.

TABLE 2 sum of disease frequencies corresponding to parameter sets I-III

|  | Summed percentage of cases (including biomechanical diseases) | Sum calculated for the members of the second set of diseases | Sum of freq. values of diseases corresp. to parameter set I | Sum of freq. values of diseases corresp. to parameter set II | Sum of freq. values of diseases corresp. to parameter set III |
|---|---|---|---|---|---|
| TOTAL | 231.5% | 184.5% | 108.9% | 132.5% | 143.5% |
| RELATIVE coverage (Total coverage divided by 184.5%) |  | 100% (this value is normalized to 100%) | 59% | 72% | 78% |

The sum of disease frequencies covered by a set of predictive parameters is herein understood as the 'disease-coverage' provided by a data structure comprising said set of predictive parameters.

Figure 2:
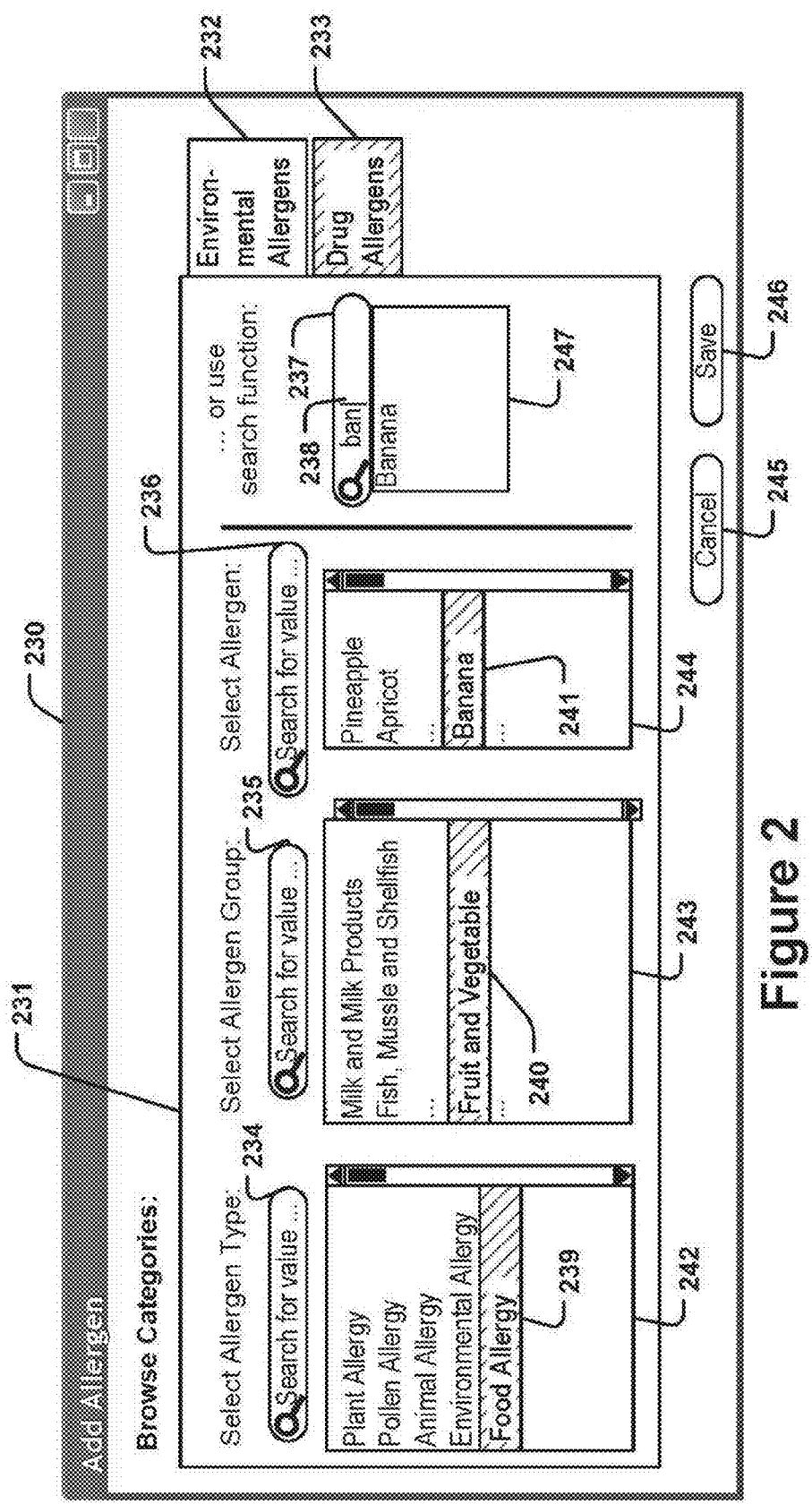
FIG. 2 is a dialog window facilitating the instantiation of a data structure via GUI elements for entering environmental allergies.

FIG. 2 depicts a dialog window 230 which assists the user, e.g. a doctor, in instantiating the data structure according to embodiments of the invention for a particular person.

It has been observed, that the biomedical parameter 'allergies and intolerances' is an important predictive parameter as allergies and intolerances of various kinds are common causes of many diseases. According to some embodiments, allergies and intolerances of the patient are used to instantiate a data structure to be used as input for a DSS. Entering a particular allergy or intolerance was observed to be difficult in many state-of-the-art doctor information systems due to the sheer amount of substances and drugs which can cause an allergy or intolerance. The amount of substance names makes it almost impossible to remember the correct name of any of those substances and to enter the appropriate data value, e.g. an identifier of a particular substance catalog, quickly.

A further problem is that specifying such allergens manually results in a multitude of different spelling variants which again can be an obstacle for an automated, computer-based processing of data, because spelling variants do not allow to map a particular term or expression to an unequivocal identifier of a particular item of a drug database or other kind of catalog.

Figure 3:
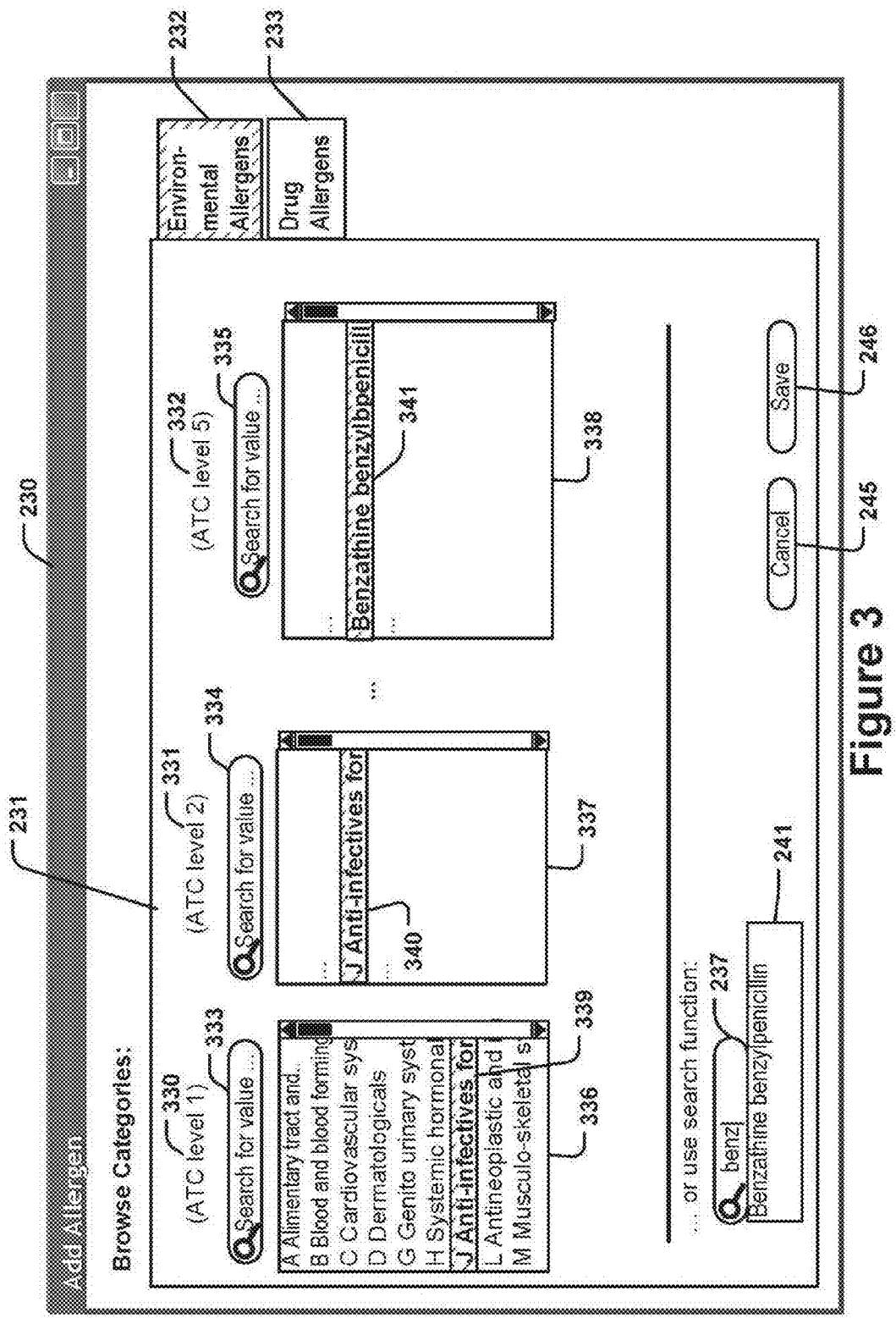
FIG. 3 is a dialog window facilitating the instantiation of the data structure via GUI elements for entering drug allergies.

According to embodiments of the invention, said two problems are solved by automatically reading one or more predefined catalogs from a storage medium and presenting said catalogs to a user for selection by means of a graphical user interface as depicted in FIGS. 2 and 3. For example, various commercial and non-commercial ontologies or thesauri, which in the following will be referred to as 'catalogs', are available which comprise a multitude of environmental factors and drugs in a hierarchical order. The dialog window 230 comprises several graphical user elements 242, 243, 244, which display catalog elements being contained in different hierarchical levels of a catalog. The dialog window comprises one or more selectable GUI elements 232, 233 allowing the user to select one particular catalog. For example, GUI element 232 represents a catalog comprising environmental allergies and GUI element 233 represents a catalog comprising drug allergens.

According to FIG. 2, the user has selected environmental allergies. As a result of said selection, the set of catalog elements of the highest order of the selected catalog (environmental allergens) are displayed in GUI element 242. GUI element 242 can be, depending on the embodiment, a drop down list, a scrollable list or the like. The list comprises catalog elements such as 'client energy', 'pollen allergy', 'animal energy', 'environmental energy', and 'food allergy' 239. The user can select any of the GUI elements of the list displayed in GUI element 242, e.g. food allergy 239, as indicated by the hachuring. Upon selecting GUI element 'food allergy' 239, the catalog elements being child nodes of the selected 'food allergy' catalog element are displayed in GUI element 243. Said child catalog elements comprise 'milk and milk products', 'fish, muscle and shellfish', 'food and vegetable' 240, and several other catalog elements indicated by three dots.

Upon selection of the selectable GUI element 240 representing the 'fruit and vegetable' catalog element, a user can trigger the display of catalog elements being child nodes of the selected 'fruit and vegetable' catalog element within the Environ mental allergens tree. As a result of said selection, GUI elements representing the child nodes of the 'fruit and vegetable' catalog element are displayed in the GUI area 244, for example 'pineapple', 'apricot', 'banana' 241, and others. Although the environmental allergies catalog may comprise thousands of different items, the hierarchal structure of the catalog and the structure and dynamic behavior of the dialog window 230 allows to find any particular element, in this case 'banana' 241, by just three clicks (selecting 'food allergy', 'fruit and vegetable', and 'banana'). In addition, the dialog window at 230 provides for each of the GUI elements 242, 243, and 244 a search field 234, 235, and 236 for searching catslog elements of different hierarchical levels.

GUI area 242 corresponds to the highest hierarchical level, the level of the allergy types of the environmental allergies catalog. GUI area 243 corresponds to the hierarchical level of allergen groups. GUI area 244 corresponds to the most basic level of the hierarchy, the singular allergens. In case a doctor already knows which particular allergen he wants to enter he may enter this name directly in the search field 236. In case the user does not know to which hierarchical level the particular term or phrase belongs to, he may enter the search phrase in the search field to 372 and trigger a search covering all hierarchical levels of the selected catalog. The pipe symbol 238 indicates the cursor position. The user keying in a term into the search field 237 triggers a search against all terms belonging to the selected category. All terms being in said category which match the already entered characters (in this case 'Ben' and) will be displayed in the field 247 in alphabetic order. The user may press the cancel button 245 to abort specifying a particular allergen or he may press, after having specified an allergen, the safe button 246 in order to store the specified data value as part of the data structure.

By selecting the 'drug allergens' tab 233, the user can select a different catalog. According to embodiments of the invention, the user may select a multitude of environmental or other allergens as further data values of the data structure. In case the user selects the 'drug allergens' GUI element 233, the layout of the 'drug allergen' dialog window 230 changes into a new layout which is depicted in FIG. 3.

According to some embodiments, said dialog window 230 is provided by a data structure instantiation module. Depending on the embodiment of the invention, the data structure instantiating module may be a standalone module or a part of the doctor information system or of a communication layer between the doctor information system and the DSS.

FIG. 3 depicts a screenshot of the dialog window 230 of allowing a user to specify a particular drug allergen. The dialog window comprises pane 231 and several sub-areas, e.g. a group of GUI elements for specifying a first ATC level 330, for specifying a second ATC level 331, several additional areas for specifying a third and fourth ATC level (which are indicated for space reasons by three dots) and a further group of UI elements for specifying a fifth ATC level 332. The term 'ATC' is an acronym for 'the anatomical therapeutic chemical classification system with defined daily doses' classification system. The system is an international classification of therapeutic drugs. It comprises five hierarchical levels with 14 category elements within the first hierarchical level.

For each ATC level, a search field 333, 334, . . . , and 335 is provided. GUI element 336, which can be, for example, a drop down menu, a list of selectable GUI elements with a scrollbar or the like, comprises drug allergens corresponding to elements of the highest level of the drug allergen catalog. Upon selection of a particular catalog element by selecting GUI element 339, catalog elements being child nodes of the selected catalog element are displayed in the GUI area 337.

By a cascading series of 5 selections of the user via selectable GUI element 339, 340, . . . , 341, the user can specify an allergen quickly and efficiently. Alternatively, the user may key in search terms directly in the search field 237. The user does not have to enter the complete term. Rather, after having keyed in a small set of characters, a set of terms is suggested in GUI area 241 based on a character matching operation. The user may select one of the suggested terms of area 412 to further speed up the entry of the search term.

Figure 4:
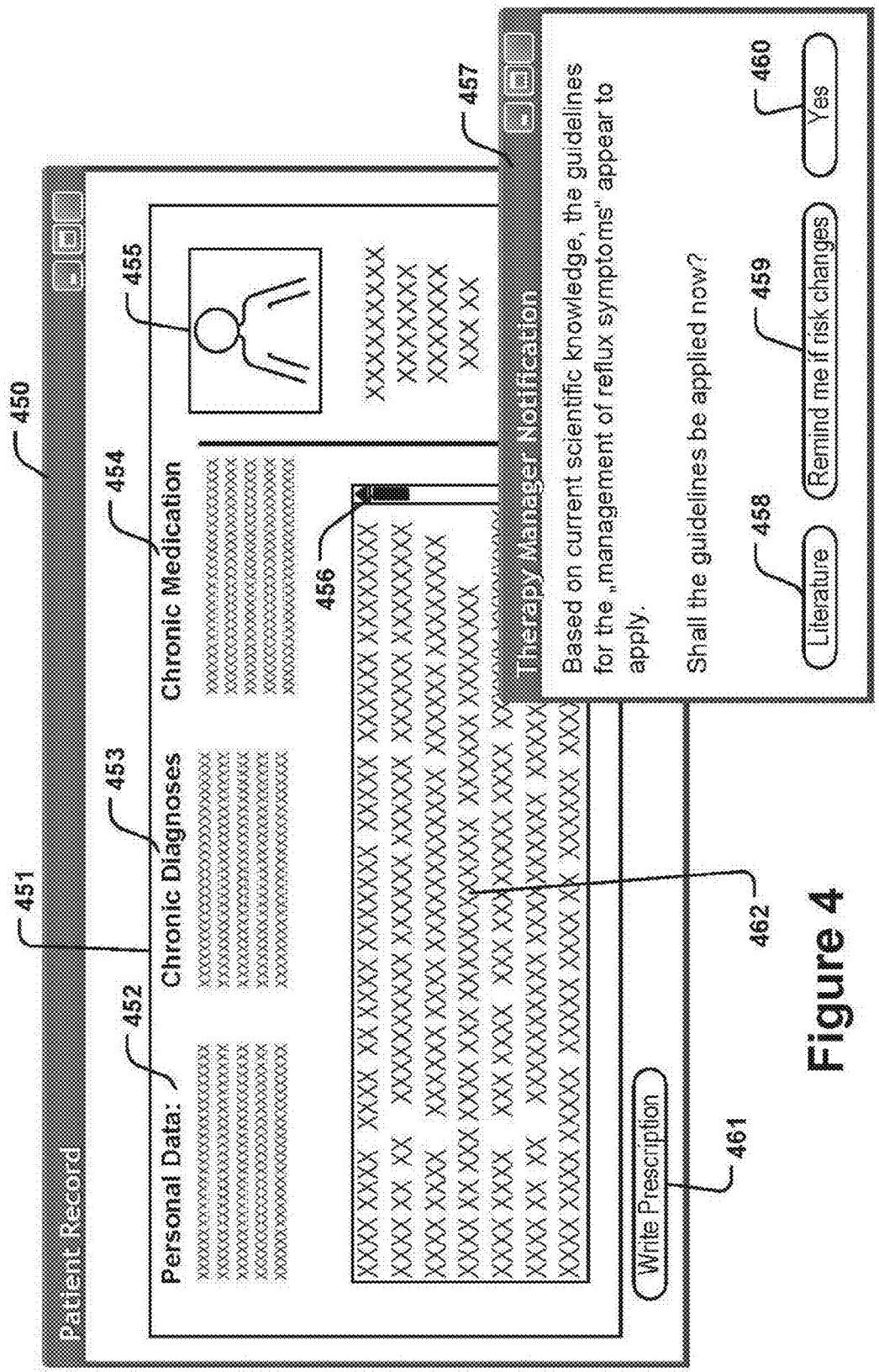
FIG. 4 depicts a dialog window comprising an electronic patient record and a dialog window displaying a medical decision.

FIG. 4 depicts the dialog window 450 of a doctor information system. The dialog window comprises an electronic patient record and displays patient related medical and personal data in GUI areas 452, 453, 454, 455. The medical history of the patient is listed in chronological order in the scrollable GUI pane 462 which comprises a scrollbar 456. Upon a particular event, e.g. the user pressing the 'write prescription' button 461, a data structure comprising medical data values of the patient is instantiated and a message comprising said data structure is sent to a therapy manager module of a DSS. According to some embodiments of the invention, said data structure comprises in addition to the medical data of the patient also personal data such as the name and address of the patient. According to preferred embodiments of the invention, at least the personal data of the patient is pseudomized and/or encrypted. According to further embodiments, in addition to the personal data of the patient, some or all medical data values of the data structure or the whole data structure are encrypted.

The therapy manager module of the DSS receives the submitted data structure from the doctor information system hosted on the same or another processing machine and uses the received medical data as input for calculating a medical decision. According to some embodiments, the DSS is hosted on a server and receives the data structure from a client or another server hosting a doctor information system. According to some embodiments, the DSS calculates, whether an increased risk for a particular diagnosis exists for the patient based on the received data structure. In case calculated risk exceeds a particular threshold value, a message is sent from the therapy manager module of the DSS to the doctor information system. Said message triggers the display of a second dialog window 457, which displays a message created by the therapy manager module. The second dialog window 457 notifies the user that, based on current scientific knowledge and based on the received medical data of the patient, the guidelines for the 'management of reflux symptoms' appear to apply. The user, typically a physician, is prompted to decide whether he wishes to execute the guidelines on the medical data of the patient. In addition, the user is provided with the option to be presented additional literature by pressing button 458. By pressing button 459 a user may choose to be reminded of said guideline at a later stage in case the calculated risk of the patient changes. In case the user clicks the 'yes' button 460, the therapy manager module of the DSS triggers the display of an electronic questionnaire in order to determine whether the patient shows symptoms being indicative of a reflux syndrome. Said electronic questionnaire 530 is displayed in FIG. 5.

Figure 5:
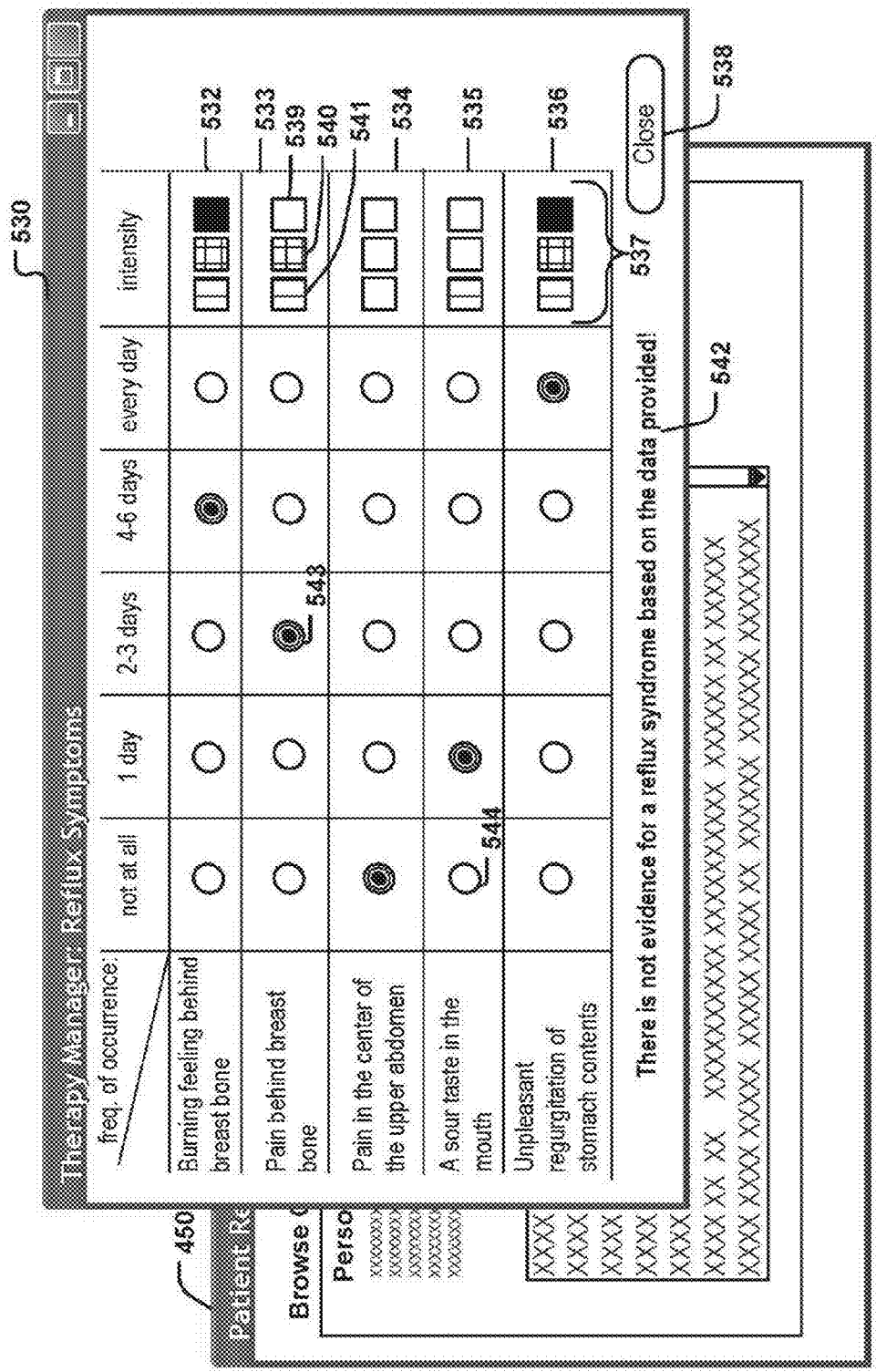
FIG. 5 depicts a dialog window provided by a therapy manager module of a decision support system.

FIG. 5 depicts an exemplary electronic questionnaire 530 allowing the user to enter symptoms, observations, measurement values or other kinds of data which can help in the determination and recognition of a particular syndrome, in this case, a reflux syndrome. The first line of the table comprises several options for specifying the occurrence frequency of a particular symptom, e.g. 'not at all', 'one-day', '2-3 days', '4-6 days' or 'everyday'. The first column comprises a list of symptoms which may indicate the presence of a reflux syndrome, for example 'burning feeling or pain behind the breast bone', 'pain in the centre of the upper abdomen', 'a sour taste in the mouth' or 'unpleasant regurgitation of stomach contents'. The doctor can specify in cooperation with the patient which symptoms apply. The empty light circles, e.g. 544, are unselected radio buttons. The circles comprising a black circle at their centre, e.g. 543, represent the selected radio button. Each row 532-536 represents a particular symptom having an impact, according to the guidelines for the reflux syndrome, on the diagnosis of the reflux syndrome. The intensity of each symptom is graphically indicated by a group of three squares 537. In case the symptom has not been observed at a patient, as the case for symptom 534, none of the three squares is highlighted. In case the symptom has been observed only occasionally, as the case with symptoms 539 and 535, only the first or second square is highlighted with a color being particular to the first or the second square. In case a symptom was observed frequently, as the case with symptoms 532 and 536, all three squares are highlighted.

Figure 6:
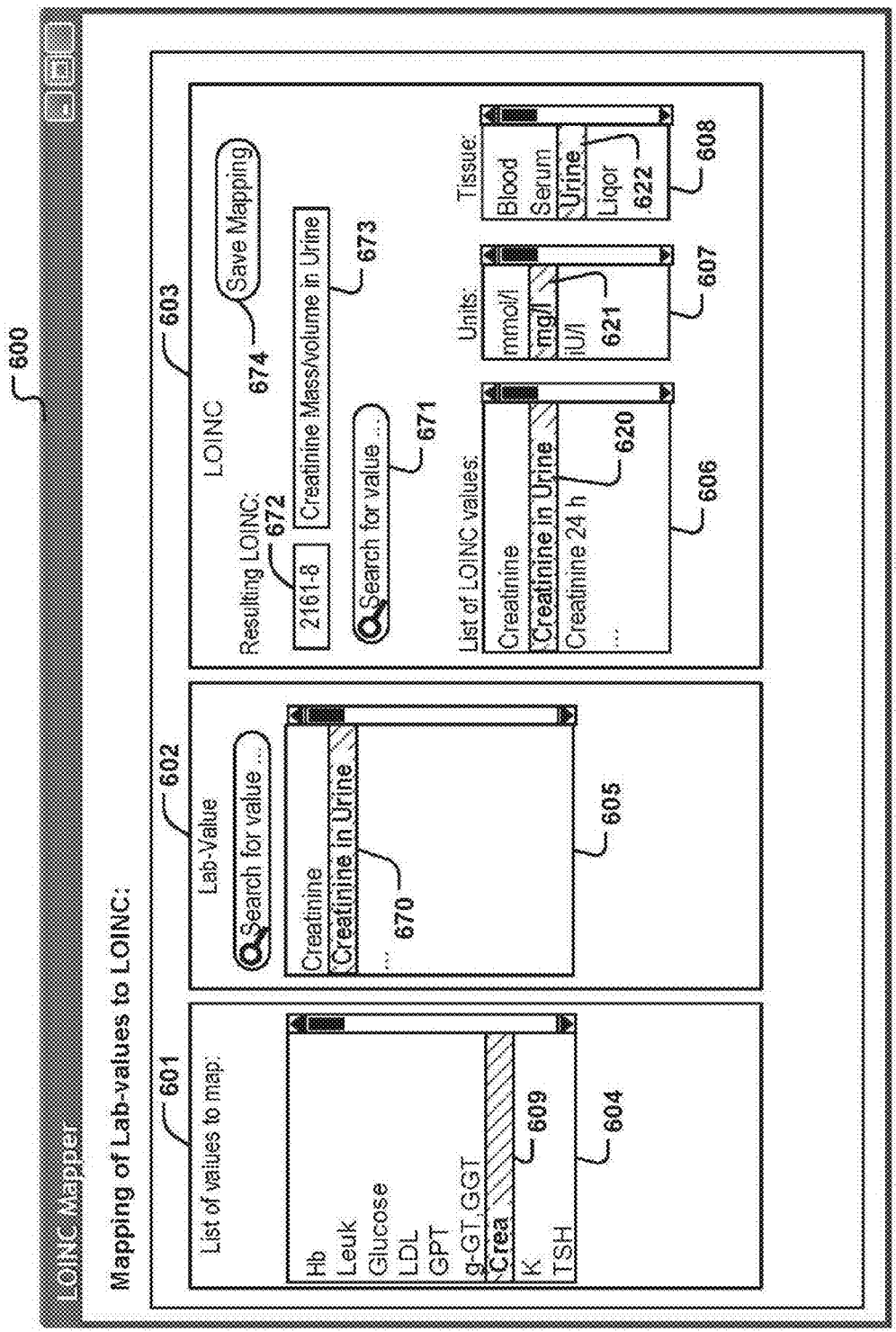
FIG. 6 depicts a graphical user interface provided by the DSI module.

FIG. 6 displays the dialog window 600 allowing a user unskilled in a programming language to specify a mapping of laboratory values to LOINC codes.

It has been observed that a common problem associated with providing laboratory values of a patient to a DSS is a lack of standards. Different laboratories return the measured values in a variety of different systems of units. The situation is further complicated by using, for each laboratory parameter, identifiers of different medical catalogs or non-standardized, lab specific catalog identifiers. For example, the first lab may use the identifier 'Crea' while a second lab may use the identifier 'Krea' to refer to the creatine level. The situation may further the complicated that different laboratories may measure a particular analyte in different tissues or body fluids. Although it is possible for a person skilled in a programming language to write a parser for each output file, most medical practitioners and physicians are unskilled in such a programming language. For said reasons, automatically integrating data values obtained from different labs into one doctor information system this in many cases not possible in current state-of-the-art doctor information systems.

According to embodiments of the invention, the problem is solved by a mapping program module which is operable to read laboratory values provided in any standard file format such as XML or comma-separated files (CSV) and to map at least the biomedical parameters of a data structure according to embodiments of the invention to the LOINC code by means of a GUI, i.e. the dialog window 600. Accordingly, one aspect of said problem solution is an advantageous GUI which will be explained in the following. In a second aspect, said problem is solved by determining a core set of biomedical parameters providing the broadest coverage of diseases affecting a particular population. According to some embodiments, said mapping module is part of the data structure instantiating module. Depending on the embodiment of the invention, the data structure instantiating module may be a standalone module or a part of the doctor information system or of a communication layer between the doctor information system and the DSS.

The mapping program module 746 receives one or more laboratory values (e.g. by reading a file) and presents the received laboratory parameters to the user in a first GUI area 601. The GUI area 601 comprises a list of parameters to map, said parameters being displayed on a scrollable list 604. The list 604 presents the parameters as specified by the laboratory having created the read file. Upon selection of a particular parameter of the first list, e.g. 'Crea' 609, a list of possible LOINC parameters is displayed in GUI area 602 in the scrollable list 605.

The provision of said possible parameters for a selected parameter of the first list is executed automatically and assists a user not skilled in a programming language to map said selected parameter to a parameter of a desired standard, e.g. LOINC. According to some embodiments, on mouse-over a tool tip shows common names, which are often used e.g. as synonyms for a selected parameter, as 'possible parameters'. Said possible parameters may also be presented automatically in a second list 605 for selection by a user. According to some embodiments, the user may use a search function in order to be suggested a list of potential parameters having a similar name as the selected parameter, e.g. which begin with the keyed in characters.

The user can select one of said similarly named parameters, e.g. 'Creatinine in urine' 670.

Upon having selected a particular parameter displayed in the second list 605, the user can specify in GUI area 603 additional values for each dimension of the multi—dimensional LOINC code. In particular, the user can specify in scrollable list 607 the system of units and in scrollable list 608 the tissue or body fluid from which the lab value was derived. The selectable list 606 displays the selected LOINC method and allows the user to switch to another related LOINC method. The text field 672 displays the automatically derived LOINC code which depends on the items having been selected by the user in the selectable list 606-608. Text field 673 displays the LOINC code in a human readable form. The LOINC code displayed in text fields 672 and 673 this dynamically updated upon each selection of the user in any of the lists 604-608. Alternatively, the search field 671 allows a user to enter a LOINC-code directly by searching for the human-readable identifier of a particular LOINC-code. As a result, a data value can be represented by a standard-conform LOINC-code before it is used for instantiating a data structure.

As a result, by means of said dialog window 600, a user without any programming skills is able to transform laboratory measurements provided by any laboratory into a standard LOINC code. According to embodiments of the invention, laboratory values are received directly from a lab device or from a lab, e.g. via the Internet, term e-mail, from a laboratory information system (LIS) or from the middleware of a hospital. In case the received laboratory values are not provided in the appropriate format, they are mapped e.g. via dialog window 600 and transformed to a data value conforming to the LOINC code scheme. The mapped LOINC data values are used, alone or in combination with additional data values, to instantiate a data structure. The data structure can be used as input for a DSS.

According to other embodiments, the biomedical parameters of the data structures I-IV are mapped to other codes than the LOINC code. The GUI of said embodiments is adapted accordingly.

Figure 7:
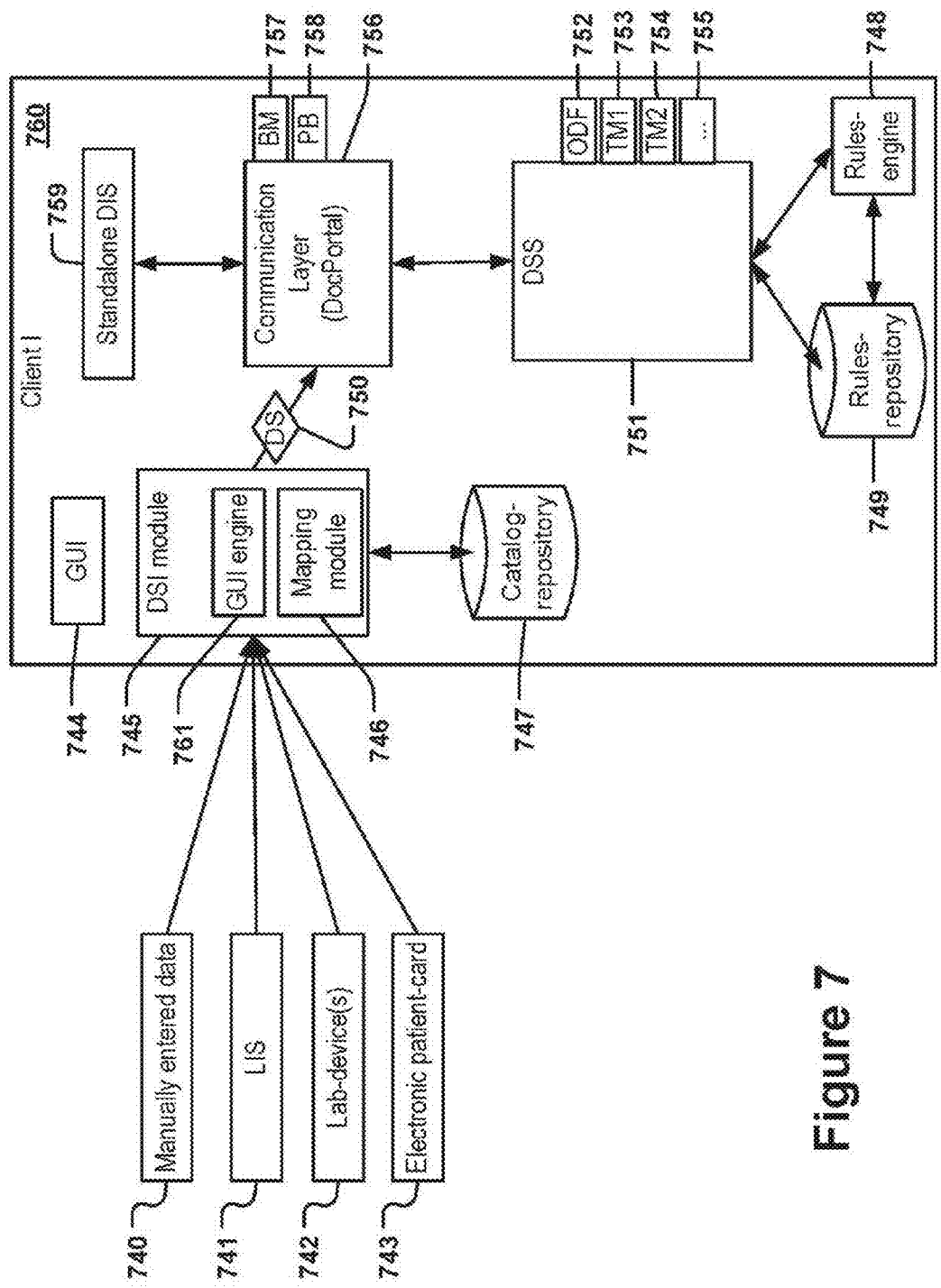
FIG. 7 depicts a client computer system comprising a doctor information system and a medical decision support system.

FIG. 7 depicts a client-computer system 760 which comprises a stand-alone doctor information system 759 and a software module 745 for instantiating a data structure 750. Said data structure 750 is used as input by a DSS 751 which is also installed on the client machine 760.

The client computer system 760 is operable to receive patient related data from a variety of data sources 740-743. Patient related—as well as medical data of a patient can be entered manually, e.g. by physician during the patient interview, as indicated by data source 740. Said data may likewise be received from a laboratory information system (LIS) 741. Laboratory data of the patient may also be received directly from one or more lab devices 742 connected to the client machine 760. Patient related data may likewise be read from an electronic patient card 743.

Patient related data is received from one or more data sources by a DSI module (data structure instantiation module) 745. The function of the DSI module is to facilitate the entry of patient related data values by a user and to facilitate the instantiation of a data structure DS 750. Depending on the embodiment, the DSI module may be an independent software module or an integral part of the doctor information system 759. According to further embodiments (not shown), the DSI module may be hosted on a different computer and the generated data structure 750 may be provided to the stand-alone DIS 759 via a network or other portable storage medium such as a USB stick, a CD-ROM, or the like.

According to embodiments of the invention, the DSI module 745 comprises a GUI engine 761 and a mapping module 746 and has access to a catalog repository 747. The catalog repository may be a data file or relational database and may comprise, for example, drug allergen catalogs, environmental allergen catalogs or other catalogs which may be presented to the user via a graphical user interface 744. The GUI engine 745 facilitates the entry of patient related data, e.g. allergens, by reading catalog information from the catalog repository 747 and by providing the user with the dialog window 230 as depicted in FIGS. 2 and 3. By means of dialog window 230 the user can quickly and easily select a particular catalog item and use the machine-readable identifier for instantiating the data structure 750.

According to embodiments wherein the DSI module further comprises a mapping module 746, the user is provided with means for mapping XML or CSV format conform laboratory data values to data values specified according to the LOINC coding scheme. The mapping is executed semi-automatically via a dialog window 600 as depicted in FIG. 6. Said dialog window 600 is also presented via a GUI 744. Depending on the embodiment of the invention, the GUI 744 can be any kind of electronic display, in particular a screen of a computer or notebook.

After having instantiated the data structure 750 comprising the minimum number of patient related medical data values to cover a predefined percentage of diseases of a population, said data structure 750 is used as input for a communication layer 756. Communication layer 756, also referred to as 'DocPortal', is a software application or module which is interoperable with a doctor information system DIS 759 and is in addition interoperable with DSS 751. The communication layer 756 comprises several modules, e.g. the 'bubble manager' module BM 757 and the portal browser module PB 758. According to preferred embodiments, the modules 757, 758 are plug-ins of the communication layer 756. The PB module receives commands and data from one or more DSS modules 752-755.

The ODF module 752 is the module of the DSS which is operable to receive data comprised in a data structure according to embodiments of the invention and to predict the risk of the patient whose biomedical parameter values were contained in said data structure for a particular set of diagnoses. A first therapy management module TM1 753 is responsible for determining, based on the received data structure, the optimum therapy scheme for a first particular diagnosis. A second therapy management module TM2 754 is responsible for determining, based on the received data structure, the optimum therapy scheme for a second diagnosis or for a set of second diagnoses.

Depending on the embodiment of the invention, the DSS may comprise additional DSS modules for the prediction of future diagnoses, for the calculation of the current risk of the patient to be affected by one or more medical conditions, for monitoring a disease and for providing a physician with instructions on how to treat a disease and which medication to be prescribe given the current medication of the patient or known drug intolerances.

The ODF module 752 and one or more other decision support modules of the DSS receive the data structure 750 from the communication layer 756 and use the data values contained in the received data structure for calculating a medical decision. The medical decision is returned by the DSS to the communication layer 756 and forwarded to the PB module 758. The PB module uses the information contained in the received medical decision to initiate the instantiation and display of pop-up messages and to specify the data content of said pop-up messages. The task of displaying the specified pop-up window and managing its appearance on a graphical user interface is performed by the BM module 757. According to preferred embodiments of the invention, the DSS modules can be independently operated and individually addressed for calculating a medical decision as separate functional parts of the DSS. Accordingly, one or more modules may be inactivated or activated (e.g. by deinstalling or installing a module) by a user.

The modularity of the DSS is highly advantageous, as a user is allowed to add or remove additional modules and, correspondingly, different functions for calculating a medical decision, at his discretion. Depending on the embodiment, said user may be a physician or an operator of the DSS.

The decision support system 751 is operable to read rules from rules repository 749 and to control a rules engine 748. The rules engine applies one or more rules read from the rules repository on the data values contained in the data structure DS 750 received from the communication layer 756. A rule can be, for example, the computer-interpretable expression: 'if gender=male and age>11 and age<23 and glucose level in blood<Xmg/ml and conditions Ca, Cb and Cd apply to the biomedical data values of a patient, then: clinical suspicion of Disease Y'. If said rule applies to the data of a patient, the DSS may return the diagnosis 'Disease Y' as a result of processing the biomedical data values of a patient provided by the data structure. Ca, Cb and Cd are further conditions which can be checked on the plurality of biomedical data values provided by the received data structure.

The embodiment of a client computer system 760 depicted in FIG. 7 depicts the DSS system 751 and the communication layer 756 is independent software components. According to other embodiments of the invention, the communication layer and the decision support system may constitute one large, single software system comprising one or more DSS modules for calculating one or more medical decisions and additional modules 757, 758 for controlling the display of said medical decisions to a user.

Figure 8:
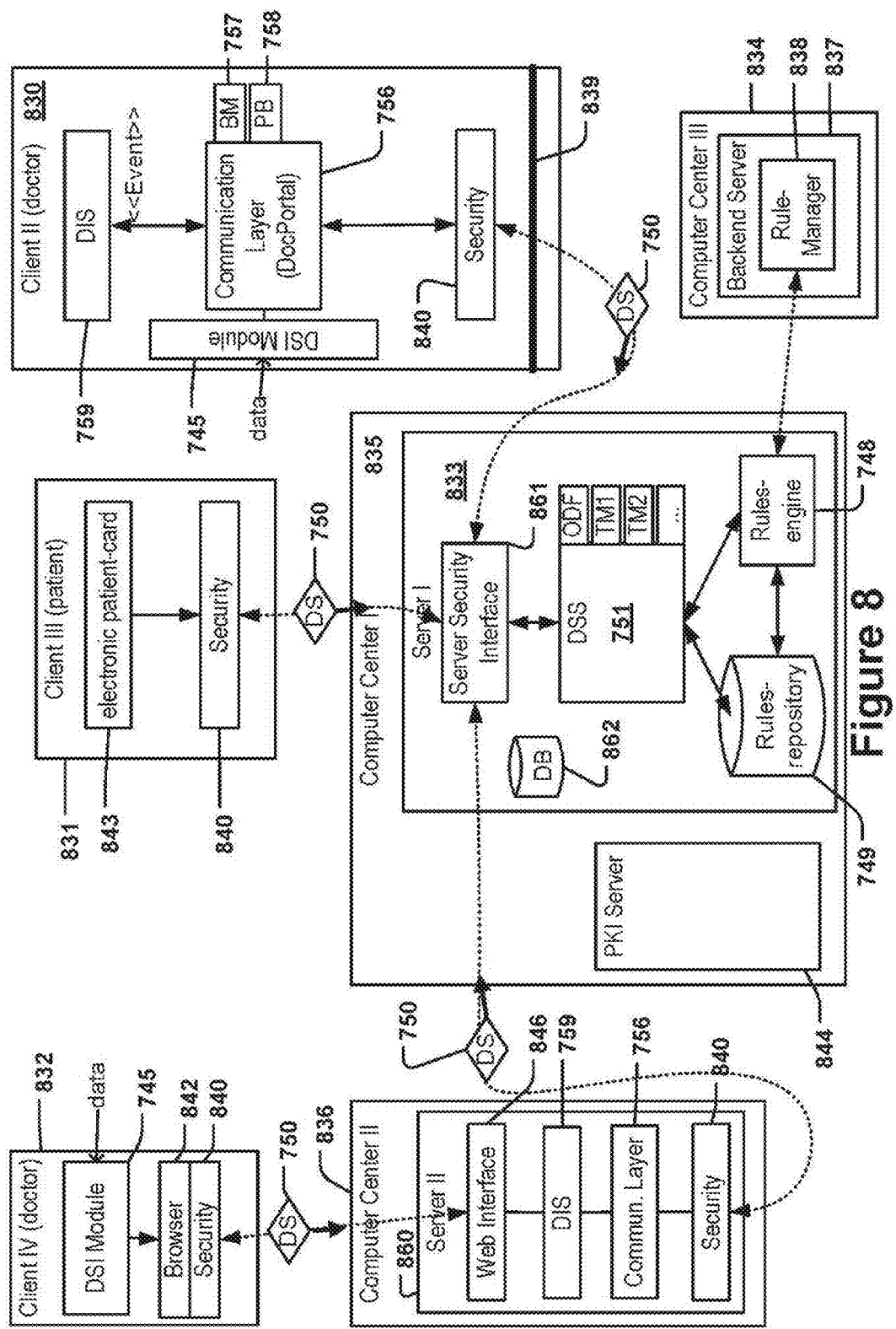
FIG. 8 depicts multiple clients and servers, the servers being distributed to different computer centers.

FIG. 8 depicts a distributed computer system comprising multiple clients 830, 831, 832, multiple computer centers 834, 835, and 836, and multiple servers 860, 844, 833, and 837. FIG. 8 depicts a remote medical decision support system 751 which can be accessed by a variety of client machines of different types. Client machine 830 largely resembles the computer system depicted and explained in FIG. 7. The client system 830 comprises a doctor information system DIS 759. The client system 830 further comprises a data structure instantiation module 745 which is operable to receive patient related data from various sources, e.g. from an LIS, or from a user interface via which a user, in particular a physician, can enter patient related data. According to embodiments of the invention, the DSI module is interoperable with the communication layer 756 or is implemented as integral part of said communication layer. The communication layer comprises one or more modules 757, 758 controlling the appearance of pop-up messages which are displayed to a user via a graphical user interface.

The communication layer 756 is operable to send and receive data from server 833 via interface 840. Interface 840 is responsible for guaranteeing the privacy of the exchanged data, in particular person related data and medical data of a patient. The client system 830 is protected from illegitimate access by a firewall 839. The dotted lines indicate network connections which can be, but not necessarily are, of low bandwidth. A data structure 750 is specified and instantiated by the DSI module 745 and sent to the server 833 for calculating a medical decision based on the data structure.

The small size of the parameter set contained in the data structure 750 allows the rapid exchange of data and the rapid calculation of a medical decision by the decision support system and thereby allows the creation of the distributed decision support system which is able to interoperate with various client computers in a dynamic and fast way.

The 'server security interface' 861 located on the server 833 is operable to receive, and optionally also to decrypt the received data structures for providing an unencrypted form of the data structure as input for the DSS 751. Depending on the embodiment, the server security interface is also operable to store the received data structure into database 862. Accordingly, the DSS may receive the data structure from a client computer system via interface 861 or may read a data structure from database 862. According to preferred embodiments, the DSS uses interface 861 in the reading process for decrypting the data contained in the data structure for calculating a decision on a decrypted data structure. As the size of the set of parameters contained in data structure 750 is small, the DSS is operable to quickly calculate a result, e.g. the risk for a particular disease, based on the limited set of parameters. The decision support system 751 comprises a multitude of independent decision support modules ODF, TM1, TM2 and others. Each module is responsible for the calculation of a decision based on rules which are stored in the rules depository 749 and which are executed by rules engine 748. According to preferred embodiments, the rules engine is interoperable with the rule manager 838 which is, depending on the embodiment, hosted on the same server 833 as the rules engine 748 or on a different server 837. According to embodiments, the servers 833, 860, 837 are located in the same computer center 835. According to other embodiments, said servers are hosted at different computer centers 834-836.

A user connected to the rule manager is able to create or modify a rule stored and managed by the rules engine 748. The decision support modules ODF; TM1, TM2 can be dynamically uploaded to the decision support system 751. They can also be dynamically exchanged by updated versions of the decision support module. It is also possible to deactivate or deinstall any of the decision support modules at runtime of the decision support system. This feature in combination with the client-server architecture is highly advantageous as it allows to reduce the workload associated with keeping the decision support system up to date.

As knowledge grows rapidly in the medical domain, frequent updates of the rules are therefore required. Hosting the medical decision support system on a remote server 833 in a remote computer centre 835 has the advantage that a multitude of remote clients 830, 831, or 832 can make use of the medical decisions provided by the distant decision support system while it is not necessary to keep each client up to date with new medical knowledge. Provided a client has the necessary interfaces, e.g. the security interface 840, a client submitting a data structure 750 to the DSS 751 is operable to receive the medical decision provided by the decision support system as a response.

The PKI server 844 provides a public key infrastructure which is required by the server security interface 861 and the security interfaces 840 to allow a secure encryption and decryption of sensitive medical data exchanged via an unsecure network. In particular, the PKI infrastructure allows third parties to check the authenticity of the public key belonging to an asymmetric key pair used for pseudonymization or encryption of the data structure as will be explained in greater detail in description of FIGS. 10-13.

The program logic comprised in client 830 can further the distributed to more than one client device as is the case for the combination of client 832 and server 860. Client 832 does not comprise a doctor information system 759. Client 832 merely comprises a browser 842 being operable to display graphical user interface information provided by a doctor information system 759 hosted on server 860. Browser 842 can be a standard web browser operable to display e.g. standard web page formats such as HTML provided by web interface 846.

According to other embodiments, browser 842 may not be a standard web-browser but rather a particular software component which has to be installed on a standard computer system and which is operable to exchange data with the web interface 846 provided by the doctor information system 759 on the server 860. In a user of client system 832 may specify and instantiate a data structure 750 on the client device 832 and send that data structure via 'security interface' or 'security module' 840 to the web interface 846. The instantiation of the data structure may be accomplished by making use of program logic provided by the doctor information system 759 and/or the communication layer 756 hosted on server 860. According to some embodiments of the invention, the client 832 provides biomedical parameters of a patient and the data structure 750 is created on server 860.

The data structure is transferred from server 860 via interface 840 to the server-side security module 861 of server 833.

After having calculated a medical decision based on the received data structure by the DSS system 751, the medical decision, e.g. a calculated risk for a diagnosis, is returned to the communication layer 756 of server 860. The communication layer processes the received results and specifies one or more pop-up messages which are displayed by browser 842 of the client device 832. The combination of client 832 and server 860 is particularly advantages for clients which have only very limited processing power such as netbooks or mobile phones as it is possible to install only a light-weight component of a doctor information system (the browser being responsible solely for visualization tasks) on the client. For other, computationally more demanding tasks of the doctor information system, the processing power of server 836 is used. The program logic of the doctor information system which might require a more powerful processor and sufficient working memory is hosted on the server which typically comprises powerful hardware resources. In case the security interface 840 of client 832 guarantees the privacy of the data of the data structure submitted over the network, the security interface 840 on the server 860 may not be necessary for every embodiment as the data structure may already be received by server 860 in a pseudonymized and potentially also encrypted form. According to other embodiments, the data structure may be instantiated on the server 860 e.g. based on data keyed in by a user in browser 842 and submitted via the network to the server 860. As the network connection from server 860 to server 833 may be unsecure, the security interface 840 on server 860 ensures that sensitive data is submitted only in a pseudonymized and optionally also encrypted form.

In case the data connection between client 832 and server 860 is very slow, it may however be more appropriate to use the client 830 which comprises a doctor information system 759 and a communication layer 756 for communicating with the decision support system 751. In this case, information provided by the doctor information system which shall be displayed to a user needs not to be communicated through a potentially slow network in client variant 830.

According to some embodiments of client 832, the client further comprises the data structure instantiation module for instantiating a data structure 750.

According to further embodiments, the client device 831 comprises an interface for reading an electronic patient card 843 and creating a data structure 750 based on the parameter values read from that patient card. The data structure can be provided via security interface 840 to the remote decision support system. Client 831 does not necessarily comprise a graphical user interface for displaying the medical decisions calculated by the remote DSS 751. According to some embodiments, the data structure provided by client 831 is used to calculate a medical decision and to store patient related data contained in the data structure in combination with the calculated medical decision to a central data repository 862 hosted on server 833 or another remote server. The patient related data and the associated medical decisions may be requested and displayed by another client device having the appropriate access rights.

FIG. 9 depicts a data structure 950 specified in XML format. At least some XML elements comprising a medical parameter value of a patient also comprise or have assigned an XML element specifying a timestamp value 951. According to some embodiments, one or more biomedical parameter values contained in an instance of the data structure may comprise additional property values, which can also be provided to the DSS as input. For one single record (parameter value) of the biomedical parameter 'smoking history', for example, additional properties are taken from the group comprising 'Date', 'Begin of smoking', 'end of smoking', 'cigarettes per day' and others.

Figure 10:
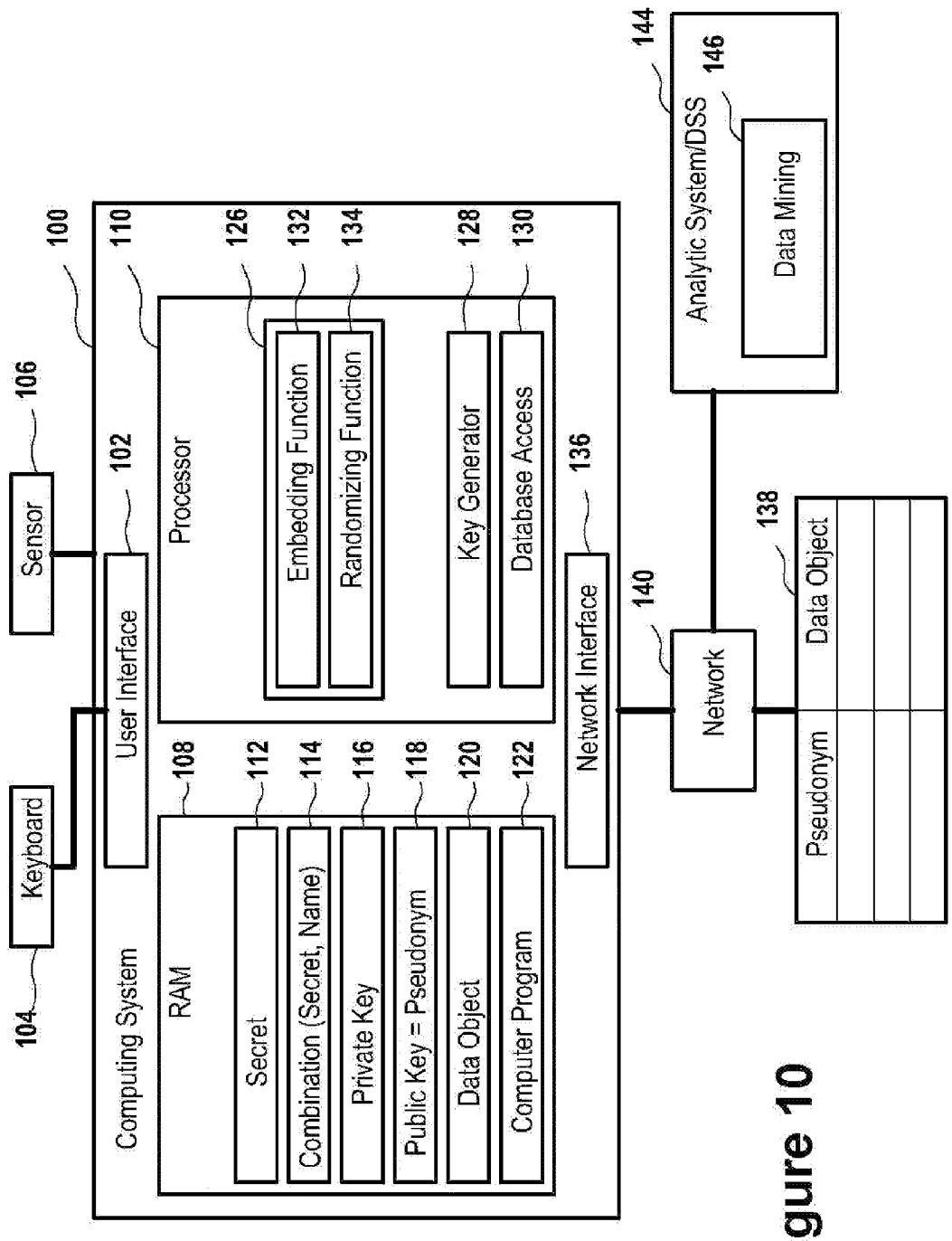
FIG. 10 is a block diagram of a computer system comprising a module for pseudonymizing a data structure.

FIG. 10 shows a computer system 100 that has a user interface 102 for a user's entry of a user-selected secret that is designated as $s_T$ in the following. For example, a keyboard 104 may be coupled to the computer system 100 for entry of $s_T$. Instead of a keyboard 104 a touch panel or another input device can be coupled to the computer system 100 for entry of $s_T$. In addition, a sensor 106 can be coupled to the computer system 100 such as for capturing biometric data from a biometric feature of the user. For example, the sensor 106 may be implemented as a fingerprint sensor in order to provide biometric fingerprint data to the computer system 100. The pseudonymization and access key generation described for computer system 100 in greater detail for any kind of data object can be executed, according to embodiments of the invention, by a client side security module 840 installed on any of the clients 830-832. According to said embodiments, a data structure, e.g. of types I-IV is used as data object for which a pseudonym or access key is calculated by said security module.

According to embodiments of the invention, the steps for calculating a pseudonym discussed in FIG. 10 are provided by a client side security module 840. The PKI Server 844 may be used to guarantee authenticity of the A public parameter, such as the user's name or email address, can also be entered into the computer system 100 via the keyboard 104 or otherwise. For example, a personal set $V_{T,i}$ containing at least one user-specific public parameter, such as the user's name or email address, is entered into the computer system 100 by the user $T_i$.

The computer system 100 has a memory 108, such as a random access memory, and at least one processor 110. The memory 108 serves for temporary storage of the user-selected secret $s_T$ 112, a combination 114 of $s_T$ 112 and $V_{T,i}$, a private key 116, a public key 118 that constitutes a pseudonym of the user $T_i$, and a data object 120, such as a medical data object containing medical data related to the user $T_i$. Further, the memory 108 serves for loading computer program instructions 122 for execution by the processor 110.

The computer program instructions 122 provide an embedding and randomizing function 126, a key generator 128 and may also provide a database access function 130 when executed by the processor 110.

The embedding and randomizing function 126 may be provided as a single program module or it may be implemented by a separate embedding function 132 and a separate randomizing function 134. For example, the embedding function 132 or an embedding component of the embedding and randomization function 126 provides the combination 114 by concatenating $s_T$ and the user's name or by performing a bitwise XOR operation on $s_T$ and the user's name.

In one implementation, the embedding and randomizing function 126 implements symmetric encryption provided by a symmetric cryptographic algorithm, e.g. AES, using a user-specific symmetric key for encryption of the user-selected secret 112. This provides both embedding and randomizing of $s_T$ 112.

In another implementation, the embedding function 132 is implemented by a binary cantor pairing function for embedding $s_T$ 112 and $V_{T,i}$, and the randomizing function 134 is implemented by AES encryption using a symmetric key that is the same for the entire set of users T.

In still another embodiment the embedding and randomizing function 126 is implemented by two different hash functions and a random number generator (cf. the embodiment of FIGS. 3 and 4).

The key generator 128 serves to compute public key 118 using elliptic curve cryptography (ECC). The private key 116 is multiplied by a base point given by the domain parameters of the elliptic curve which provides the public key 118. By varying the base point and leaving the other domain parameters of the elliptic curve unchanged multiple pseudonyms can be computed for the user $T_i$ on the basis of the same secret $s_T$.

The computer system 100 may have a network interface 136 for coupling the computer system 100 to a database 138 via a communication network 140, such as the Internet. The database access function 130 enables to perform a write and a read access for accessing the data object 120 stored in the database 138 using the public key 118, i.e. the user's pseudonym, as a database access key, e.g. a primary key or candidate key value that uniquely identifies tuples in a database relation. The data object 120 can be, for example, the data structure 750 or a combination of said data structure 750 and a medical decision calculated for said data structure.

Further, an analytic system 140, such as a decision support system (DSS) can be coupled to the database 138 such as via the network 140. The analytic system 144 comprises a component 146 for analyzing the data objects of the users T which are stored in the database 138, such as by data mining or data clustering. According to other embodiments depicted in FIG. 8, said data is stored to database 862 and the DSS module 751 executes the function of the analytic system 140.

In one application the data objects stored in the database 138 contain medical data of the various users. By analyzing the various data objects using techniques such as data mining and/or data clustering techniques medical knowledge can be obtained. For example, data clustering may reveal that certain user attributes contained in the medical data increase the risk for certain diseases.

For generating a pseudonym $p_{T,i}$ for a user $T_i$ based on the secret $s_T$ 112 and domain parameters $D_i$ containing a base point for the elliptic curve cryptography the following steps are executed by the computer system 100 in operation:

The user $T_i$ enters his or her user-selected secret $s_T$ 112 such as via the keyboard 104. In addition, the user may enter at least one public parameter $V_{T,i}$ such as his name or email address via the keyboard 104 or otherwise. Such a public parameter $V_{T,i}$ may also be permanently stored in the computer system 100.

The secret $s_T$ 112 is temporarily stored in memory 108. Upon entry of the secret $s_T$ 112 the embedding function 132 or the embedding component of the embedding and randomizing function 126 generates the combination 114 of the secret $s_T$ 112 and the public parameter $V_{T,i}$. The resultant combination 114 is temporarily stored in the memory 108.

Next, the randomizing function 134 or the randomizing component of the embedding and randomizing function 126 is invoked in order to calculate the private key 116 on the basis of the combination 114. The resultant private key 116 is temporarily stored in memory 108. In the next step, the key generator 128 is started for computing the public key 118 by multiplying the base point contained in the domain parameters D, of the elliptic curve being used by the private key 116.

The public key 118, i.e. the pseudonym $p_{T,i}$, is stored in memory 108. The secret $s_T$ 112, the combination 114 as well as the private key 116 as well as any intermediate result obtained by execution of the embedding and randomizing function 126 and the key generator 128 are then erased from the memory 108 and/or the processor 110. As a consequence, there is no technical means to reconstruct the assignment of the resultant pseudonym to the user $T_i$ as only the user knows the secret $s_T$ 112 that has led to the generation of his or her pseudonym $p_{T,i}$. A data object 120 containing sensitive data of the user $T_i$, such as medical data, can then be stored by execution of the database access function 130 in the pseudonym database 138 using the pseudonym $p_{T,i}$ as a database access key, e.g. a primary key or candidate key value that uniquely identifies tuples in a database relation.

The user-selected secret $s_T$ 112 may be obtained by combining a user-selected password or secret key with biometric data of the user $T_i$ that is captured by the sensor 106. For example, a hash value of the user-selected password or secret key is calculated by execution of respective program instructions by the processor 110. In this instance the hash value provides the user-selected secret $s_T$ 112 on which the following calculations are based.

A plurality of users from the public set of enrolled participants T may use the computer system 100 to generate respective pseudonyms $p_{T,i}$ and to store data objects containing sensitive data, such as medical information in the database 138 as it has been described above in detail for one of the users $T_i$ by way of example.

For reading the data object of one of the users $T_i$ from the database 138 the user has to enter the secret $s_T$ 112. Alternatively, the user has to enter the user-selected password or secret key via the keyboard 104 and an acquisition of the biometric data is performed using the sensor for computation of a hash value that constitutes $s_T$ 112. As a further alternative, the secret key is read by the computer system from an integrated circuit chip card of the user. On the basis of $s_T$ 112 the pseudonym can be computed by the computer system 100.

The pseudonym is then used for performing a database read access on the database 138 in order to read one or more data objects 120 that are stored in the database 138 for that user $T_i$. After the database access operation has been performed the secret $s_T$ 112, the combination 114, the private key 116 and the public key 118 are erased from the computer system 100 as well as any intermediate computational results.

Figure 11:
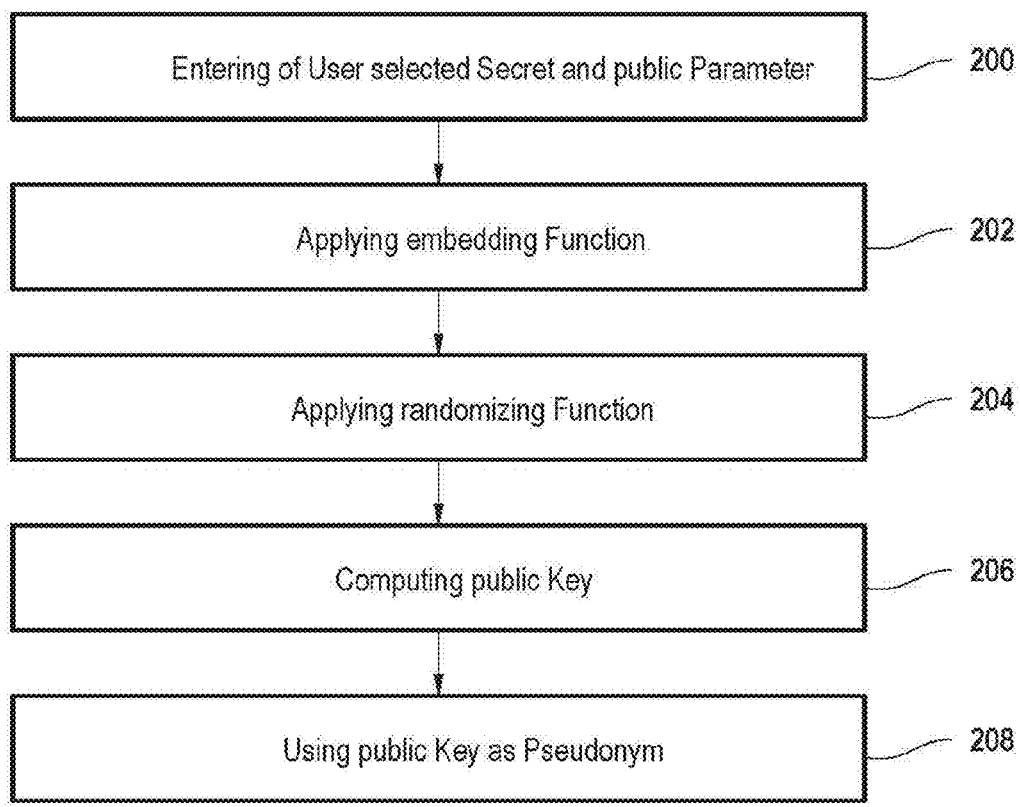
FIG. 11 is a flowchart being illustrative of a further method for providing a pseudonym.

FIG. 11 shows a corresponding flowchart.

In step 200 the user $T_i$ enters his or her user-selected secret $s_T$ and public parameter $V_{T,i}$. In step 202 $s_T$ and $V_T,i$ are combined to provide the first combination by the embedding function (cf. embedding function 132 of FIG. 10). Next, the randomizing function (cf. randomizing function 134 of FIG. 10). is applied on $s_T$ and $V_{T,i}$ in step 204 which provides a private key. As an alternative, an embedding and randomizing function is applied on $s_T$ and $V_{T,i}$ which provides the private key.

In step 206 a public key is computed using the private key obtained in step 204 and the public key is used in step 208 as a pseudonym of the user $T_i$. For example the pseudonym may be used as a database access key, e.g. a primary key or candidate key value that uniquely identifies tuples in a database relation for storing a data object for the user $T_i$ in a database with pseudonymous data (cf. database 138 of FIG. 1 or database 862 of FIG. 8).

Figure 12:
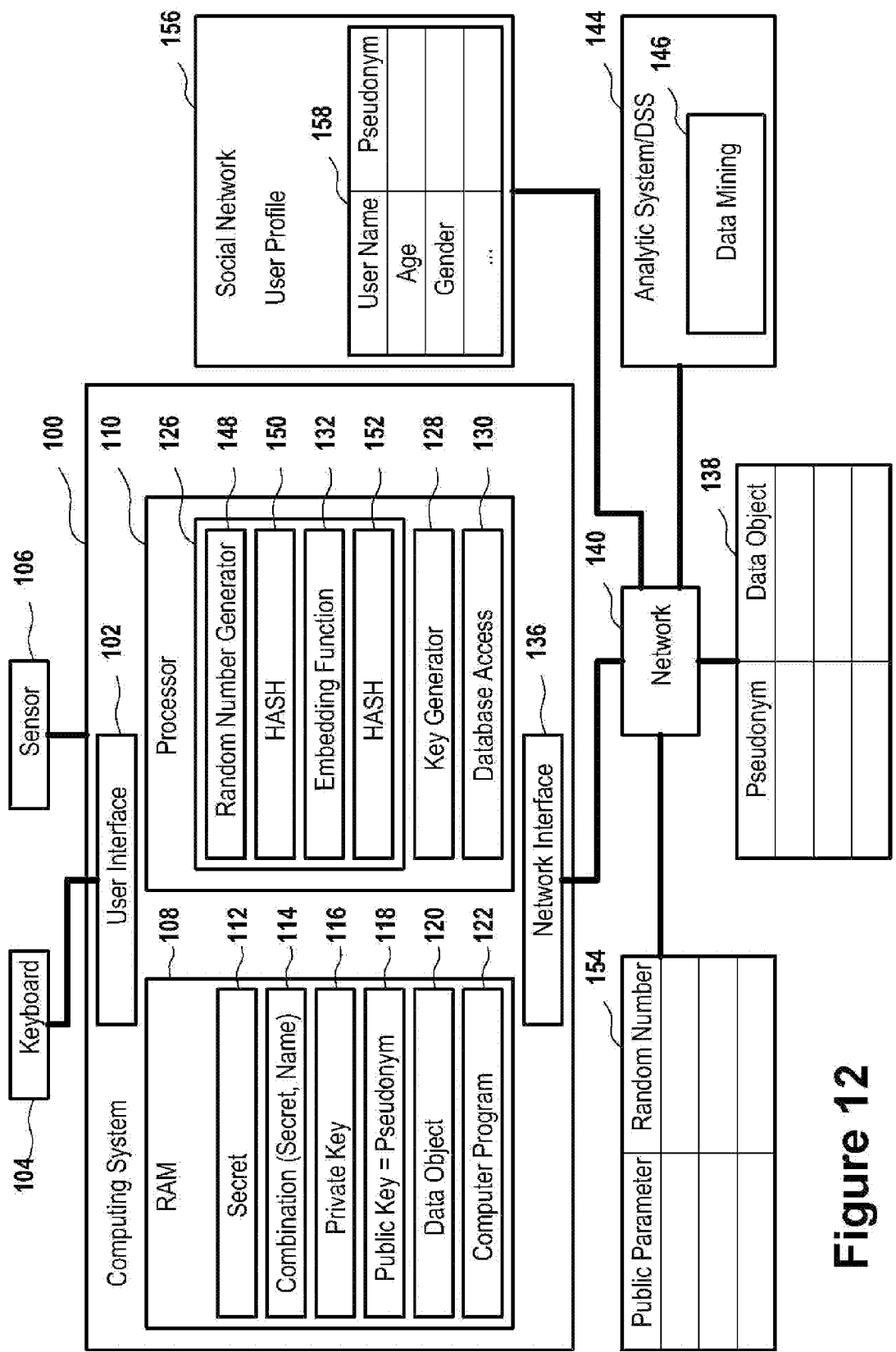
FIG. 12 is a block diagram of a further computer system comprising a module for pseudonymizing a data structure.

FIG. 12 shows a further embodiment of computer system 100. In the embodiment considered here the embedding and randomizing function 126 comprises an embedding function 132, a random number generator 148, a first hash function 150 and a second hash function 152. In the embodiment considered here the computation of the private key 116 based on $s_T$ 112 may be performed as follows:

The first hash function 150 is applied on the user-selected secret $s_T$ 112. This provides a first hash value. Next, a random number is provided by the random number generator 148. The random number and the first hash value are combined by the embedding function 132 to provide the combination, i.e. the embedded secret $s_T$ 112.

The combination of the first hash value and the random number can be obtained by concatenating the first hash value and the random number or by performing a bitwise XOR operation on the first hash value and the random number by the embedding function 132. The result is a combination on which the second hash function 152 is applied to provide a second hash value. The second hash value is the private key 116 on which the calculation of the public key 118 is based.

Dependent on the implementation it may be necessary to determine whether the second hash value fulfils one or more predefined conditions. Only if such conditions are fulfilled by the second hash value it is possible to use the second hash value as the private key 116 for the following computations. If the second hash value does not fulfill one or more of the predefined conditions a new random number is provided by the random number generator 148 on the basis of which a new second hash value is computed which is again checked against the one or more predefined conditions (cf. the embodiment of FIG. 13).

The random number on the basis of which the private key 116 and thereafter the public key 118 has been computed is stored in a database 154 that is coupled to the computer system 100 via the network 140. The random number may be stored in the database 154 using the public parameter $V_{T,i}$ as the database access key for retrieving the random number for reconstructing the pseudonym at a later point of time.

The user $T_i$ may use the pseudonym provided by the computer system 100 for his or her registration in an anonymous online community 156 e.g. a social network. For registration the user $T_i$ creates his or her user profile 158 by entering the pseudonym 118 as the username such that the various private data entered into the user profile 158 remain private even though they are published in the online community 156 due to the fact that the assignment of the pseudonym to the user $T_i$ is stored nowhere and cannot be reconstructed by technical means without knowledge of the user-selected secret $s_T$ 112.

For reconstructing the pseudonym the user has to enter his or her user-selected secret $s_T$ 112 into the computer system on the basis of which the first hash value is generated by the hash function 150 and the combination 114 is generated by the embedding function 132 or the embedding component of the embedding and randomizing function 126 using the first hash value and the random number retrieved from the database 154.

Depending on the implementation, the user may also need to enter the user's public parameter $V_{T,i}$. A database access is performed using the user's public parameter $V_T,i$ as a database access key, e.g. a primary key or candidate key value that uniquely identifies tuples in a database relation, in order to retrieve the random number stored in the database 154.

In other words, the reconstruction of the private key 116 is performed by applying the embedding function 132 on the first hash value obtained from the user-selected secret $s_T$ 112 and the retrieved random number which yields the combination 114. The first hash value is combined with the random number retrieved from the database 154 by the embedding function 132 to provide the combination onto which the second hash function 152 is applied which returns the private key 116, out of which the public key 118, i.e. the pseudonym, can be computed. After the user $T_i$ has recovered his or her pseudonym a database access for reading and/or writing from or to the database 138 may be performed or the user may log into the online community 156 using his or her pseudonym for anonymous participation in the online community 156.

Figure 13:
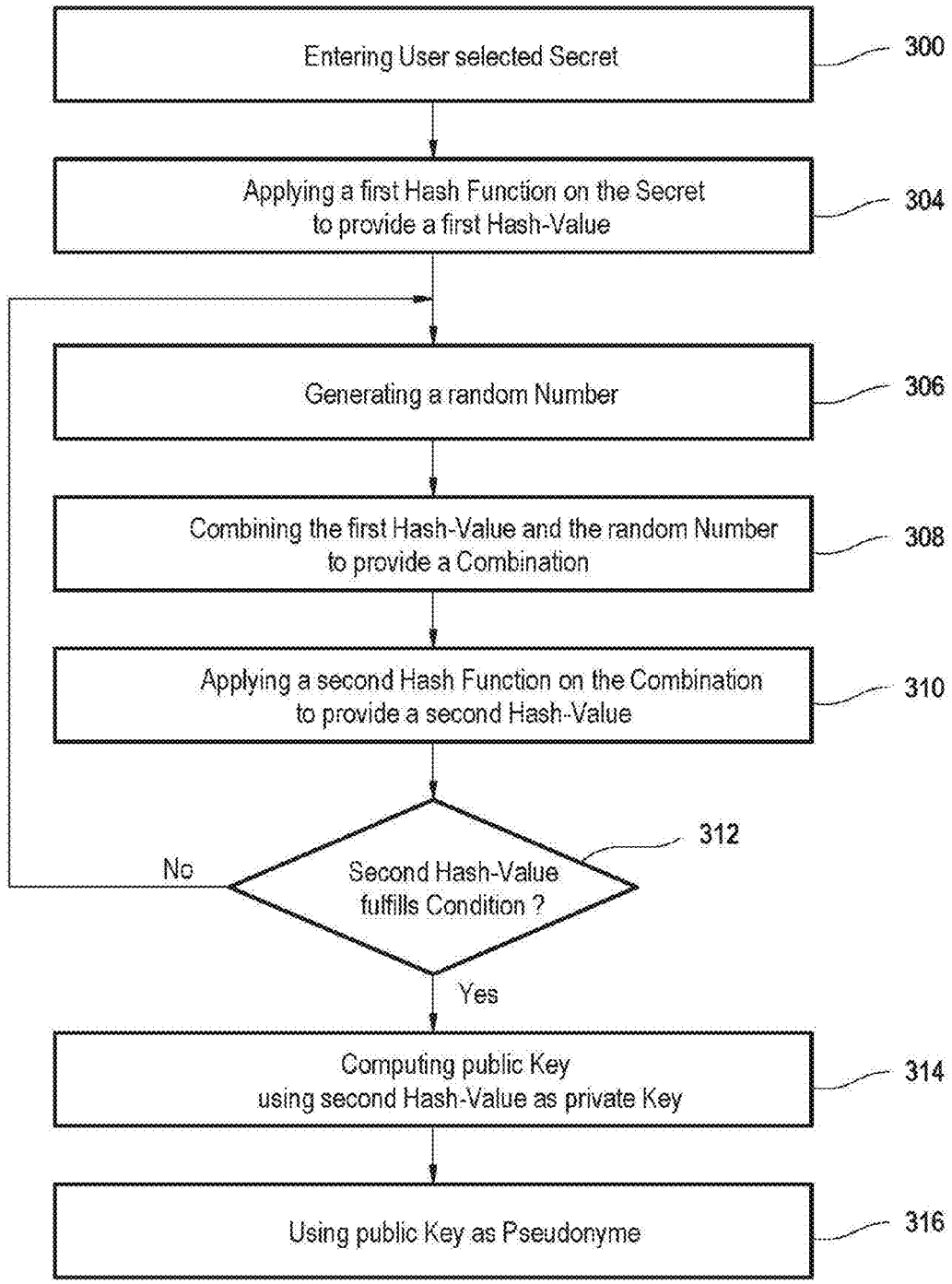
FIG. 13 is a flowchart being illustrative of a method for providing a pseudonym.

FIG. 13 shows a respective flowchart for generating a pseudonym $p_{T,i}$ for user $T_i$. In step 300 the user enters the user-selected secret $s_T$. In step 304 a first hash function is applied on the user-selected secret $s_T$ which provides a first hash value. In step 306 a random number is generated and in step 308 an embedding function is applied on the first hash value and the random number to provide a combination of the first hash value and the random number. In other words, the first hash value and the random number are mapped to a 1-dimensional space, e.g. a single number, by the embedding function. The combination can be obtained by concatenating the random number and the first hash value or by performing a bitwise XOR operation on the first hash value and the random number.

In step 310 a second hash function is applied on the combination which provides a second hash value. The second hash value is a candidate for the private key. Depending on the implementation the second hash value may only be usable as a private key if it fulfils one or more predefined conditions. For example, if ECC is used, it is checked whether the second hash value is within the interval between 2 and n−1, where n is the order of the elliptic curve.

Fulfillment of such a predefined condition is checked in step 312. If the condition is not fulfilled, the control returns to step 306. If the condition is fulfilled, then the second hash value qualifies to be used as a private key in step 314 to compute a respective public key providing an asymmetric cryptographic key-pair consisting of the private key and the public key. In step 316 the public key computed in step 314 is used as a pseudonym such as for accessing a pseudonym database, participation in an anonymous online community or other purposes.

According to further embodiments, the method for generating a pseudonym is implemented as a computer implemented method or instructions for a processor which are stored on a computer readable storage medium. An input value is accessed and a pseudonym is calculated by applying a cryptographic one-way function to the input value.

According to some embodiments, a first public key is calculated using the input value and a first base point. Elliptic curve cryptography is used to calculate the first public key. The input value in this embodiment is a private key suitable for use with elliptic curve cryptography. In a next step the first public key is output as a pseudonym. In a further step a second public key is calculated using the input value and a second base point. As with the calculation of the first public key the calculation of the second public key is performed using elliptic curve cryptography. In a further step the second public key is output as a public key for the use of the encryption of data.

According to further embodiments, a device such as a cell phone, a smart card or a security token is connected to a computer via a communication link. The cell phone may transfer a pseudonym to the computer via the communication link. In this embodiment the cell phone could also be other types of mobile computing devices. These include for example, but are not limited to: a personal digital assistant, an mp3 player, and a laptop. The communications link may be a variety of different types of communication link. It may be a wireless cell phone connection, it may be a Bluetooth connection, or it may be a wireless land connection, or it may be a LAN connection.

The cell phone comprises a processor. The processor is connected to a user interface and a memory. The user interface comprises a set of input keys and a display. However, it is understood that the input and the display may be combined into a single functional unit. For instance many cellular telephones, personal digital assistants, and mp3 players use touch sensitive screens. Instead of using input keys gestures or symbols on a touch sensitive screen may also be used. The display shows a message prompting a user to input a user-selected secret. The display also shows a cursor which shows a user where the value is input. The processor is also connected to a memory. Within the memory is shown the stored user-selected secret. The user-selected secret may be used to generate the input value. In some embodiments the user-selected secret may be identical with the input value. In other embodiments the user-selected secret may be used to generate the input value. An input value generator may be used to generate an input value from a user-selected secret. The input value may be equivalent to the private key as was discussed beforehand. The memory may also contain a cryptographic module which uses the input value to generate a pseudonym.

For instance the security token may be an RFID tag in which case the communications link is a radio frequency communications link. Alternatively, the security token may also be something as simple as a USB thumb drive. In this case the communications link is a USB bus. The security token comprises a microcontroller and a memory. The memory may contain the input value and an access control module. An optional access control module contains instructions for operation of the microcontroller which control access to the input value.

According to embodiments, the security token may be constructed such that the input value is stored in secure memory or memory which may be destroyed if the security token is disassembled. The computer comprises a processor and computer memory. The computer also comprises computer storage. During operation the processor may access via the communications link the input value stored in memory. The processor may then use a cryptographic module to generate the pseudonym.

The smart card may be connected to the computer via contacts or electrical connections when the communications link is simply a computer bus. However, if the smart card uses an RFID communications link then the communications link to the computer is via radio.

According to embodiments the smart card, which can function as electronic patientcard, is powered by a computer, e.g. a client computer system connected to a server computer system hosting the decision support system. In the case of electrical contacts then this is simply an electrical connection between the two of them. During operation the processor of the client computer system may request a pseudonym from the processor of the smart card. The client computer system may comprise a smart card access module which comprises instructions or commands which allow basic access to the smart card. When access is granted the processors will use the input value and the cryptographic module to calculate the pseudonym. In this embodiment, elliptic curve cryptography is used by the cryptographic module, whereby the cryptographic module uses a first base point to calculate the pseudonym.

Creating a Database Access Key

An input value may be stored in a computer memory or computer storage device or the input value may be generated. For example, the input value could be generated from a user-selected secret. In a further step an asymmetric cryptographic key pair is calculated. The input value could be used to generate both the public and private keys, or the input value could also possibly be the private key. In a further step the public key of the cryptographic key pair is outputted as the access key.

According to further embodiments, a method is provided comprising the steps of accessing an input value, calculating an asymmetric cryptographic key pair and outputting the public key of the cryptographic key pair as the access key. In a further step a digital signature for data, e.g. a data structure instance of data structure variant I-IV, which is to be deposited into a database, is generated by using the private key of the cryptographic key pair. According to embodiments, in a further step said data is deposited along with the digital signature into a database using the access key. The access key may be used to grant access to the database or as a permission to write data into the database or it may also serve as a reference for the data being deposited into the database. In a further the authenticity of the data is verified using the access key. The access key is the complimentary public key to the private key. The private key was used to generate the digital signature for the data and the public key can be used to verify the digital signature.

A client computer system 831 may comprise a display showing a message prompting a user to input a user-selected secret. The display also comprises and displays a cursor which shows a user where the value is input. The user-selected secret may be used to generate the input value. In some embodiments the user-selected secret may be identical with the input value. In other embodiments the user-selected secret may be used to generate the input value. An input value generator module may be used to generate an input value from a user-selected secret. The input value may be equivalent to the private key. The security module 840 may comprise a cryptographic module which uses the input value to generate a pseudonym.

According to embodiments, the cryptographic module is able to generate an access key using the input value. The client computer, which may also be a cell phone, a netbook or the like, is able to transmit the access key to the server computer 833 via a network. The computer system 833 comprises a processor, computer memory, and computer storage. The computer memory contains or is operatively connected to a database application program and data, in the following referred to as database 862. A database application program is any program or set of computer executable instructions which uses, accesses, and/or modifies a database.

The database application program may use the access key from the client computer to place data 750 into a database 862. The access key is stored with the data 750 to database 862. The access key could either be appended to the data or it could be referenced to the data. During use the client computer or cell phone could be used to generate an access key when a user wishes to store and/or modify data into the database. For instance a user could use his or her cell phone to produce an access key which is used for permission to post data to a bulletin board system or a social networking site. In another instance the cell phone could be used to provide verification for a financial transaction.

A security token or smart card 843 may be constructed such that the input value is stored in secure memory or memory which may be destroyed if the security token is disassembled. The client computer comprises a processor, computer memory and computer storage. During operation the processor of the client computer may access the input value 714 stored in memory. The processor of the client computer system 831 may then use a cryptographic module to generate the access key. The access key may be used as a pseudonym in some embodiments.

In the client computer the cryptographic module is adapted for using the input value for generating an access key. The cryptographic module can use the input value to generate a private key. The private key can be used to calculate a digital signature. The access key can be used by a database application program to enter the data 750 into database 862. The data has had the access key and the digital signature either appended to or referenced to the data. In embodiments the data contains a digital signature which could be used to verify the authenticity and/or authorship of the data using the access key (which functions also as a public key). In some embodiments a security token can be used for depositing data into a database or other file in a way which merely identifies the origin and authenticity of the data without revealing the author's identity.

The security modules 840 of the other client computer systems 830, 832 or of server computer 836 may likewise comprise a module for generating a pseudonym and for encrypting data transferred via a network. Preferentially, the data 750 is pseudonymized and encrypted at the moment when it is submitted from a client computer to one of the server computers 860, 833.

MATHEMATICAL APPENDIX

1. Embedding Functions.
   There exist n-ary scalar functions
   $$d: \mathbb{N} \times \mathbb{N} \to \mathbb{N}\, d$$
   which are injective—and even bijective, where $\mathbb{N}$ is the set of natural numbers. The function d( ) embeds uniquely an n-dimensional space, i.e. n-tuples $(k_1, \ldots, k_n)$, into scalars, i.e. natural numbers k.
2. The Binary Cantor Pairing Function
   The binary cantor pairing function $\pi$ is an embodiment of embedding function 132. The binary cantor pairing function is defined as follows:

$$\pi: \mathbb{N} \times \mathbb{N} \to \mathbb{N}$$
$$\pi(m, n) = \frac{1}{2}(m+n)(m+n+1) + n$$

which assigns to each fraction m/n the unique natural number $\pi(m, n)$—thus demonstrating that there are no more fractions than integers. Hence, if we map both $s_T$ and $V_T$,i to natural numbers and use the fact that all identities are distinct then $\pi(s_T, V_T, i)$ yields a unique value for each identity, even if there are equal personal secrets. To be more precise, since this function does not distinguish between e.g. ½, 2/4 etc, it assigns to each fraction an infinite number of unique natural numbers.

3. Elliptic Curve Cryptography (ECC)
   Let:
   p be a prime number, p>3, and $\mathbb{F}_p$ the corresponding finite field
   a and b integers
   Then the set E of points (x, y) such that $$E = \{(x,y) \in \mathbb{F}_p \times \mathbb{F}_p | y^2 = x^3 + ax + b\} \quad (F1)$$

defines an elliptic curve in $\mathbb{F}_p$. (For reasons of simplicity, we skip the details on E being non-singular and, as well, we do not consider the formulae of elliptic curves over finite fields with p=2 and p=3. The subsequent statements apply to these curves, too.) The number m of points on E is its order.

Let P,Q∈E be two points on E. Then the addition of points $$P+Q=R \text{ and } R \in E \quad (F2)$$

can be defined in such a way that E forms an Abelian group, viz, it satisfies the rules of ordinary addition of integers. By writing $$P+P=[2]P$$

We define the k-times addition of P as [k]P, the point multiplication.

Now EC-DLP, the elliptic curve discretionary logarithm problem, states that if $$Q=[k]P \tag{F3}$$

then with suitably chosen a, b, p and P, which are known to public, and the as well known to the public point Q it is computationally infeasible to determine the integer k.

The order n of a point P is the order of the subgroup generated by P, i.e. the number of elements in the set $$\{P,[2]P,\ldots,[n]P\} \tag{F4}$$

With all this in mind we define an elliptic curve cryptographic (ECC) system as follows. Let:

E be an elliptic curve of order m

B∈E a point of E of order n, the base point

Then $$D=\{a,b,p,B,n,co(B)\} \tag{F5}$$

with $$co(B) = \frac{m}{n}$$

defines a set of domain ECC-parameters. Let now g be an integer and $$Q=[g]B \tag{F6}$$

Then (g, Q) is an ECC-key-pair with g being the private key and Q the public key.

For we rely on findings of Technical Guideline TR-03111, Version 1.11, issued by the Bundesamt für Sicherheit in der Informationstechnik (BSI), one of the best accredited source for cryptographically strong elliptic curves, we can take that m=n, i.e. co(B)=1, and hence reduce (F5) to $$D=\{a,b,p,B,n\} \tag{F7}$$

Now we can define our one-way function. Let D be a set of domain parameters concordant with (F7). Then $$f:[2,n-1]\to E$$

$$k \mapsto [k]B \tag{F8}$$

i.e. the point multiplication (F6), is an injective one-way function.

4. Implementing Key Generator Based on ECC

The key generator 128 (cf. FIGS. 1 and 3) can be implemented using ECC.

DEFINITIONS

There are public sets of ECC-domain parameters $D_1$, $D_2$, ... concordant with (F7)

$$D_i=\{a_i,b_i,p_i,B_i,n_i\} \tag{F9}$$

There are public functions: an embedding function d( ), a randomising function r( ) and our one-way function f( ) defined by (F8).

There is a public set of enrolled participants (users)

$$T=\{T_1,T_2,\ldots\} \tag{F10}$$

Note that a $T_i$ does not necessarily possess any personally identifying details, i.e. we assume that T resembles the list of participants in an anonymous Internetcommunity, in which each participant can select his name at his discretion as long as it is unique.

Each participant T∈T chooses at his complete discretion his personal secret $s_T$. In particular, for this secret is never revealed to anybody else—it is the participant's responsibility to ensure this—it is not subject to any mandatory conditions, such as uniqueness.

Our pseudonym derivation function is $$h(\ )=f(r(d(\ ))) \tag{F11}$$

with the following properties:

Given a T∈T with his $s_T$, a $D_i$ and T, $D_i \in V_{T,i}$ $$r(d(s_T,V_{T,i}))=g_{T,i} \tag{F12}$$

where $g_{T,i}$ is a unique and strong, i.e. sufficiently random, private ECC-key for $D_i$.

The pseudonym $p_{T,i}$ corresponding to T, $s_T$ and $D_i$ is $$p_{T,i}=f(g_{T,i},D_i)=[g_{T,i}]B_i=(x_{T,i},y_{T,i}) \tag{F13}$$

There is a public set of pseudonyms $$P=\{p_1,p_2,\ldots\} \tag{F14}$$

such that P comprises one or more pseudonyms for each participant in T computed according to (F11). This wording implies that here is no recorded correspondence between a participant in T and his pseudonyms in P, i.e. each $p_{T,i}$ is inserted in an anonymous way as $p_k$ into P.

Remarks:

The use of multiple domain parameters enables us to endow a single participant with a single personal secret with multiple pseudonyms. This in turn enables a participant to be a member of multiple pseudonymous groups such that data of these groups cannot—for, e.g. personal or legal reasons—be correlated. Therefore, attempts to exploit combined pseudonymous profiles for unintended, possibly malicious purposes, are of no avail.

The distinction between two sets of domain parameters $D_i$ and $D_j$ can be minor. In accordance with our principle to use only accredited domain parameters, e.g. those listed in BSI TR-03111, we can set $$D_i=\{a,b,p,B,n\} \tag{F15}$$

by swapping B for a statistically independent $B_2$, i.e. by choosing a different base point, we can set $$D_j=\{a,b,p,B_2,n\} \tag{F16}$$

For $D_i$ and $D_j$ refer to the same elliptic curve we can have only one function (F12) and introduce the crucial distinction with (F13). This vastly simplifies concrete implementations—we select a suitable curve and vary the base points only.

LIST OF REFERENCE NUMBERS

100 Computer system
102 User interface
104 Keyboard
106 Sensor
108 Memory
110 Processor
112 A user-selected secret
114 Combination
116 Private key
118 Public key
120 Data object/Data structure
122 Computer program instructions
124 Combination generator
126 Embedding and randomizing function
128 Key generator
130 Database access function 132 Embedding function
134 Randomizing function
136 Network interface
138 Database
140 Network
144 Analytic system/DSS
146 Component
148 Random number generator
150 Hash function
152 Hash function
154 Database
156 Online community
158 User profile
170-182 Steps
230 Dialog window
231 GUI pane
232 Catalog selector
233 Catalog selector
234-236 Search fields
238 Entered search phrase
239-241 Selected allergy
241 Suggested terms
242 First list of GUI elements
243 Second list of GUI elements
244 Third list of GUI elements
245 Cancel button
246 Save button
330 ATC level I
331 ATC level II
332 ATC level V
333-335 Search fields
336-338 GUI elements
339-341 Selected allergen
450 Dialog window
451 Patient record
452 personal data
453 Chronic diagnoses
454 Chronic medication
455 Patient related data
457 Notification dialog box
458 'Literature' button
459 'Reminder' button
460 Confirmation button
461 'Write prescription' button
462 scrollable GUI pane
530 Electronic questionnaire
532-536 Symptom rows
537 Group of squares
538 Close button
539-541 Square GUI elements
542 Message comprising a medical decision
543 Selected GUI elements
544 Unselected GUI element
600 Dialog window
601-603 GUI areas
604 List of values to map
605 List of potential mapping targets
606 List of LOINC identifiers
607 List of units
608 List of tissues
620 selectable GUI element
621 selectable GUI element
622 selectable GUI element
671 Search field
672 Resulting LOINC code
673 Human readable LOINC code
740-743 Data sources
744 Graphical user interface
745 Data structure instantiation module
746 Mapping module
747 Catalog repository
748 Rules engine
749 Rules repository
750 Data structure
751 Decision support system
752-755 Decision support modules
756 Communication layer
757-758 Modules of the communication layer
759 Standalone doctor information system
760 Client
761 GUI engine
832 Client machine
833 Server
834 Computer centre
835 Computer centre
836 Computer centre
837 Backend server
838 GUI manager
839 Firewall
840 Security interface
842 Browser
844 Public key infrastructure server
846 Web interface
860 Server
861 Server security interface
862 Central database
950 Data structure
951 Timestamp

The invention claimed is:

1. A computer-implemented method for generating a specification of a data structure, the data structure to be used as input for a medical decision support system, the data structure comprising a plurality of biomedical parameters, the method comprising the following steps performed on a processor:

determining, for a particular population of persons received via a communications device, a first set of diseases, each disease being represented by a data object, wherein each disease belonging to the determined set of diseases has assigned an absolute or relative frequency value within said population, storing each data object on a non-transitory computer readable medium, said each data object representing a disease of the first set of diseases in association with the determined frequency value of the represented disease, sorting the diseases of the first set of disease according to their assigned frequency values, determining a second set of diseases, wherein the second set of diseases is a sub-set of the first set of diseases, the sub-set being created by leaving out all diseases of the first set of diseases which are biomechanical diseases, determining a third set of diseases, the third set of diseases being built by executing the sub-steps:

A) determining, for each disease of the second set of diseases, a number of predictive parameters of said disease, B) assigning a score value to each disease, the score value positively correlating with the frequency value of a disease and negatively correlating with the number of parameters correlating with or characterizing said disease, and sorting the diseases of the second set of diseases according to their assigned score values, C) adding a disease of the second set of diseases which has assigned the highest score value and which in addition has not yet been added to the third set of diseases to the third set of diseases, D) calculating a first sum, the first sum being calculated by summing up all frequency values of the diseases having yet being added to the third set of diseases, E) if the first sum is below a coverage threshold value, repeating steps C and D, and if the first sum equals or exceeds said coverage threshold value, continuing with step F and using the third set of diseases and the first sum as result, and F) compiling the plurality of biomedical parameters by determining, for each of the diseases in the third set of diseases, at least one biomedical parameter being indicative of the presence of said disease, whereby the compilation of the biomedical parameters constitutes the specification of the data structure wherein the plurality of biomedical parameter values comprises a first set of parameter values, each parameter value of the first set of biomedical parameter values being a laboratory value having been derived by analyzing a body fluid or tissue of a person, the first set of parameter values comprising:
glucose concentration,
LDL concentration,
HDL concentration,
triglyceride concentration,
creatinine concentration,
cholesterol concentration,
Hba1c concentration, and
C Reactive Peptide (CRP) concentration,
wherein the plurality of biomedical parameter values comprises a second set of parameter values of the person, the second set of data values comprising:
age,
gender,
body mass index (BMI),
waist/hip ratio,
blood pressure, and
smoking history
wherein the parameter set is the minimum parameter set required to allow monitoring of a wide range of the most common diseases.

2. The computer-implemented method according to claim 1, further comprising the step of instantiating the specified data structure by assigning each biomedical parameter of the data structure at least one biomedical parameter value of a person.

3. The computer-implemented method according to claim 2, wherein the instantiated data structure is assigned a pseudonym of the person, the method further comprising the steps:
entering a user-selected secret,
storing the user-selected secret in memory,
computing a private key by applying an embedding and randomizing function onto the secret,
storing the private key in the memory,
computing a public key using the private key, the public key and the private key forming an asymmetric cryptographic key,
erasing the secret and the private key from the memory,
outputting the public key for providing the pseudonym, and
assigning the pseudonym to the data structure.

4. The computer-implemented method according to claim 1, the method further comprising the step of adding to at least one biomedical parameter value a timestamp value, the timestamp value being indicative of the time and date the biomedical parameter value was received or created.

5. The computer-implemented method according to claim 1, wherein at least one biomedical parameter of the data structure is assigned a parameter value by executing the steps of:
receiving at least one biomedical catalog;
presenting a tree to a user via a graphical user interface, the nodes of the tree being a graphical representation of the elements of the received biomedical catalog, the tree providing the user with means to navigate in the tree structure;
receiving, upon selection of a tree node by the user, information being indicative of the element of the catalog represented by the selected tree node; and
assigning the identifier of the indicated catalog element as parameter value to the at least one biomedical parameter.

6. The computer-implemented method according to claim 1, wherein at least one biomedical parameter of the data structure is assigned a parameter value by executing the steps:
displaying on a graphical user interface a first list of first selectable Graphic User Interface (GUI) elements, each first selectable GUI element representing a laboratory parameter,
displaying, upon selection of a laboratory parameter of the first list by a user, a list of second parameter names having a similar parameter name like the selected laboratory parameter, each second parameter name being automatically determined and being represented as a second selectable GUI element,
displaying on the graphical user interface:
third selectable GUI elements for selecting a Logical Observation Identifiers Names and Codes (LOINC) name,
fourth selectable GUI elements for selecting a system of units,
fifth selectable GUI elements for selecting the tissue the selected laboratory parameter was derived from, and
a display element, the display element displaying a LOINC code, the LOINC code being determined automatically based on the selected third, fourth and fifth selectable GUI elements,
using the LOINC code as identifier of the laboratory parameter value.

7. The method of claim 1, wherein the first set of parameter values further comprises:
International Normalized Ratio (INR),
potassium concentration, and
at least one of Thyrotropic hormone or Thyroid stimulating hormone (collectively TSH) concentration.

8. The method of claim 7, wherein the first set of parameter values further comprises:
gamma-glutamyltransferase concentration,
alanine transaminase concentration, and
hemoglobin concentration.

9. The method of claim 8, wherein the first set of parameter values further comprises:
Leukocyte concentration,
Albumin concentration, and
Hämohapto value Stool,
and wherein the second set of parameter values further comprises:
body height,
body weight,
body temperature,
hip circumference,
waist circumference,
the systolic blood pressure,
the mean blood pressure, the diastolic blood pressure,
the pulse rate,
allergies and intolerances, and
the medication history of the person.

10. The method of claim 1, wherein the second set of parameter values further comprises the ethnicity of the person.

11. The method of claim 1, wherein at least one parameter value of the plurality of parameter values has assigned at least one timestamp value, the at least one timestamp value being indicative of the time and date of having received, specified or measured the data value.

12. A non-transitory computer readable storage medium having stored therein instructions, which when executed by a computing device cause the computing device to perform a method of generating an access key, the method comprising the steps of:
   accessing an input value;
   calculating an asymmetric cryptographic key pair by applying a cryptographic one-way function to the input value, wherein the cryptographic key pair comprises a public key and a private key, wherein the cryptographic one-way function is an injective function; and
   outputting the public key for providing the access key, and
   storing a data structure into a database whereby the provided access key is used as database key, wherein the data structure comprises a plurality of biomedical parameter values for use in a medical decision support system, wherein the plurality of biomedical parameter values comprises a first set of parameter values, each parameter value of the first set of biomedical parameter values being a laboratory value having been derived by analyzing a body fluid or tissue of a person, the first set of parameter values comprising:
   glucose concentration,
   LDL concentration,
   HDL concentration,
   triglyceride concentration,
   creatinine concentration,
   cholesterol concentration,
   Hba1c concentration, and
   C Reactive Peptide (CRP) CRP concentration,
   wherein the plurality of biomedical parameter values comprises a second set of parameter values of the person, the second set of data values comprising:
   age,
   gender,
   body mass index (BMI),
   waist/hip ratio,
   blood pressure, and
   smoking history
   wherein the parameter set is the minimum parameter set required to allow monitoring of a wide range of the most common diseases.

13. The non-transitory computer-readable storage medium of claim 12, wherein the method further comprises the step of generating a digital signature for the data structure using the private key, and wherein the digital signature is stored into the database in association with the data structure.

14. A computer system comprising a server-computer system, the server-computer system comprising:
   an interface configured to receive a data structure via a network connection from a client computer system, wherein the data structure comprises a plurality of biomedical parameter values for use in a medical decision support system, wherein the plurality of biomedical parameter values comprises a first set of parameter values, each parameter value of the first set of biomedical parameter values being a laboratory value having been derived by analyzing a body fluid or tissue of a person, the first set of parameter values comprising:
   glucose concentration,
   LDL concentration,
   HDL concentration,
   triglyceride concentration,
   creatinine concentration,
   cholesterol concentration,
   Hba1c concentration, and
   C Reactive Peptide (CRP) concentration,
   wherein the plurality of biomedical parameter values comprises a second set of parameter values of the person, the second set of data values comprising:
   age,
   gender,
   body mass index (BMI),
   waist/hip ratio,
   blood pressure, and
   smoking history
   wherein the parameter set is the minimum parameter set required to allow monitoring of a wide range of the most common diseases
   a processor,
   a first non-transitory computer-readable storage medium comprising instructions which, when executed by the processor, provide for a decision support system, the decision support system in operation receiving the data structure from the interface and calculating a medical decision based on the received data structure,
   wherein the decision support system in operation calculates a medical decision based on the biomedical parameters contained in the received data structure.

15. The computer system according to claim 14, wherein the decision support system is a modular decision support system comprising one or more modules, each module being operable to calculate a different medical decision.

16. The computer system according to claim 14, wherein the client-computer system comprises a second computer-readable storage medium, the second computer readable storage medium comprising instructions which, when executed by the processor, causes said processor to perform a method of generating an access key, the method comprising the steps of:
   accessing an input value;
   calculating an asymmetric cryptographic key pair by applying a cryptographic one-way function to the input value, wherein the cryptographic key pair comprises a public key and a private key, wherein the cryptographic one-way function is an injective function; and
   outputting the public key for providing the access key,
   depositing the data structure together with the medical decision into a database using the provided access key via the interface, the database being operatively coupled to the decision support system.

* * * * *